(12) United States Patent
Hao et al.

(10) Patent No.: US 10,112,918 B2
(45) Date of Patent: Oct. 30, 2018

(54) 15-OXOSPIRAMILACTONE DERIVATIVES, PREPARATION METHOD AND USES THEREOF

(71) Applicants: Kunming Institute of Botany, The Chinese Academy of Sciences, Kunming, Yunnan (CN); The Key Laboratory of Chemistry for Natural Product of Guizhou Province & Chinese Academy of Science, Guiyang, Guizhou (CN); Shanghai Institutes for Biological Sciences, CAS, Shanghai (CN); Institute of Zoology, Chinese Academy of Sciences, Beijing (CN)

(72) Inventors: Xiaojiang Hao, Yunnan (CN); Chen Yan, Guizhou (CN); Haiyang Liu, Yunnan (CN); Lin Li, Shanghai (CN); Xiaoli He, Shanghai (CN); Quan Chen, Beijing (CN)

(73) Assignees: Kunming Institute of Botany, The Chinese Academy of Sciences, Kunming, Yunnan (CN); The Key Laboratory of Chemistry for Natural Product of Guizhou Province and Chinese Academy of Science, Guiyang, Guizhou (CN); Shanghai Institutes of Biological Sciences, CAS, Shanghai (CN); Institute of Zoology, Chinese Academy of Sciences, Beijing (CN)

( * ) Notice: Subject to any disclaimer, the term of this patent is extended or adjusted under 35 U.S.C. 154(b) by 110 days.

(21) Appl. No.: 14/785,075

(22) PCT Filed: Apr. 21, 2014

(86) PCT No.: PCT/CN2014/000432
§ 371 (c)(1),
(2) Date: Feb. 9, 2016

(87) PCT Pub. No.: WO2014/169711
PCT Pub. Date: Oct. 23, 2014

(65) Prior Publication Data
US 2016/0185743 A1 Jun. 30, 2016

(30) Foreign Application Priority Data

Apr. 19, 2013 (CN) .......................... 2013 1 0137548
Jul. 17, 2013 (CN) .......................... 2013 1 0300116

(51) Int. Cl.
*C07C 69/16* (2006.01)
*C07C 69/18* (2006.01)
(Continued)

(52) U.S. Cl.
CPC .......... *C07D 311/78* (2013.01); *A61K 31/366* (2013.01); *C07C 49/743* (2013.01);
(Continued)

(58) Field of Classification Search
None
See application file for complete search history.

(56) References Cited

U.S. PATENT DOCUMENTS

2007/0197488 A1* 8/2007 Peters .................. C07J 41/0044
514/171

FOREIGN PATENT DOCUMENTS

CN 101239964 A 8/2008
CN 102058580 A 5/2011
(Continued)

OTHER PUBLICATIONS

2007. Isomer. Hawley's Condensed Chemical Dictionary. 711.*
(Continued)

*Primary Examiner* — Alicia L Otton
(74) *Attorney, Agent, or Firm* — Honigman Miller Schwartz and Cohn LLP; Thomas A. Wootton, Esq.; Jonathan P. O'Brien

(57) ABSTRACT

The invention relates to a derivative of 15-oxospiramilacton, particularly to a compound of Formula I or II, or an isomer, a solvate or a pharmaceutically acceptable salt thereof. The invention also relates to a pharmaceutical composition comprising the compound as pharmaceutically active ingredient, a method for preparing the same, and use thereof in manufacture of an anti-tumor agent. The derivative of 15-oxospiramilactone of the invention have an activity against multiple tumor cell lines, and the anti-tumor activity is positively correlated to an activity inhibiting the Wnt signaling pathway.

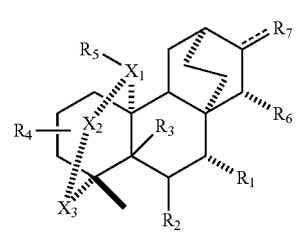

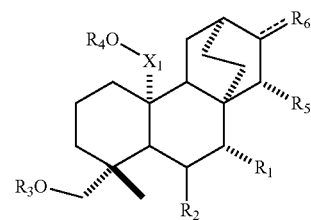

6 Claims, No Drawings

(51) Int. Cl.
| | |
|---|---|
| C07C 69/26 | (2006.01) |
| C07C 69/30 | (2006.01) |
| C07C 69/63 | (2006.01) |
| C07C 69/78 | (2006.01) |
| C07C 49/743 | (2006.01) |
| C07C 62/38 | (2006.01) |
| C07C 205/57 | (2006.01) |
| C07D 295/116 | (2006.01) |
| C07D 295/185 | (2006.01) |
| C07D 333/40 | (2006.01) |
| C07D 311/78 | (2006.01) |
| A61K 31/366 | (2006.01) |
| C07D 311/94 | (2006.01) |
| C07D 407/12 | (2006.01) |
| C07D 221/28 | (2006.01) |
| C07D 327/10 | (2006.01) |
| C07D 409/12 | (2006.01) |
| C07D 493/08 | (2006.01) |
| C07D 493/10 | (2006.01) |
| C07D 495/04 | (2006.01) |
| C07D 498/08 | (2006.01) |
| C07C 309/66 | (2006.01) |
| C07C 49/753 | (2006.01) |

(52) U.S. Cl.
CPC ............ *C07C 49/753* (2013.01); *C07C 62/38* (2013.01); *C07C 69/16* (2013.01); *C07C 69/18* (2013.01); *C07C 69/26* (2013.01); *C07C 69/30* (2013.01); *C07C 69/63* (2013.01); *C07C 69/78* (2013.01); *C07C 205/57* (2013.01); *C07C 309/66* (2013.01); *C07D 221/28* (2013.01); *C07D 295/116* (2013.01); *C07D 295/185* (2013.01); *C07D 311/94* (2013.01); *C07D 327/10* (2013.01); *C07D 333/40* (2013.01); *C07D 407/12* (2013.01); *C07D 409/12* (2013.01); *C07D 493/08* (2013.01); *C07D 493/10* (2013.01); *C07D 495/04* (2013.01); *C07D 498/08* (2013.01); *C07C 2603/86* (2017.05)

(56) References Cited

FOREIGN PATENT DOCUMENTS

| | | |
|---|---|---|
| CN | 103193754 A | 7/2013 |
| CN | 103360358 A | 10/2013 |

OTHER PUBLICATIONS

Pelletier, S. William et al., "Conformational Analysis of the Oxazolidine and Tetrahydro-1,3-oxazine Ring of C20-Diterpenoid Alkaloid Derivatives", The Journal of Organic Chemistry, 48(11):1787-1796, 1983.

Aneja, R. and Pelletier, S. W., "The Diterpene Alkaloids. The Structure of Heteratisine", Tetrahedron Letters, 12:669-677, 1964.

Hao, Xiao-Jiang et al., "The Chemical Structures of Spiramine J, K, L and M", Acta Botanica Yunnanica, 14(3):314-318, 1992.

Wang, Wei et al., "A diterpenoid derivative 15-oxospiramilactone inhibits Wnt/β-catenin signaling and colon cancer cell tumorigenesis", Cell Research, 21:730-740, 2011.

Hong, Xin et al., "A New Diterpene From Spiraea japonica", Chinese Chemical Letters, 7(2):133-134, 1996.

Li, Ling et al., "Antiplatelet aggregation activity of diterpene alkaloids from Spiraea japonica", European Journal of Pharmacology, 449:23-28, 2002.

Nabors, J. B. et al., "Preparation and Optical Rotatory Dispersion Study of Tetracyclic Diterpenoid Intermediates", Tetrahedron, 27:2385-2898, 1971.

* cited by examiner

15-OXOSPIRAMILACTONE DERIVATIVES, PREPARATION METHOD AND USES THEREOF

CROSS-REFERENCE TO RELATED APPLICATIONS

This application claims priority under 35 U.S.C. § 371 to Patent Cooperation Treaty application PCT/CN2014/000432, filed Apr. 21, 2014, which claims the benefit of Chinese Patent Application No. 201310300116.2, filed Jul. 17, 2013, and the benefit of Chinese Patent Application No. 201310137548.6, filed Apr. 19, 2013, the entire contents of which are incorporated herein by reference.

TECHNICAL FIELD

The invention belongs to the field of pharmaceutical technology. In particular, the invention relates to a derivative of 15-oxospiramilactone (S-3) a diterpene from *Spiraea*, a method for preparing the derivative, a pharmaceutical composition comprising the derivative as active ingredient, and use thereof in manufacture of an anti-tumor agent.

BACKGROUND ART

Although a great progress has been achieved in the science of oncology, so far, cancer is still the most serious problem in the world threaten public health. It is predicted that new cancer cases will increase to more than 20 million in 2030 in the worldwide from 12.7 million in 2008. Tumor has become the first killer of human health. "Poor cancer" maintains a high incidence, and "rich cancer" also increases rapidly. Cancer spectrum in China is transitioning from the high-incidence in developing countries to the high-incidence in developed countries. The factors responsible for the tendency toward the young among cancer patient in China include environmental pollution, unhealthy life style, high mental stress and the like. Meanwhile, another factor for the serious situation of cancer is rapid aging of population.

Currently, the clinical means for treating cancer include surgery, radiotherapy and chemotherapy. Although these means are therapeutically effective to some extent, they bring about enormous physical and mental sufferings to patients due to great toxic and side-effects. In addition, another important problem that affects the chemotherapeutic effect is the tolerance to cytotoxic agents. Some cancer cells not only tolerated one anti-tumor agent, but also resist to agents of a totally different class, which is the main factor for the failure of the treatment of tumor with chemical agents (chemotherapy). For many anti-tumor agents of natural source, such as alkaloids (colchicine, vinblastine, harringtonine, taxol, etc.), anthracycline antibiotics (adriamycin and daunorubicin), epipodophyllotoxins (Vp-16 and VM-26), and synthetic agents (mitoxantrone and amsacrine), MDR is apt to occur. Even for newly discovered agents, such as paclitaxel and STI-571 for treating chronic myeloid leukemia, drug-resistant are found soon after being applied in clinic, which makes the problem more serious.

However, there is a great difference in signaling pathway between normal cells and tumor cells, which provides a new opportunity for development of anti-tumor agents having the characteristics such as tumor-targeting, high efficiency, and low toxicity. Up to now, there is still no report concerning the derivatives of 15-oxospiramilactone (S-3) of the invention in the prior art.

CONTENTS OF THE INVENTION

The object of the invention is to provide a compound of Formula I or II, or an isomer, a solvate or a pharmaceutically acceptable salt thereof, a method for preparing the same, a pharmaceutical composition comprising the compound as pharmaceutically active ingredient, and use thereof in manufacture of an anti-tumor agent or a medicament for preventing or treating a disease or disorder caused by abnormal inactivation of the canonical Wnt signaling pathway.

In the first aspect, the invention relates to a compound of Formula I, or an isomer, a solvate or a pharmaceutically acceptable salt thereof,

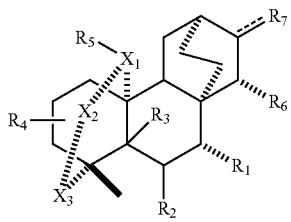

I wherein:

$R_1$ is selected from groups of hydroxyl, carbonyl oxygen, $C_{1-6}$alkylacyloxy, benzoyloxy, $C_{1-6}$ alkylsulfonyloxy, phenylsulfonyloxy, phenylmethylsulfonyloxy, benzoyl, and cinnamoyloxy, wherein said groups are optionally substituted with one or more (e.g., 2, 3 or 4) substituents selected from halogen, $C_{1-6}$alkyl, $C_{2-6}$alkenyl, nitro, $C_{1-6}$alkoxy, triazo, trifluoromethyl, furyl, and thienyl; or $R_1$ is —OCO$(CH_2)_n CH_2 X$, wherein n=1-8, X is halogen; or $R_1$ is —OCOCH$_2$-biotin or —OCO(CH$_2$)$_9$C$_2$HN$_3$CH$_2$NH-biotin;

$R_2$ is selected from —H, carbonyl oxygen, =CH$_2$, halogen, —SCH$_3$, —CH$_2$OH, —CH$_2$N(CH$_3$)$_2$, —CH$_2$N(CH$_2$)$_4$O, —CH$_2$OCOCH$_3$, —CH$_2$OSO$_2$CH$_3$, —CH$_2$NR$_8$R$_9$, and —CH$_2$R$_1$, wherein R$_8$ and R$_9$ are hydrogen, C1-6alkyl or aryl, and may be the same or different, or may form a 5-membered or 6-membered ring together with the N atom which they are linked to;

$R_3$ is —H or $R_2$ and $R_3$ form a double bond between the carbon atoms which they are linked to;

═ represents a double bond or a single bond, and $R_7$ is —CH$_2$, when ═ represents a single bond, $R_7$ is further linked to the C atom on the ring via an oxo bridge, or a N-containing 5-membered or 6-membered ring;

$X_1$ and $X_3$ are independently selected from —CH$_2$, —CH and carbonyl;

$X_2$ is an oxygen atom, a nitrogen atom or —O—S(O)—O—;

$R_6$ is —OH or carbonyl oxygen;

when $X_1$ is CH, $R_5$ is —OCH$_3$ or $R_1$ and $R_5$ form an oxo bridge;

when $X_2$ is a nitrogen atom, $R_1$ is selected from —H, —CH$_2$CH$_2$OH, —CH$_2$CH$_2$OTBDMS, $C_{1-6}$ alkyl and —CH$_2$CH$_2$R$_1$, $R_5$ is carbonyl oxygen or hydrogen, or $R_4$, $R_5$, $X_1$, and $X_2$ form an oxazole ring or $R_4$, $X_2$, and $X_3$ form an oxazole ring.

The compound, or the isomer, solvate or pharmaceutically acceptable salt thereof according to any item of the first aspect of the invention, wherein $R_1$ is selected from formyloxy, acetoxy, 2-chloroacetoxy, 2-bromoacetoxy, 2-triazoacetoxy, trifluoroacetoxy, acryloyloxy, 3-chloropropionyloxy, 2-chloropropionyloxy, benzoyloxy, p-nitrobenzoyloxy, o-nitrobenzoyloxy, m-nitrobenzoyloxy, p-methoxybenzoyloxy, p-trifluoromethylbenzoyloxy, o-trifluoromethylbenzoyloxy, m-trifluoromethylbenzoyloxy, 2-furoyloxy, 3-furoyloxy, 2-thenoyloxy, 3-thenoyl oxy, cinnamoyloxy, methyl sulfonyloxy, phenylmethyl sulfonyloxy, phenylsulfonyloxy, p-chlorophenylsulfonyloxy, m-chlorophenylsulfonyloxy, o-chlorophenylsulfonyloxy, and o-nitrobenzoyl.

In the second aspect, the invention relates to a compound of Formula II, or an isomer, a solvate or a pharmaceutically acceptable salt thereof,

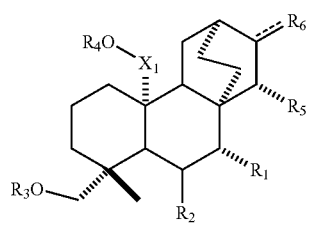

II wherein, $R_1$ and $R_5$ independently are —OH, or carbonyl oxygen;

$R_2$ is selected from —H, carbonyl oxygen, =$CH_2$, —$CH_2OH$, —$CH_2N(CH_2)_4O$, —$CH_2OCOCH_3$, —$CH_2OSO_2CH_3$, halogen, —$CH_2NR_7R_8$, and —$CH_2R_1$, wherein $R_7$ and $R_8$ may be the same or different, or may form a N-containing 5-membered or 6-membered ring together with the N atom which they are linked to;

represents a double bond or a single bond, and R6 is —CH2, when represents a single bond, $R_6$ is linked to the C atom on the ring via an oxo bridge, or a N-containing 5-membered or 6-membered ring;

$R_3$ and $R_4$ are independently selected from groups of —OH, —$COCH_3$, —$COCH_2CH_3$, —$COCH_2Cl$, —$CON(CH_2)_4O$, -Ms, —$CH_2CN$, 2-thenoyl and benzoyl; or $R_3$ and $R_4$ are independently selected from groups of hydroxyl, carbonyl oxygen, $C_{1-6}$alkylacyl, benzoyl, $C_{1-6}$alkylsulfonyl, phenyl sulfonyl, phenylmethylsulfonyl, and cinnamoyl, wherein said groups are optionally substituted with one or more (e.g., 2, 3, or 4) substituents selected from halogen, $C_{1-6}$alkyl, $C_{2-6}$alkenyl, nitro, $C_{1-6}$alkoxy, triazo, trifluoromethyl, furyl, and thienyl; or $R_3$ and $R_4$ independently are —$CO(CH_2)nCH_3$ or —$CO(CH_2)_nCH2X$, wherein n=1-8, X is halogen;

$X_1$ is —$CH_2$ or —CO.

The compound, or the isomer, solvate or pharmaceutically acceptable salt thereof according to any item of the second aspect of the invention, wherein $R_3$ and $R_4$ are independently selected from —OH, —$COCH_3$, —$COCH_2CH_3$, —$COCH_2Cl$, —$CON(CH_2)_4O$, -Ms (mesyl), —$CH_2CN$, 2-thenoyl, benzoyl, p-nitrobenzoyl, formyl, acetyl, 2-chloroacetyl, 2-bromoacetyl, 2-triazoacetyl, trifluoroacetyl, acryloyl, 3-chloropropionyl, 2-chloropropionyl, benzoyl, p-nitrobenzoyl, o-nitrobenzoyl, m-nitrobenzoyl, p-methoxybenzoyl, p-trifluoromethylbenzoyl, o-trifluoromethylbenzoyl, m-trifluoromethylbenzoyl, 2-furoyl, 3-furoyl, 2-thenoyl, 3-thenoyl, cinnamoyl, methyl sulfonyl, phenylmethylsulfonyl, phenyl sulfonyl, p-chlorophenylsulfonyl, m-chlorophenylsulfonyl, o-chlorophenylsulfonyl, and o-nitrobenzoyl.

The compound, or the isomer, solvate or pharmaceutically acceptable salt thereof according to any item of the first aspect or the second aspect of the invention, which is selected from the following compounds:

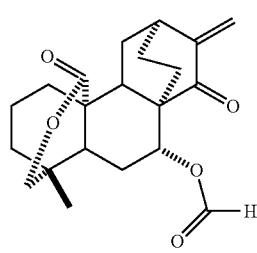

(1a)

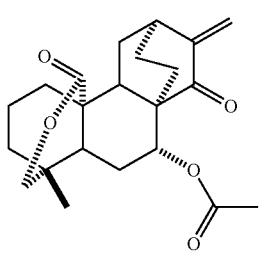

(1b)

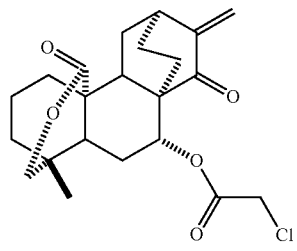

(1c)

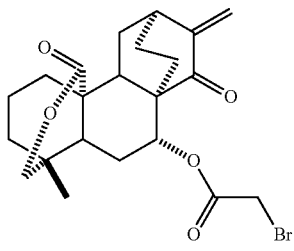

(1d)

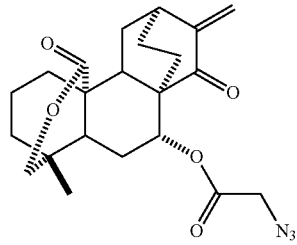

(1e)

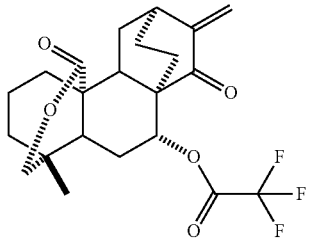

(1f)

(1g)
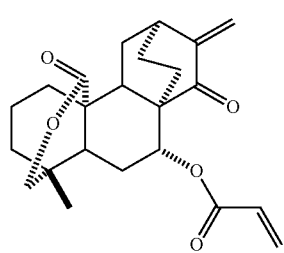
(1h)
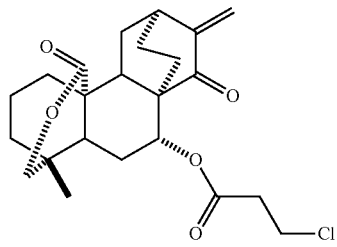
(1i)
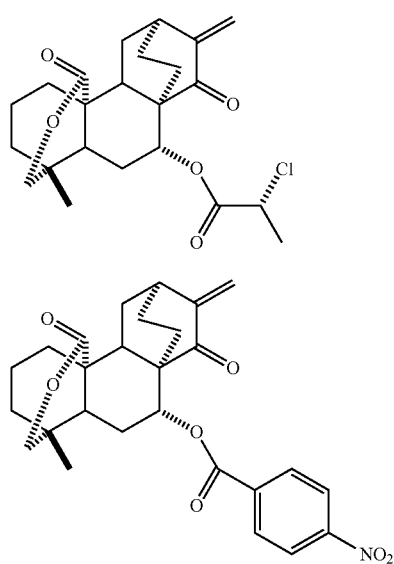
(1j)
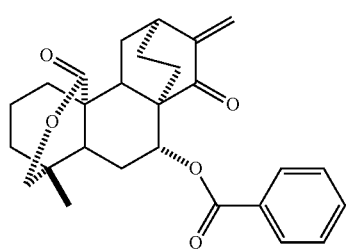
(1k)
(1l)
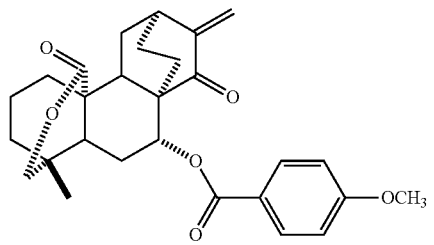
(1m)
(1n)
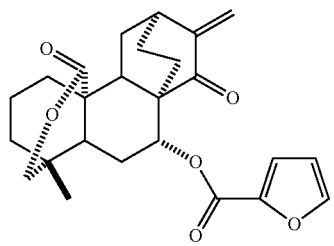
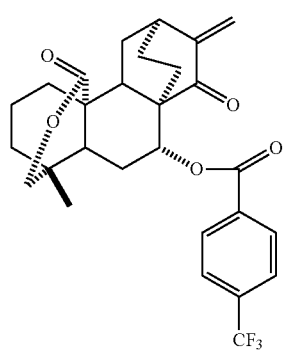
(1o)
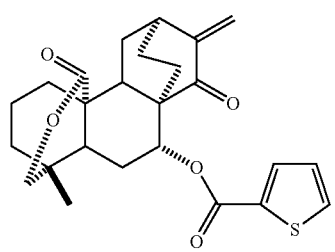
(1p)
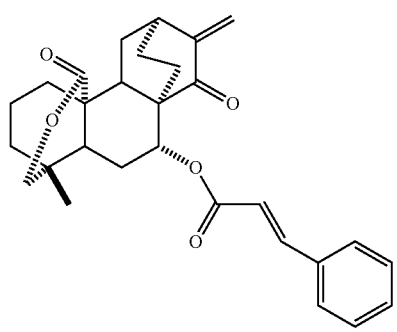

-continued
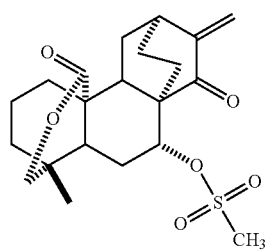
(1q)
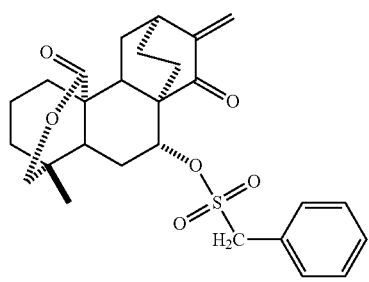
(1r)
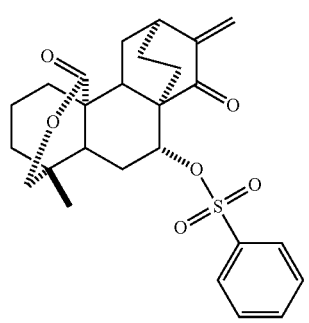
(1s)
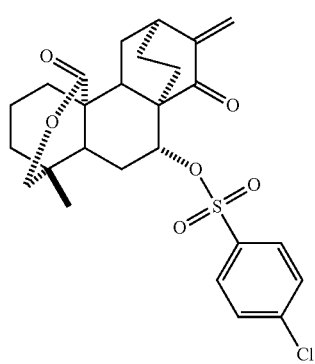
(1t)
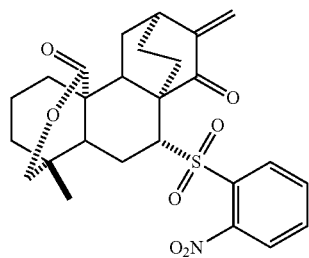
(1u)
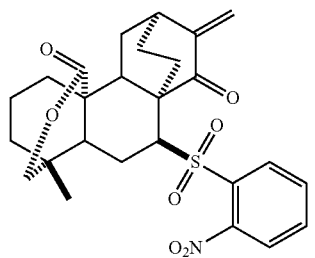
(1v)
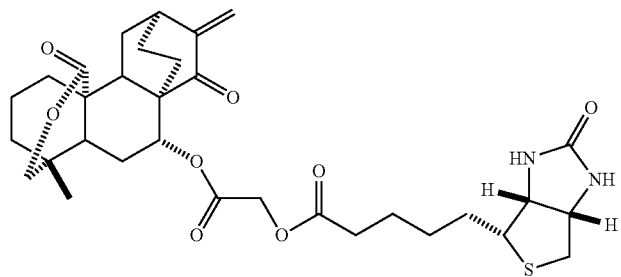
6
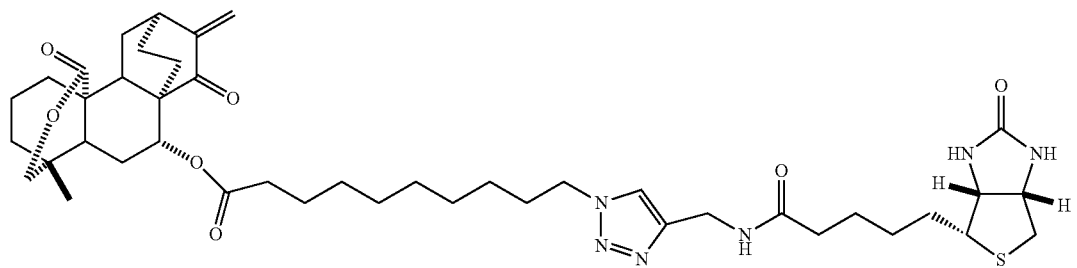
5

-continued
(7)
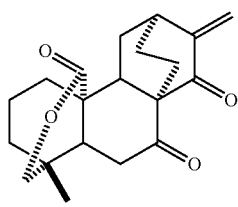
(8)
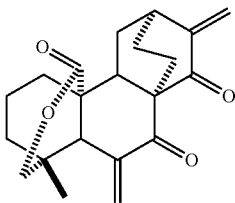
(9)
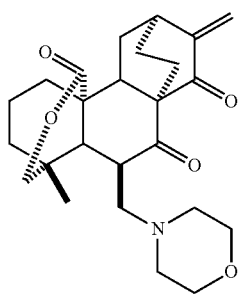
(10)
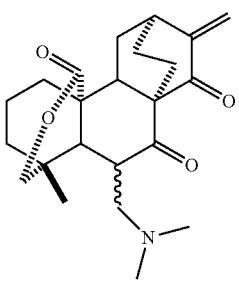
(11)
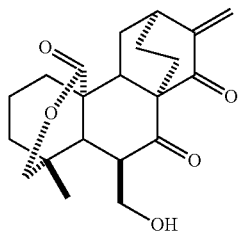
(12)
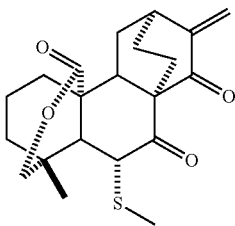
(13)
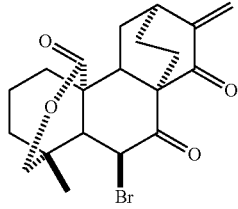
(14)
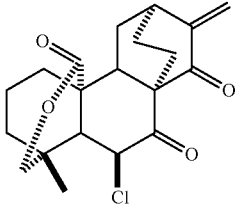
(15)
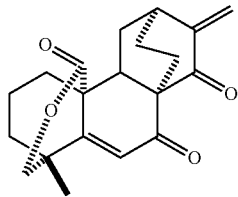
(16)
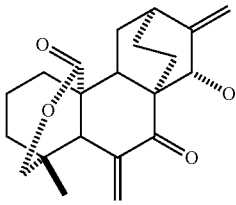
(21)
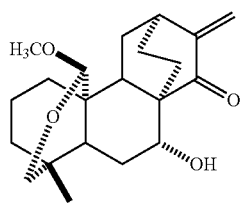
(22)
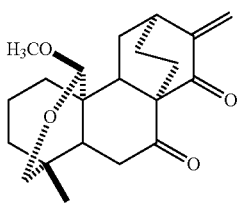
(23)
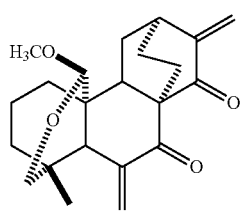
(25)
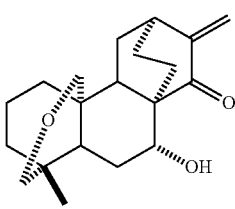

-continued
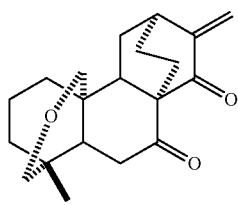
(28)
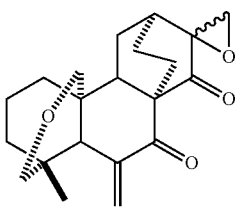
(29)
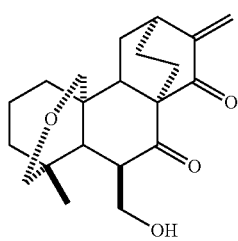
(30)
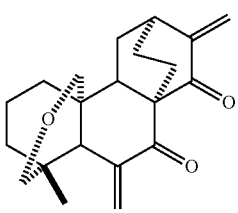
(31)
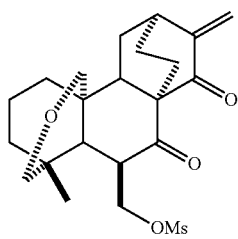
(32)
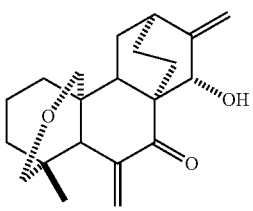
(33)
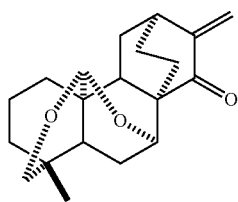
(36)
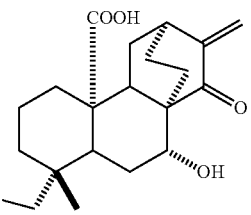
(38)
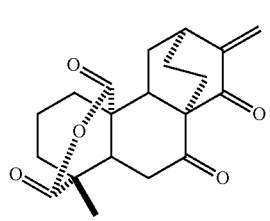
(39)
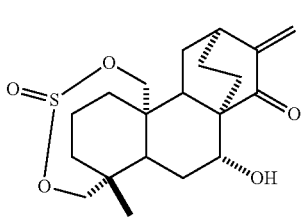
(41)
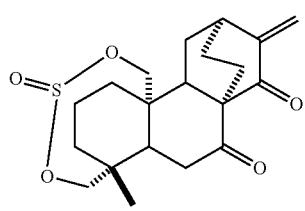
(42)
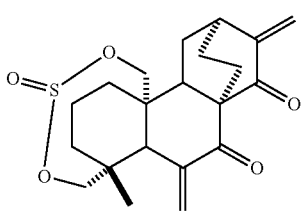
(43)
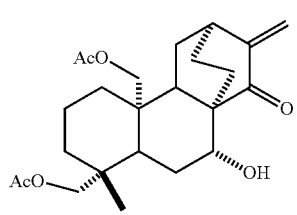
(45)
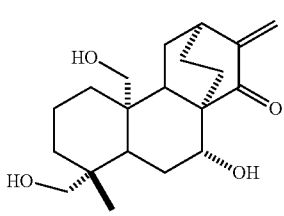
(46)

-continued
(47)
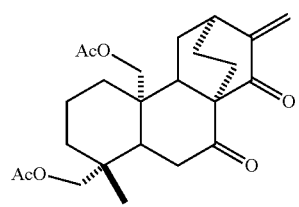
(48)
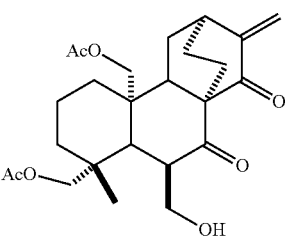
(49)
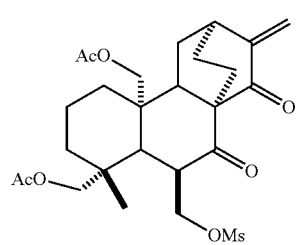
(50)
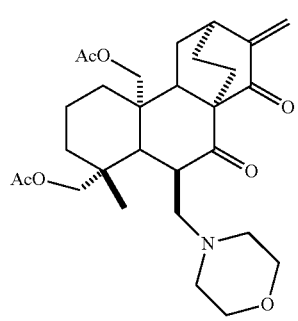
(51)
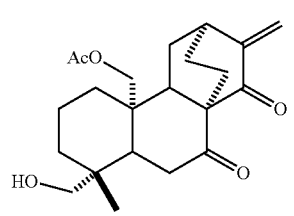
(52)
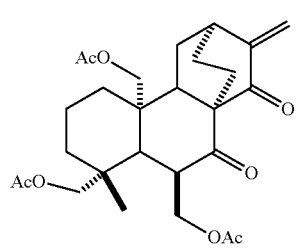
(53)
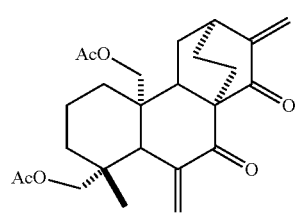
(55)
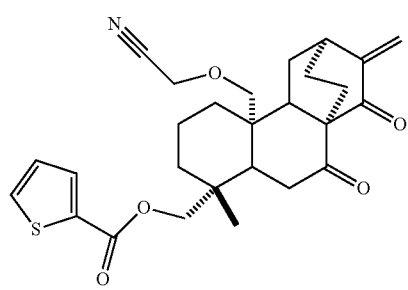
(59)
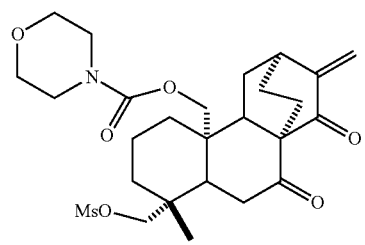
(61)
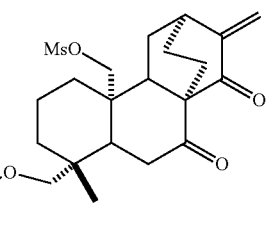
(63)
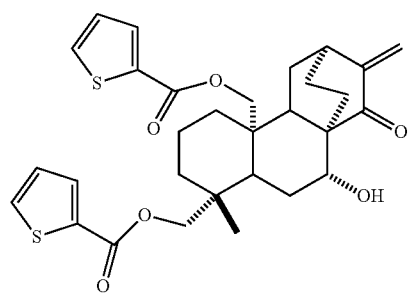
(64)
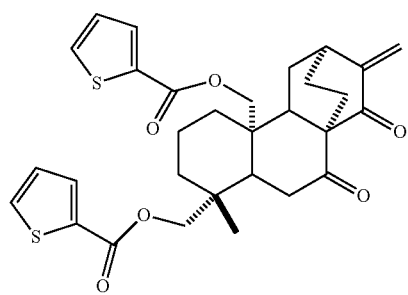

-continued
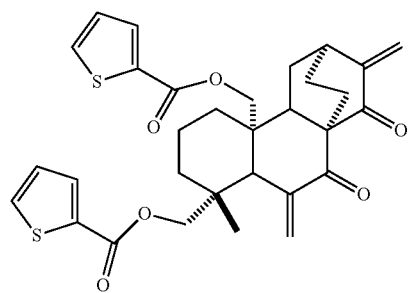
(65)
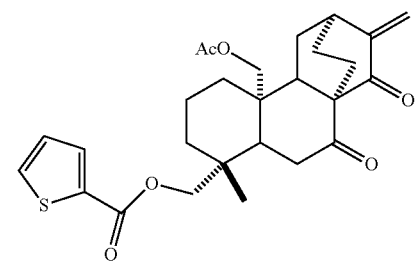
(66)
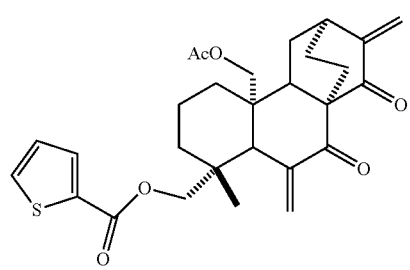
(67)
(70)
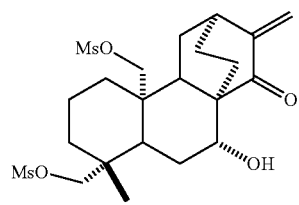
(72a)
(73a)
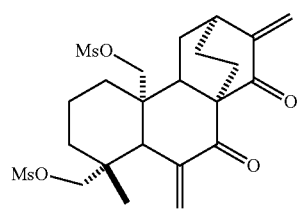
(74a)
(72b)
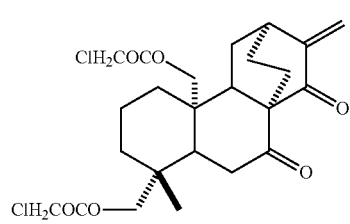
(73b)
(74b)
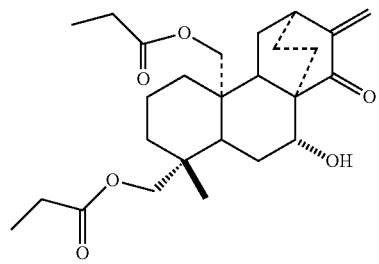
(72c)
(73c)

-continued
(74c) 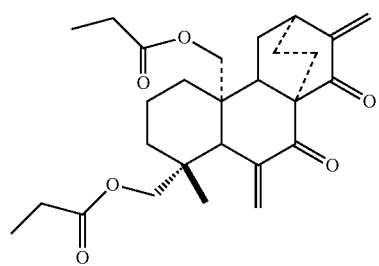
(72d) 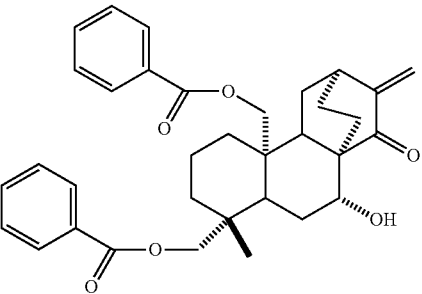
(73d) 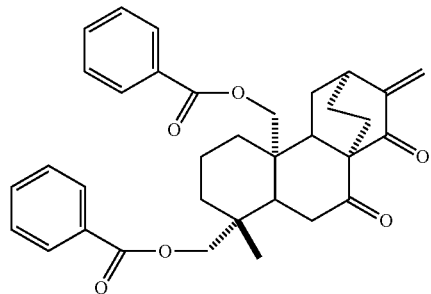
(74d) 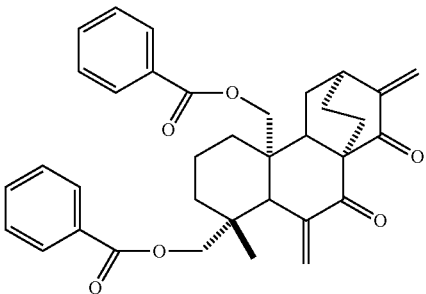
(72e) 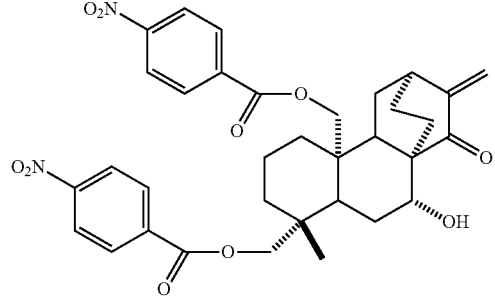
(73e) 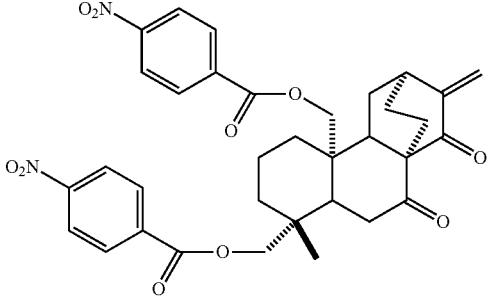
(74e) 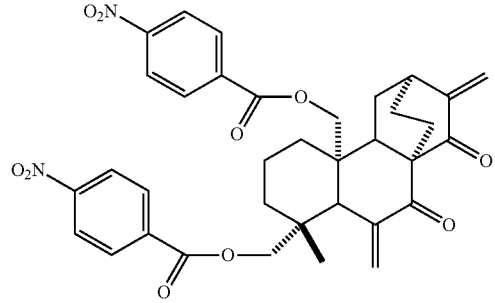
(75) 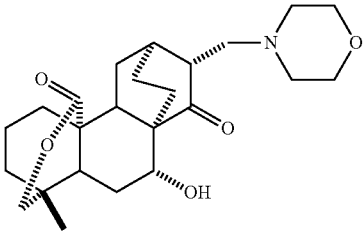
(76) 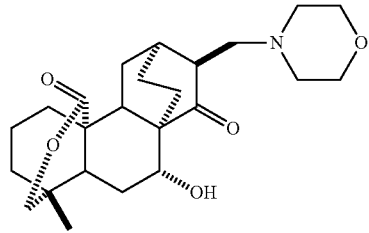
(77) 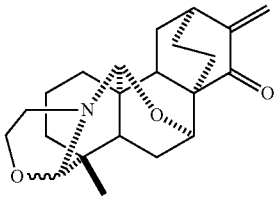

-continued
(78) 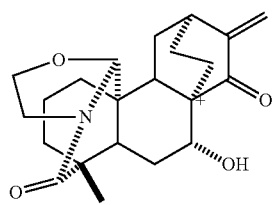
(80) 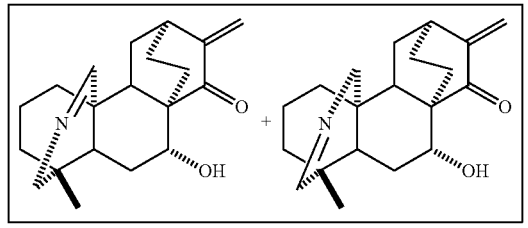
(82) 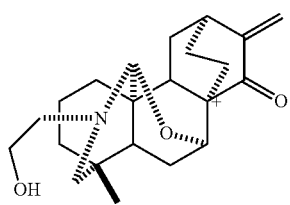
(83) 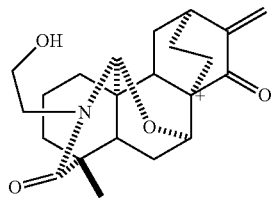
(84) 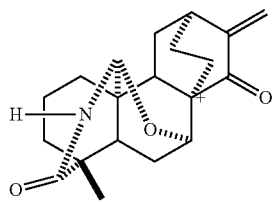
(88) 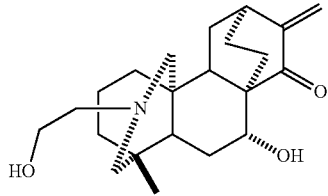
(89) 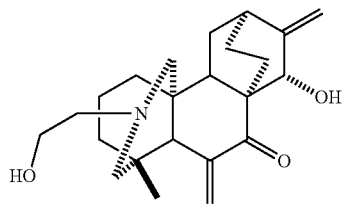
(91) 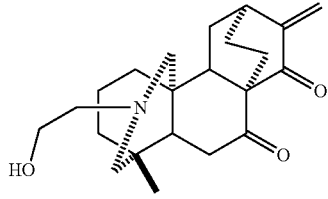
(92) 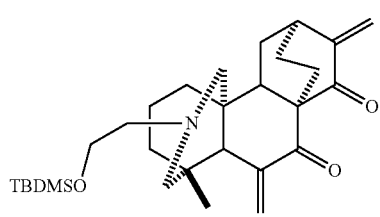
(93) 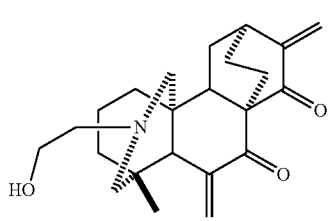

In the third aspect, the invention relates to a pharmaceutical composition, which comprises a therapeutically effective amount of one or more of the compound, isomer, solvate or pharmaceutically acceptable salt thereof according to any item of the first aspect or the second aspect of the invention, and a pharmaceutically acceptable carrier or adjuvant.

In the fourth aspect, the invention relates to a method for preparing the compound according to any item of the first aspect or the second aspect of the invention, comprising any of the following steps:

(1) Preparation of Acylated Derivatives of 15-Oxospiramilactone on 7-Hydroxyl:

Scheme 1

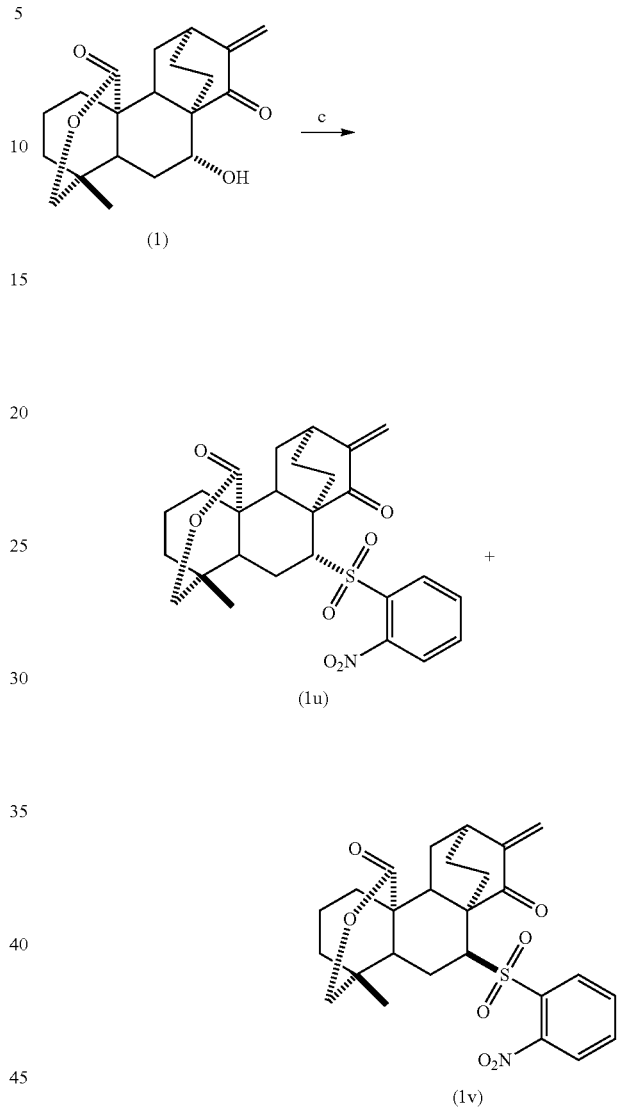

b R = acetyl          c R = 2-chloroacetyl
d R = 2-Bromoacetyl   e R = 2-azidoacetyl    f R = trifluoroacetyl
g R = acryloyl        h R = 3-chloropropionyl  i R = 2-chloropropionyl
j R = benzoyl         k R = 4-nitrobenzoyl    l R = 4-methoxybenzoyl
m R = 4-(trifluoromethyl)benzoyl              n R = 2-furanylcarbonyl
o R = 2-thiophenecarbonyl                     r R = 3-Phenyl-2-propenoyl
q R = methylsulfonyl  r R = phenylmethanesulfonyl
s R = benzenesulfonyl t R = 4-chlorobenzenesulfonyl Reagents and conditions: (a) (COCl)$_2$, DMF, DCM, 0° C. to r.m. (b) RCl, DMAP, Pyridine, 0° C. to r.m. or reflux, 90-100%, (c) 2-Nitrobenzoyl chloride, DMAP, Pyridine, 0° C. to r.m. to reflux, 20%;

(2) Preparation of Compound 5

Scheme 2

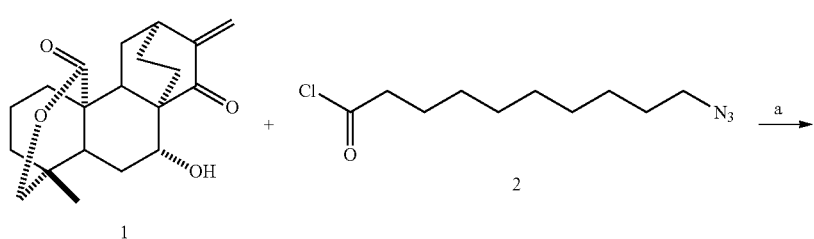

-continued
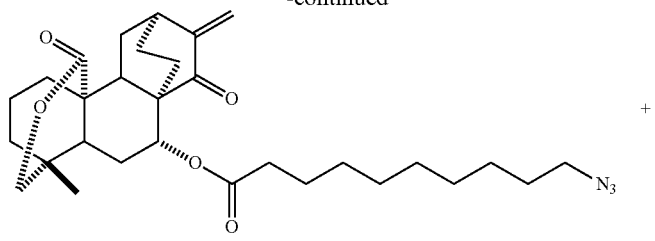
3
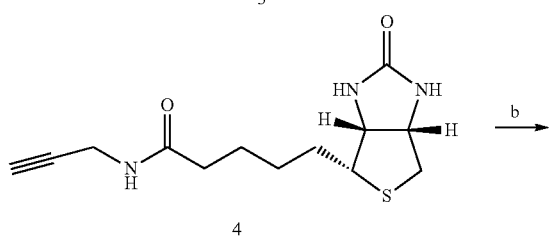
4
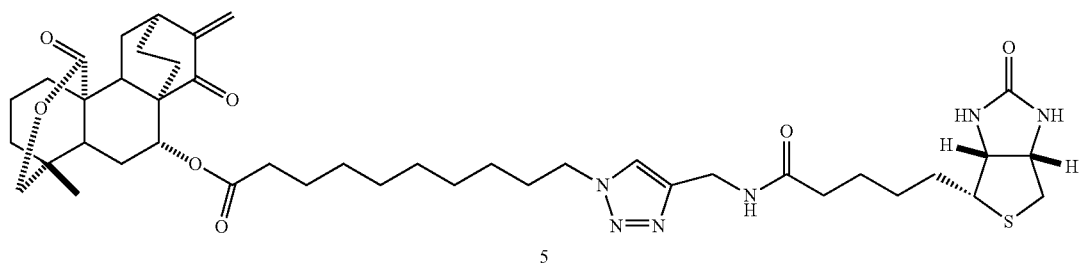
5
Reagents and conditions: (a) DMAP, Pyridine, 0° C. to r.m., DCM; (b) CuSO₄, Sodium Vc, H₂O, EtOH;
(3) Preparation of Compound 6:
Scheme 3
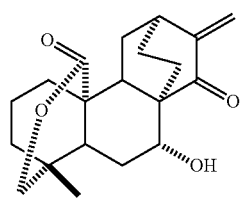
S-3
a →
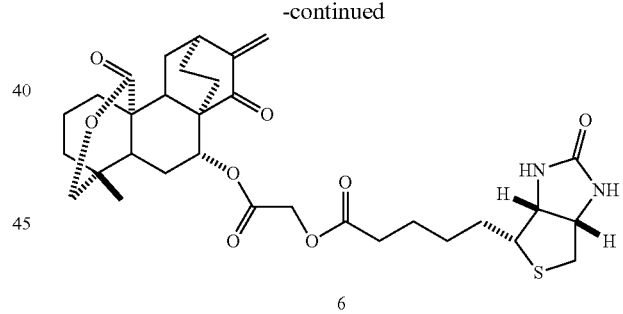
6
Reagents and conditions: (a) Chloroacetyl chloride, DMAP, Pyridine, r.m., DCM; (b) Biotin, CsCl, NaHCO₃, 70° C.;
(4) Preparation of Compound 16:
Scheme 4
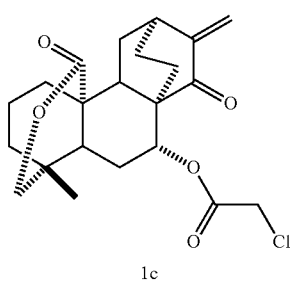
1c
b →
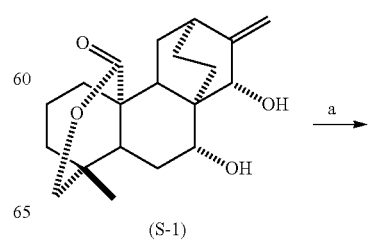
(S-1)
a →

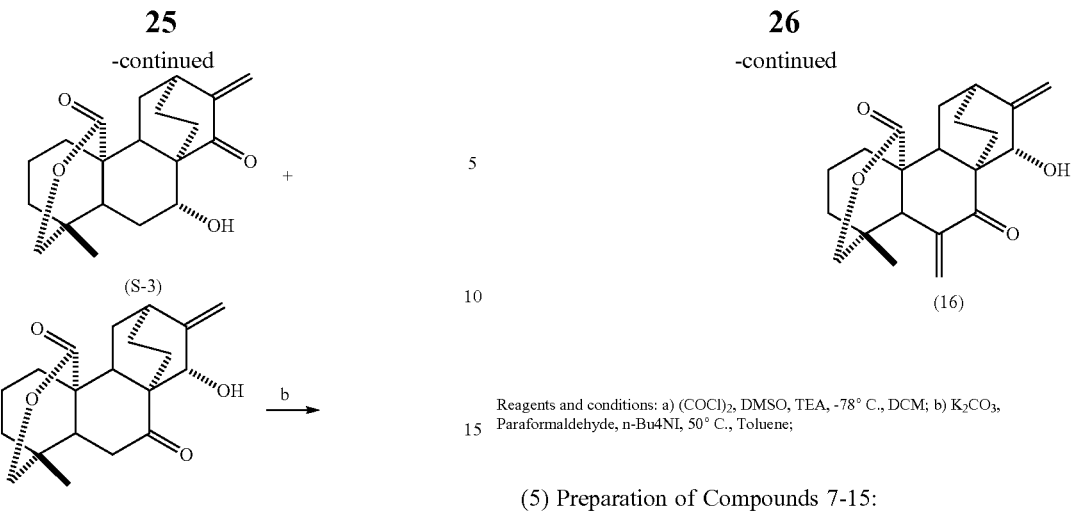
Reagents and conditions: a) (COCl)₂, DMSO, TEA, -78° C., DCM; b) K₂CO₃, Paraformaldehyde, n-Bu4NI, 50° C., Toluene;
(5) Preparation of Compounds 7-15:
Scheme 5
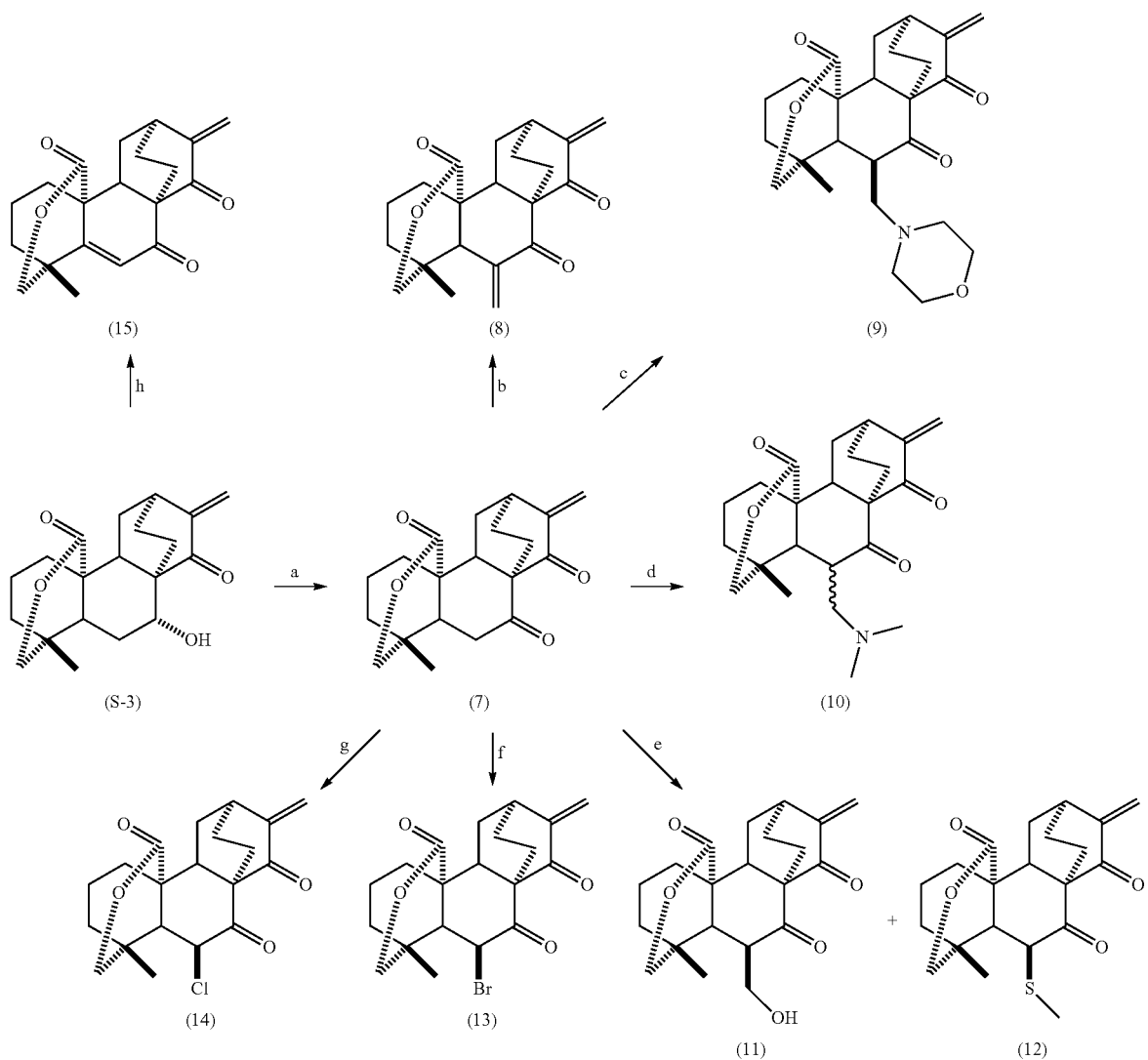
Reagents and conditions: a) (COCl)₂, DMSO, TEA, -78° C., DCM; b) K₂CO₃, (HCHO)ₙ, n-Bu4NI, 50° C., Toluene; c) (HCHO)ₙ, Morpholine, AcOH, Toluene, d) (HCHO)ₙ, Me₂NH·HCl, AcOH, Toluene; e) DMSO, NCS, 45° C.; f) DMSO, NBS, 45° C.; g) NCS, (BMIM)PF₄; h) IBX, 70° C., Toluene, DMSO = 2:1;

(6) Preparation of Compounds 21, 22, 23
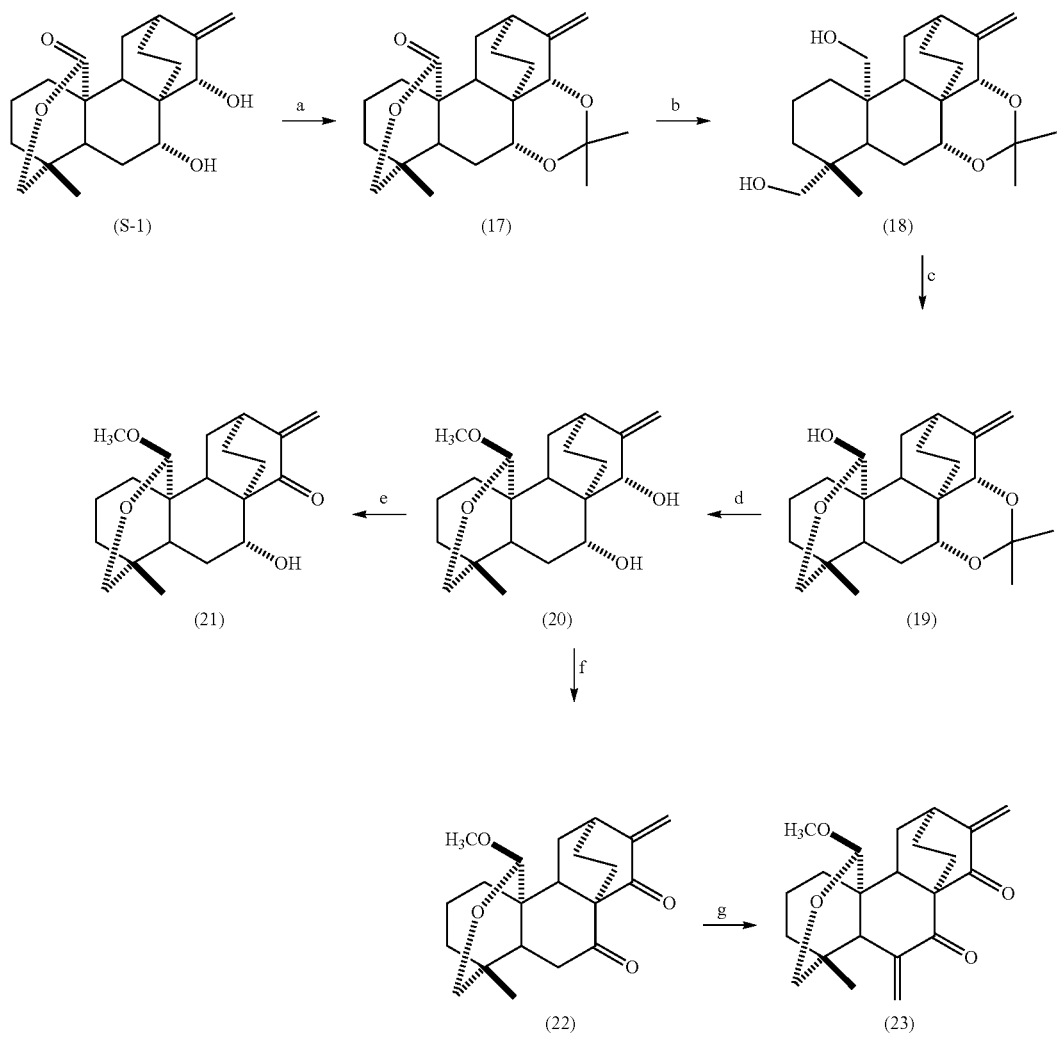
Reagents and conditions: a) Toluene-4-sulfonic acid, Acetone; b) LiAlH₄, THF, 45° C.; c) PDC, DCM; d) 2N HCl, MeOH; e) MnO₂, DCM; f) (COCl)₂, DMSO, TEA, -78° C., DCM; g) K₂CO₃, (HCHO)ₙ, n-BuNI, 50° C., Toluene;
(7) Preparation of Compounds 25-33
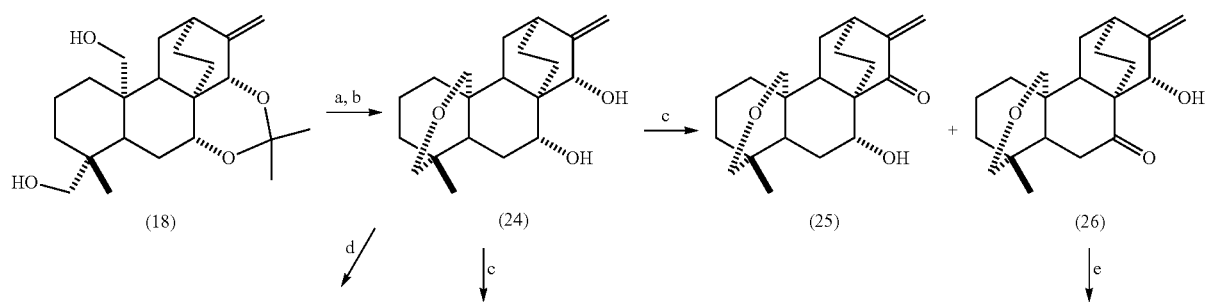

-continued
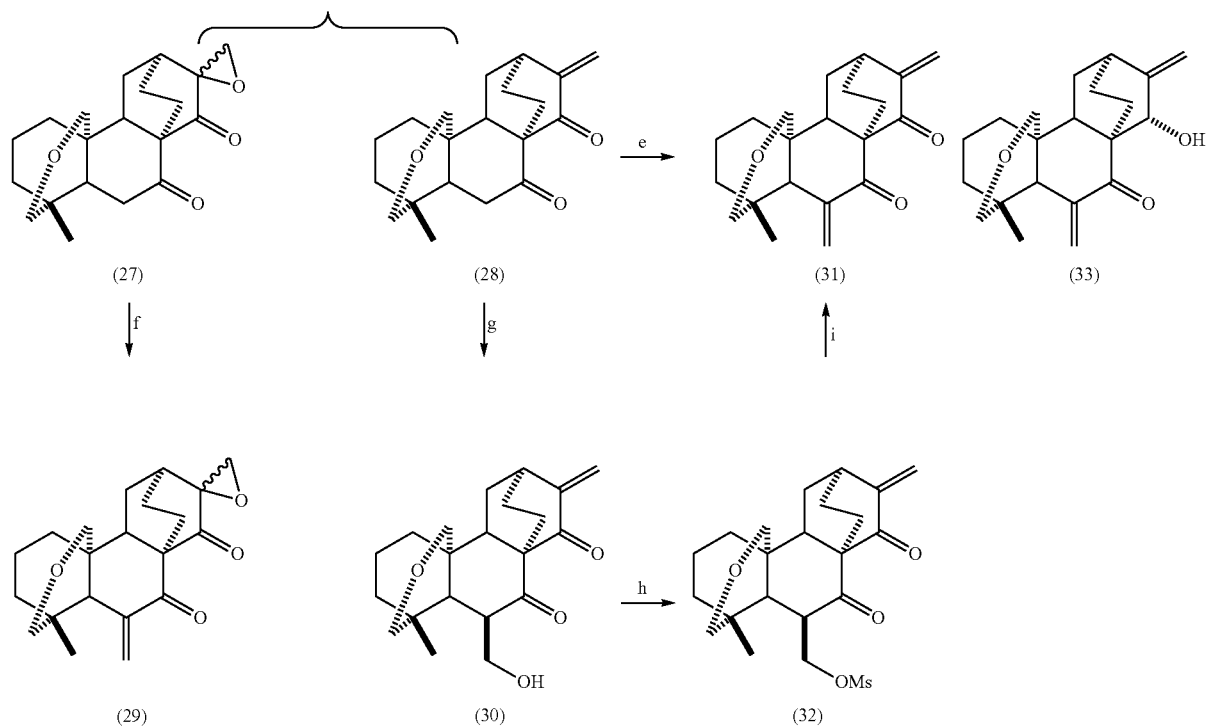
Reagents and conditions:
a) PPh₃, DIAD, THF;
b) 2N HCl, MeOH;
c) (COCl)₂, DMSO, TEA, -78° C., DCM;
d) Jone's reagent, 0° C., Acetone;
e) K₂CO₃, (HCHO)ₙ, n-Bu₄NI, 50° C., Toluene;
f) (HCHO)ₙ, Morpholine, AcOH, (BMIM)PF₄, 70° C.;
g) K₂CO₃, (HCHO)ₙ, Toluene;
h) MsCl, DMAP, Pyridine, DCM;
i) DBU, THF.
(8) Preparation of Compound 36
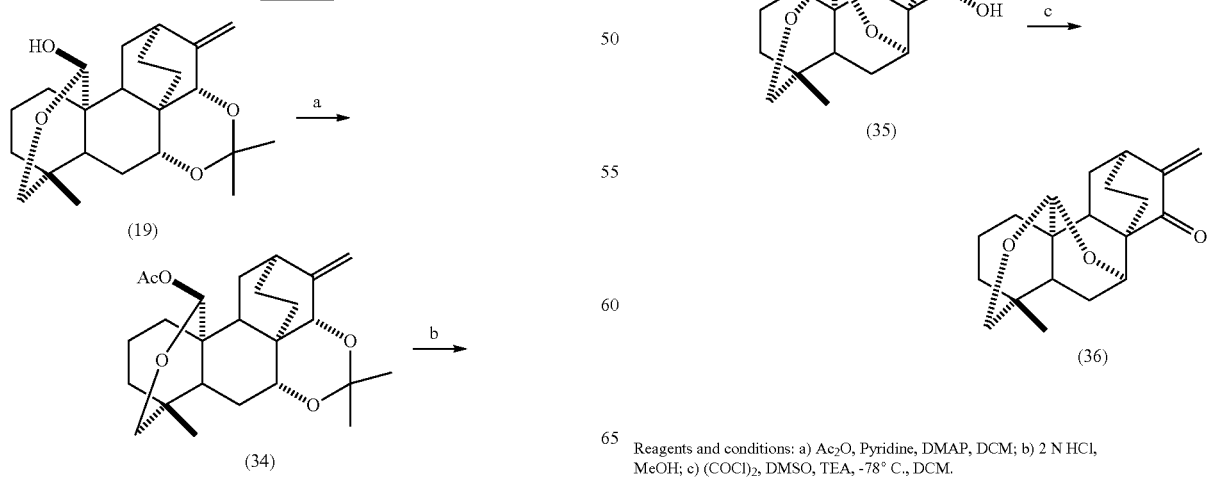
Reagents and conditions: a) Ac₂O, Pyridine, DMAP, DCM; b) 2 N HCl, MeOH; c) (COCl)₂, DMSO, TEA, -78° C., DCM.

(9) Preparation of Compounds 38, 39
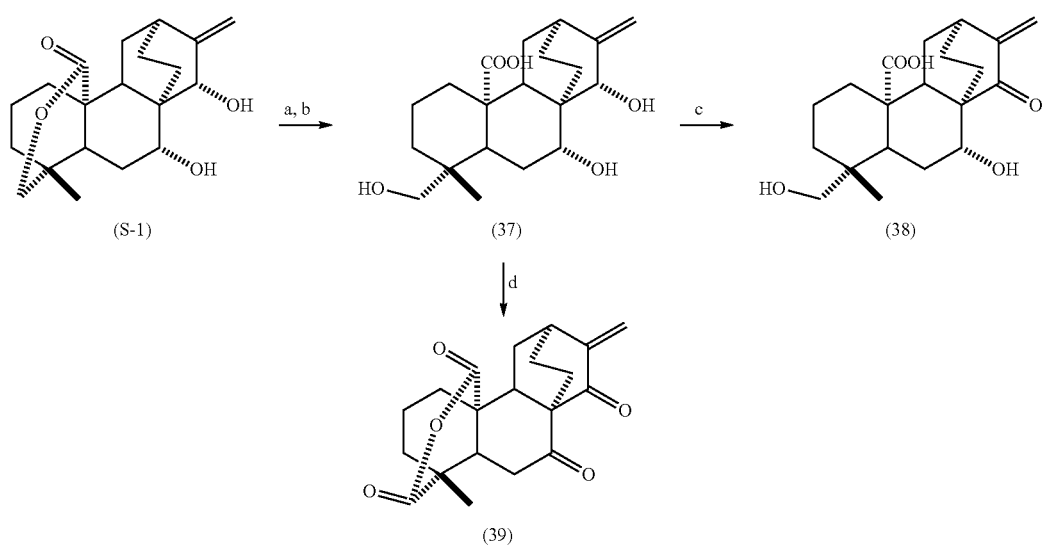
Reagents and conditions: a) KOH, MeOH, 80° C.; b) 2 N HCl; c) MnO₂, DCM; d) Jone's reagent, 0° C., Acetone;
(10) Preparation of Compounds 41-53
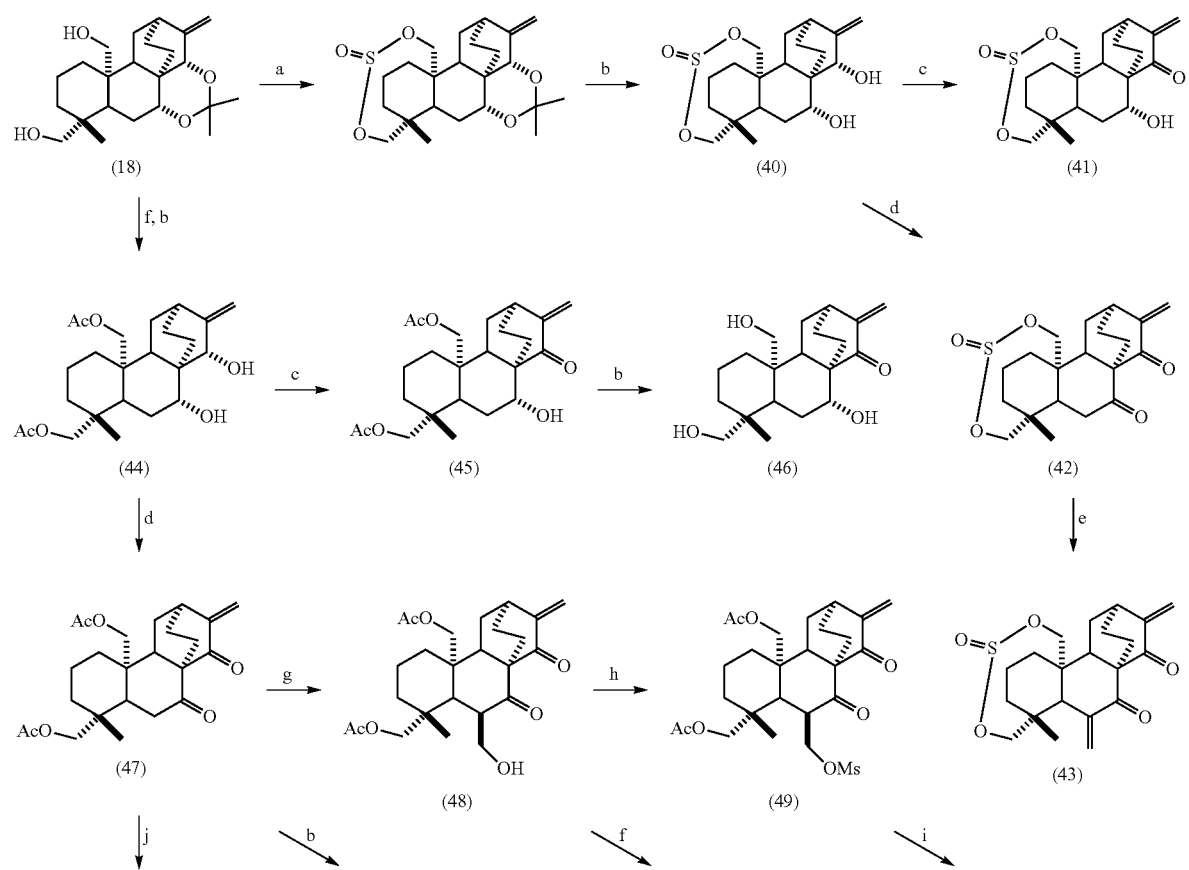

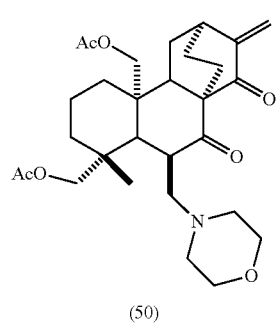

(50)

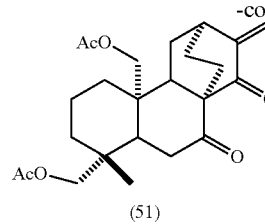

(51)

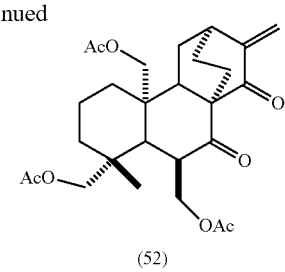

(52)

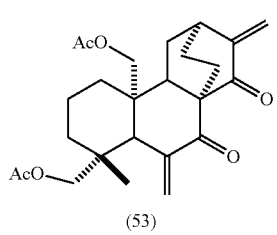

(53)

Reagents and conditions: a) SOCl₂, Pyridine, 0° C., DCM; b) 2 N HCl, THF; c) MnO₂, DCM; d) (COCl)₂, DMSO, TEA, -78° C., DCM; e) K₂CO₃, (HCHO)$_n$, n-Bu₄NI, 50° C., Toluene; f) Ac₂O, Pyridine, DMAP, DCM, r.m.; g) K₂CO₃, (HCHO)$_n$, Toluene; h) MsCl, DMAP, Pyridine, DCM; i) DBU, THF; j) (HCHO)$_n$, Morpholine, AcOH, Toluene.

(11) Preparation of Compounds 55, 59, 61

Scheme 11

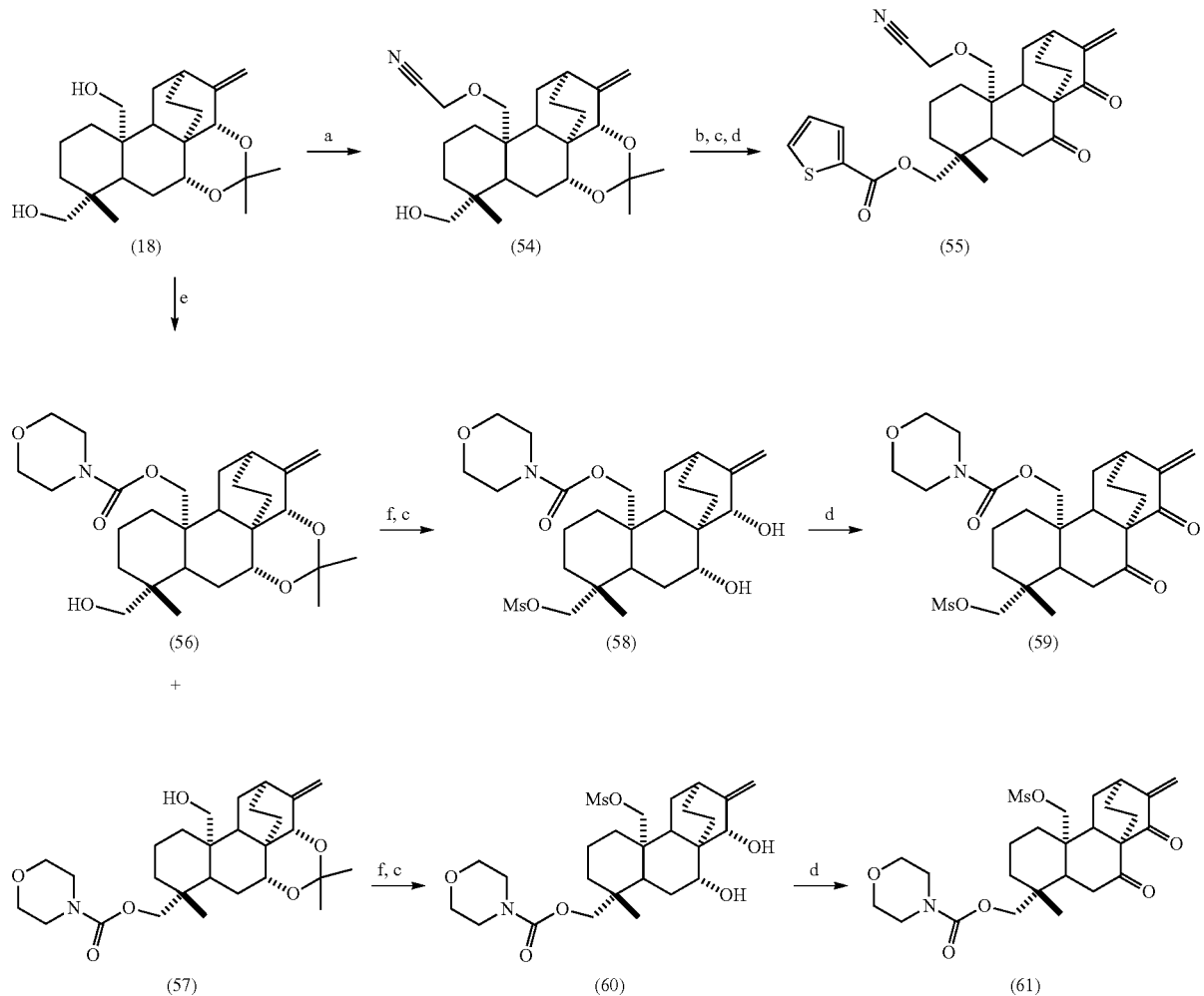

Reagents and conditions: a) NaH, Bromoacetonitrile, DMF, 0° C.; b) 2-Thiophenecarbonylchloride, DMAP, Pyridine, DCM, 40° C.; c) 2 N HCl, THF; d) (COCl)₂, DMSO, TEA, -78° C.; e) NaH, 4-Morpholinecarbonyl chlorid, THF, 0° C.; f) MsCl, DMAP, Pyridine;

(12) Preparation of Compounds 63-67
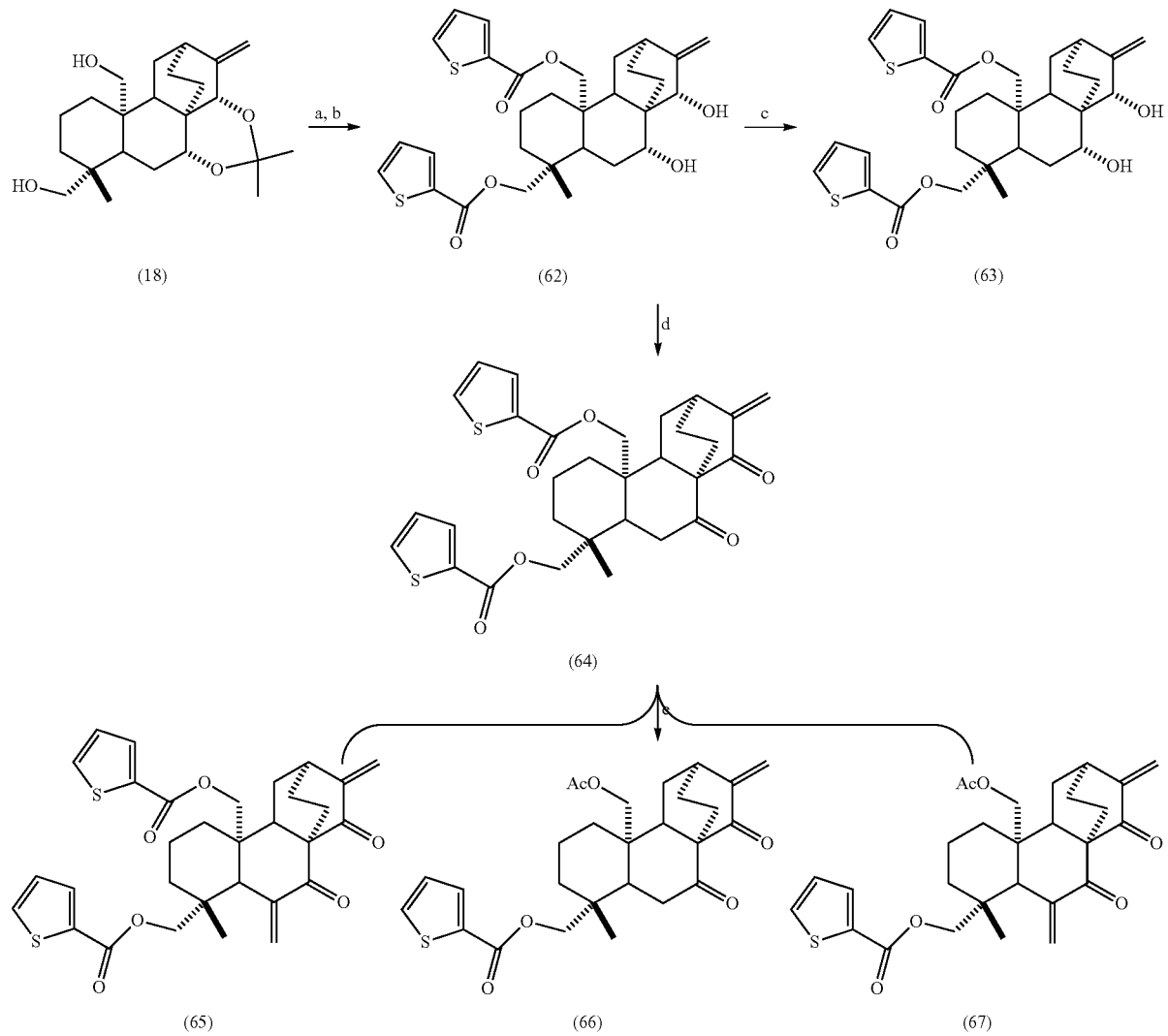
Reagents and conditions:
a) 2-Thiophenecarbonylchloride, DMAP, Pyridine, DCM, 40° C.;
b) 2N HCl, THF;
c) MnO₂, DCM;
d) (COCl)₂, DMSO, TEA, -78° C.;
e) (HCHO)ₙ, Morpholine, AcOH, (BMIM)PF₄, 70° C.
(13) Preparation of Compound 70
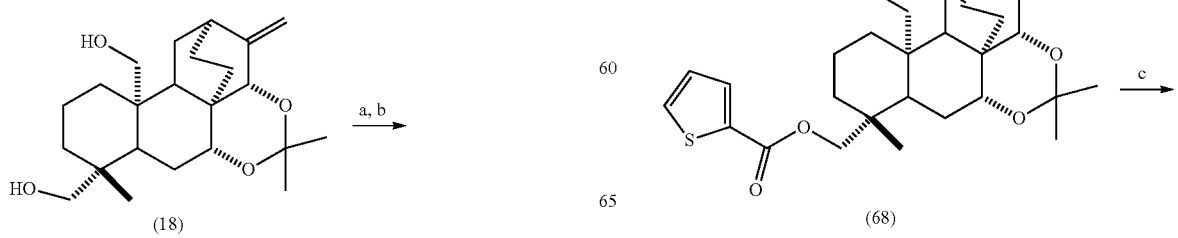

-continued

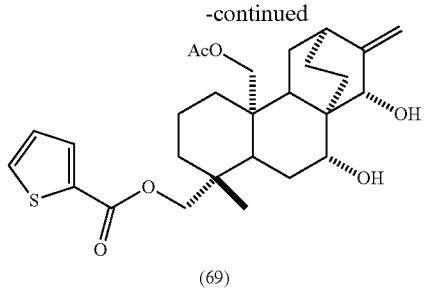

(69)

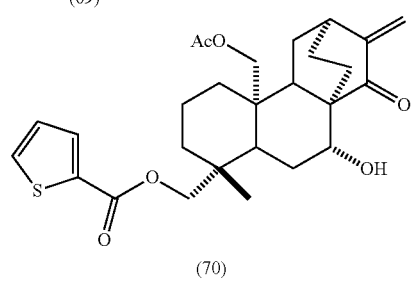

(70)

Reagents and conditions: a) 2-Thiophenecarbonylchloride, DMAP, Pyridine, DCM, r.m.; b) Ac₂O, Pyridine, DMAP, DCM, r.m. c) 2 N HCl, THF; d) MnO₂, DCM; e) (COCl)₂, DMSO, TEA, -78° C.; f) K₂CO₃, (HCHO)$_n$, Toluene.

(14) Preparation of Compounds (72a-72e), (73a-73e) and (74a-74e)

(15) Preparation of Compounds (75), (76)

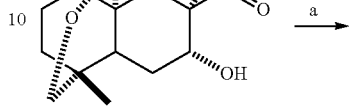

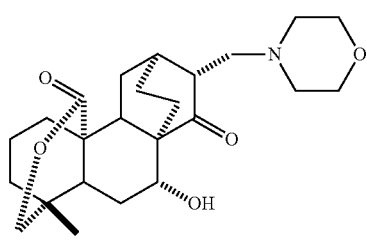

(75, S-417a)

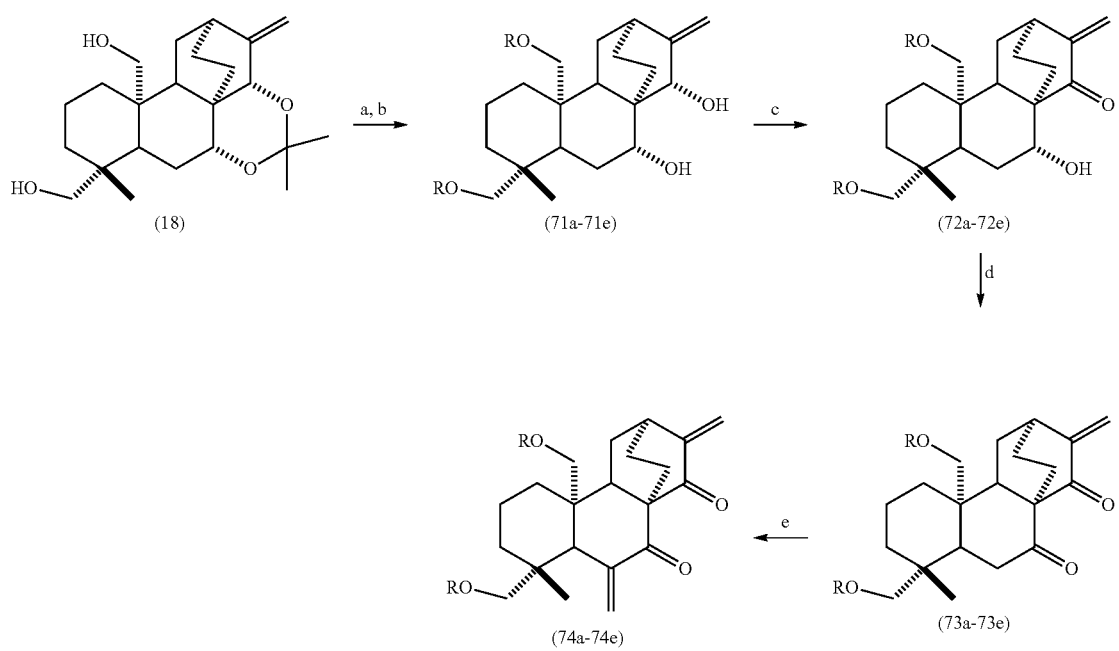

a R = methylsulfonyl
b R = 2-chloroacetyl
c R = propionyl
d R = benzoyl
e R = 4-nitrobenzoyl Reagents and conditions: a) RCl, DMAP, Pyridine, 0° C. to r.m. or reflux; b) 2 N HCl, THF; c) MnO₂, DCM; d) (COCl)₂, DMSO, TEA, -78° C.; e) K₂CO₃, (HCHO)$_n$, Toluene.

-continued
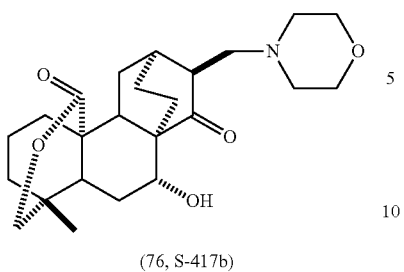
(76, S-417b)
Reagents and conditions: a) Morpholine, MeOH, r.m.;
(16) Preparation of Compounds 77-84
Scheme 16
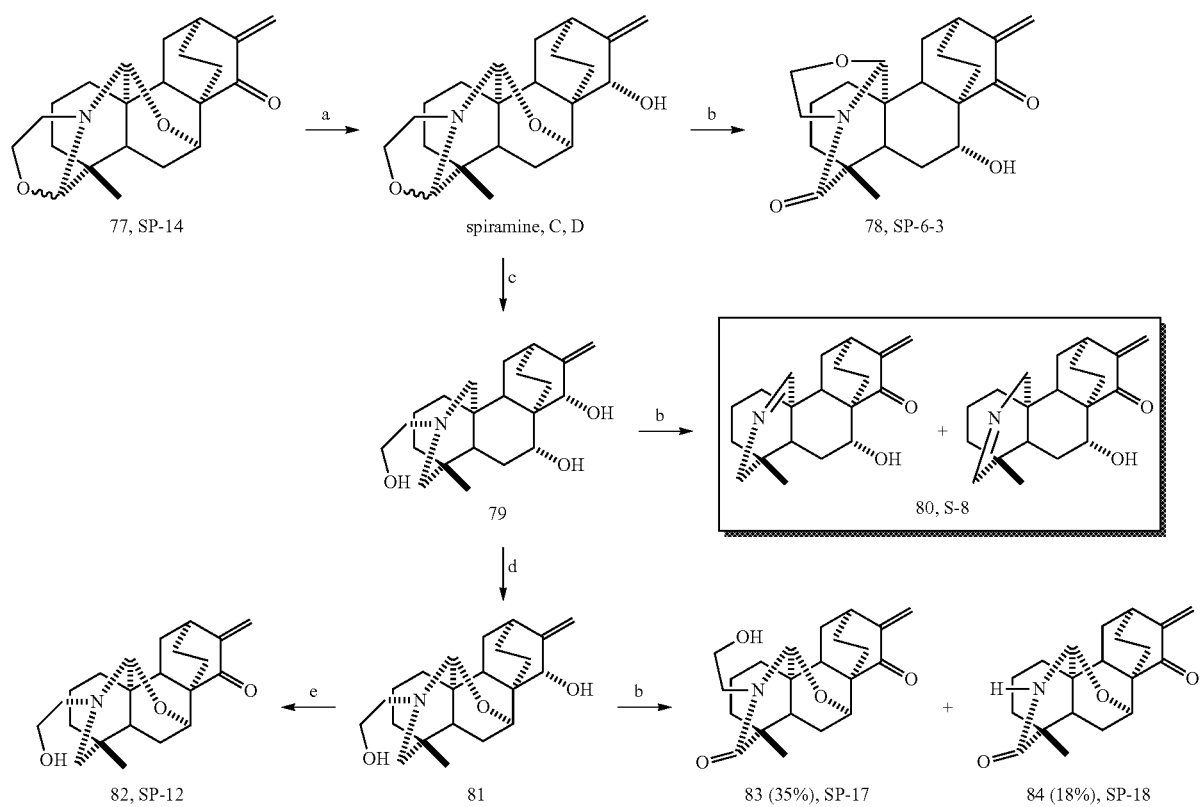
Reagents and conditions: a) (COCl)$_2$, DMSO, TEA, DCM, -78° C., 96%; b) MnO$_2$, 30.0eq., 72 h, Acetone, r.t.; c) NaBH$_4$, MeOH, r.t., 98%; d) K$_3$Fe(CN)$_6$, KOH, MeOH, 75° C., 71%; e) MnO$_2$, 5.0 eq., 72 h, Acetone, r.t.
(17) Preparation of Compounds 88-91
Scheme 17
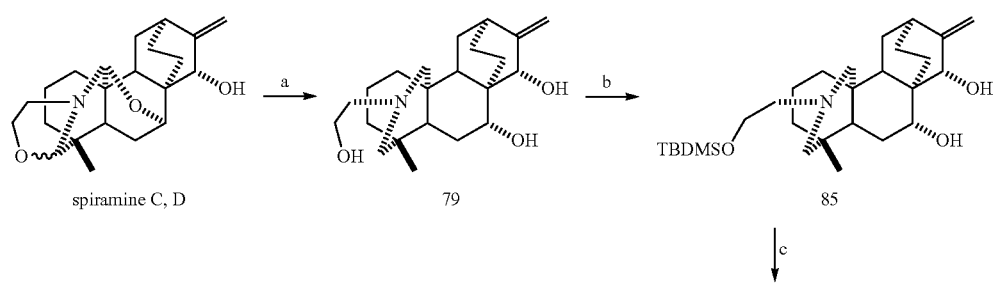

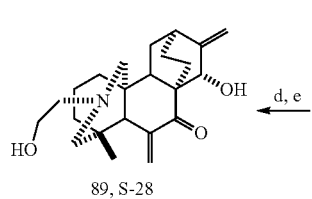
89, S-28

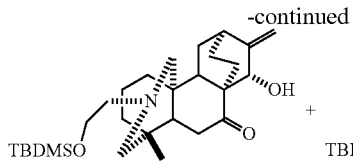
86 (20%)

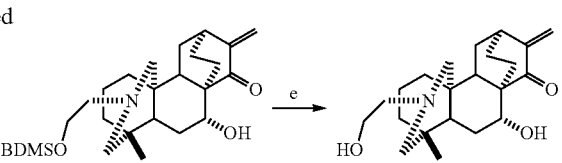
87 (16.8%) → 88, S-27

(86 + 87, 53.7%)

95% ↓ c

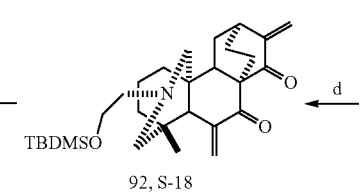
93, S-19 ← 92, S-18

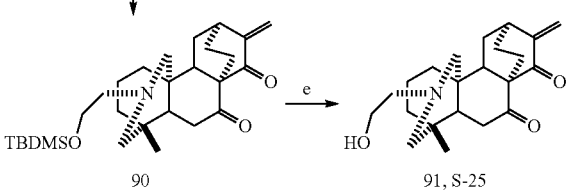
90 → 91, S-25

Reagents and conditions:
a) NaBH$_4$, MeOH, r.t., 98%;
b) TBDMSCl, Imidazole, 3 h, DMF, 90%;
c) (COCl)$_2$, DMSO, TEA, DCM, -78° C.;
d) (HCHO)$_n$, n-Bu$_4$NI, K$_2$CO$_3$, toluene, 50° C., 24 h;
e) TBAF, THF, 3 h, r.t.

In the fifth aspect, the invention relates to use of the compound, or the isomer, solvate or pharmaceutically acceptable salt thereof according to any item of the first aspect or the second aspect of the invention in manufacture of an anti-tumor agent.

In the sixth aspect, the invention relates to use of the compound, or the isomer, solvate or pharmaceutically acceptable salt thereof according to any one of the first aspect or the second aspect of the invention in manufacture of a medicament for preventing or treating a disease or disorder caused by abnormal inactivation of the canonical Wnt signaling pathway.

The use according to any item of the sixth aspect of the invention, wherein the disease or disorder caused by abnormal inactivation of the canonical Wnt signaling pathway includes, but is not limited to senile dementia (Alzheimer's disease), rheumatic arthritis, osteoporosis, cancer, and zebrafish development disorder.

In the seventh aspect, the invention relates to use of the compound, or the isomer, solvate or pharmaceutically acceptable salt thereof according to any item of the first aspect or the second aspect of the invention in manufacture of a medicament as a Wnt inhibitor.

The invention further relates to a method for preventing or treating tumor, comprising the step of administering the compound, or the isomer, solvate or pharmaceutically acceptable salt thereof according to any item of the first aspect or the second aspect of the invention to a subject in need thereof.

The invention further relates to a method for preventing or treating a disease or disorder caused by abnormal inactivation of the canonical Wnt signaling pathway, comprising the step of administering the compound, or the isomer, solvate or pharmaceutically acceptable salt thereof according to any item of the first aspect or the second aspect of the invention to a subject in need thereof.

In the invention, the disease or disorder caused by abnormal inactivation of the canonical Wnt signaling pathway includes, but is not limited to senile dementia (Alzheimer's disease), rheumatic arthritis, osteoporosis, cancer, and zebrafish development disorder.

In the invention, the halogen refers to fluorine, chlorine, bromine, or iodine.

In the invention, the $C_{1-6}$alkyl refers to a linear, branched, or cyclic alkyl having 1-6 (e.g., 1-3) carbon atoms, including, but is not limited to methyl, ethyl, n-propyl, isopropyl, n-butyl, sec-butyl, isobutyl, tert-butyl, pentyl, neo-pentyl, hexyl, cyclopropyl, cyclobutyl, cyclopentyl, cyclohexyl, etc.

In the invention, the $C_{2-6}$alkenyl refers to an alkenyl having 2-6 carbon atoms and at least one double bond, including, but is not limited to vinyl, propenyl, 1-buten-3-yl, 1-penten-3-yl, 1-hexen-5-yl, etc.

In the invention, the $C_{1-6}$alkylacyloxy refers to $C_{1-6}$alkyl-CO—O—, wherein $C_{1-6}$alkyl is as described above.

In the invention, the $C_{1-6}$alkoxy refers to $C_{1-6}$alkyl-O—, wherein $C_{1-6}$alkyl is as described above.

In the invention, the $C_{1-6}$alkylsulfonyloxy refers to $C_{1-6}$alkyl-SO$_2$—O—, wherein $C_{1-6}$alkyl is as described above.

In the invention, the $C_{1-6}$alkylacyl refers to $C_{1-6}$alkyl-CO—, wherein $C_{1-6}$alkyl is as described above.

In the invention, the $C_{1-6}$alkylsulfonyl refers to $C_{1-6}$alkyl-SO$_2$—, wherein $C_{1-6}$alkyl is as described above.

In the invention, the aryl includes, but is not limited to phenyl and naphthyl.

In the invention, the N-containing 5-membered ring includes, but is not limited to pyrrolidine ring, oxazole ring, isoxazole ring, thiazole ring, and isothiazole ring.

In the invention, the N-containing 6-membered ring includes, but is not limited to morpholine ring, piperidine ring, thiomorpholine ring, and 1, 3-oxazinane ring.

In Formula I of the invention, when ═ represents a double bond, the structure of Formula I

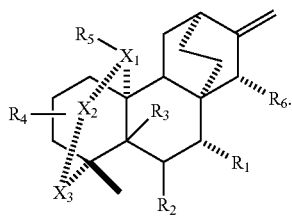

In Formula I of the invention, when ═ represents a single bond, and R₇ is further linked to the C atom on the ring via an oxo bridge, the structure of Formula I is

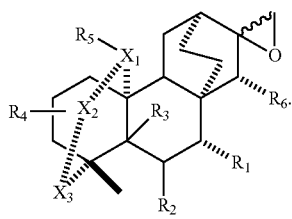

In Formula II of the invention, when ═ represents a double bond, the structure of Formula I is

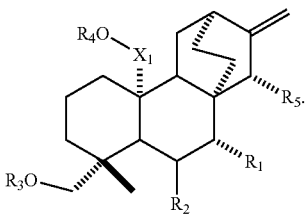

In Formula II of the invention, when ═ represents a single bond, and R₆ is further linked to the C atom on the ring via an oxo bridge, the structure of Formula I is

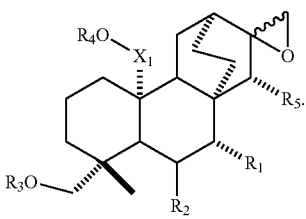

According to the invention, the invention relates to a suitable pharmaceutically acceptable salt or hydrate of the compound of Formula I or II or the stereoisomer thereof, wherein the pharmaceutically acceptable salt includes, but is not limited to the salts formed with inorganic acids, such as hydrochloric acid, sulphuric acid, phosphoric acid, phosphorous acid, hydrobromic acid and nitric acid; and the salts formed with various organic acids, such as maleic acid, malic acid, fumaric acid, succinic acid, tartaric acid, citric acid, acetic acid, lactic acid, methanesulfonic acid, p-toluene sulfonic acid, palmitic acid, etc. Certain compounds of the invention may be crystallized or re-crystallized in water or various organic solvents. In this case, a variety of solvates may be formed. The invention includes the stoichiometric solvates, including not only hydrates, but also the compound containing a variable amount of water prepared by a drying method using sublimation at low pressure.

According to the invention, certain compounds of the invention may exist in a form of optical isomer or tautomer, thus the stereoisomer of the compound of Formula I or II includes all its existing forms, particularly the form of pure isomer. Isomers in different forms may be separated or resolved from those in other forms by various conventional means, or a certain isomer may be obtained by various conventional synthetic methods, or stereospecific or asymmetric synthetic methods. Since the compound of Formula I or II is used for pharmaceutical purpose, it may be understood that the compound is most preferably provided in a pure form, e.g., with a purity of at least 60%, more suitably a purity of 75%, more preferably a purity of 85%, and most preferably a purity of at least 98% (% refers to percentage by weight). Method for preparing impure compound can be applied in the preparation of the compound in a more pure form in a pharmaceutical composition. The impure compound comprises at least 1%, more suitably 5%, more preferably 10% of the compound of Formula I or II or a pharmaceutically acceptable derivative thereof.

When the compound of the invention is used as a medicament, it may be used directly, or in a form of a pharmaceutical composition. The pharmaceutical composition comprises 0.1-99.5%, preferably 0.5-90% of the compound of the invention, the rest is a pharmaceutically acceptable, inert carrier and/or excipient that is not toxic to human and animal.

The pharmaceutically acceptable carrier or excipient is one or more solids, semisolids, and liquid diluent agents, fillers and adjuvants for pharmaceutical preparations. The pharmaceutical composition of the invention is used in a dosage for unit body weight. The composition of the invention may be prepared, by methods well known in the field of medicine and food, in a variety of forms, such as liquid formulation (injection, suspension, emulsion, solution, syrup, etc.), solid formulation (tablet, capsule, granule, medicinal instant granule, etc.), spray, aerosol, and so on. The medicament of the invention may be administered by routes such as injection (intravenous injection, intravenously drip, intramuscular injection, intraperitoneal injection, subcutaneous injection), oral route, sublingual route, mucosal dialysis, etc., for the treatment of tumor.

The pharmaceutically acceptable carrier comprised in the pharmaceutical composition of the invention includes, but is not limited to ion exchanger, aluminum oxide, aluminum stearate, lecithin, serum protein such as human serum protein; buffer substance such as phosphate, glycerol, sorbic acid, potassium sorbate, a partial glyceride mixture of saturated plant fatty acid, water, salt, or electrolyte, such as protamine sulfate, disodium hydrogen phosphate, potassium hydrogen phosphate, sodium chloride, zinc salt, colloid silica, magnesium trisilicate, polyvinylpyrrolidone, cellulose substance, polyethylene glycol, carboxymethylcellulose sodium, polyacrylic ester, beewax, lanocerin and the like. The amount of a carrier presented in a pharmaceutical composition is 1%~98% by weight, generally about 80% by weight. For the convenience of use, local anesthetics, preservatives, buffers and the like may be directly dissolved in the carrier.

Oral formulations such as oral tablets and capsules may comprise excipients such as binders, e.g., syrup, arabic gum, sorbitol, *Astragalus gummifer*, or polyvinylpyrrolidone; fillers, such as lactose, sucrose, corn starch, calcium phosphate, sorbitol, aminoacetic acid; lubricants, such as magnesium stearate, talc, polyethylene glycol, silica; disintegrants, such as potato starch; or acceptable humidizer, such as sodium lauryl sulfate. The tablet may be coated by methods well known in pharmacy.

The pharmaceutical composition of the invention in an oral liquid form may be prepared into a suspension of water and oil, a solution, an emulsion, a syrup or an elixir, or into a dry product, which is supplemented with water or other suitable medium prior to use. The liquid formulation may comprise conventional additives such as suspending agent, for example, sorbitol, methyl cellulose, glucose syrup, gel, hydroxyethyl cellulose, carboxymethyl cellulose, aluminum stearate gel, hydrogenated edible fat, emulsifier, for example, lecithin, sorbitan monooleate, gum arabic; or non-aqueous carrier (which may comprise edible oil), for example, almond oil, fat such as glycerol, ethylene glycol or ethanol; preservative, for example, methyl or propyl para-hydroxybenzoate, sorbic acid. If necessary, flavoring agents or coloring agents may be added. Suppositories may comprise conventional suppository bases, such as cocoa butter or other glycerides. For parenteral administration, a liquid formulation is generally prepared from the compound of the invention and at least one sterilized or aseptic carrier. Water is preferred for the carrier. Depending on the selected carrier and the concentration of a drug, the compound of the invention may be dissolved in the carrier or prepared into a suspension solution. For the preparation of a solution for injection, the compound of the invention is dissolved in water first, and packaged into a seal bottle or an ampoule after filtration and sterilization. When topically administered to skin, the compound of the invention may be prepared in a suitable form of ointments, lotions or creams, wherein the active ingredient is suspended or dissolved in one or more carriers. The carrier for ointment formulation include, but is not limited to mineral oil, liquid paraffin, white vaseline, propylene glycol, polyethylene oxide, polypropylene oxide, emulsifying wax and water; the carrier for lotions and creams include, but is not limited to mineral oil, sorbitan monostearate, Tween 60, hexadecylester wax, hexadecane aromatic alcohol, 2-octyl dodecanol, benzyl alcohol and water. Depending on the administration route, the amount of the active ingredient in the composition may be 0.1% by weight, or more suitably 10-60% by weight. However, when the composition is in a unit dosage form, each unit preferably comprises 50~500 mg active ingredient. Depending on the administration route and frequency, a therapeutic dose suitable for an adult, for example, may be 100-3000 mg per day, such as 1500 mg per day.

It has to be realized that the best administration dose and interval of the compound of Formula I or II depend on the severity of a disease or disorder, the properties of the compound, and administration form, route and site, and the particular mammal to be treated; and the best administration dose may be decided by clinician.

SPECIFIC MODES FOR CARRYING OUT THE INVENTION

The embodiments of the invention are described in detail in the following examples. However, those skilled in the art would understand that the following examples are only intended to describe the invention, and shall not be regarded as defining the scope of the invention. In the case where the specific conditions are not indicated in the examples, the examples are carried out according to conventional conditions or the conditions recommended by the manufacturer.

The reagents or apparatuses, the manufacturers of which are not indicated, are the conventional products that are commercially available.

Example 1. Preparation of the Compounds

Preparation of Compound 1a:

Under the protection of $N_2$, oxalyl chloride (($COCl)_2$, 2.0 eq, 28 μl) was injected into 10 ml anhydrous dichloromethane (DCM), and stirred at 0° C. N, N-dimethylformamide (DMF, 2.0 eq., 23 μl) was then added dropwise slowly and stirred at 0° C. for 30 min. 50 mg Compound 1 (dissolved in 5 ml dichloromethane) was injected into the reaction system. The reaction mixture was transferred to room temperature and stirred for 2 h, TLC method was used to track the reaction. When the raw material disappeared, 20 ml water was added to quench the reaction. The dichloromethane phase was separated, and the water phase was further extracted with 20 ml dichloromethane. The dichloromethane phases were combined, washed with saturated NaCl solution, dried with anhydrous sodium sulfate, concentrated, and subjected to silica gel column chromatography for crude separation to get Compound 1a (50.9 mg, yield: 94%).

Preparation of Compound 1b, 1c:

Compound 1 (50 mg, 0.15 mmol) and 4-dimethylamino pyridine (DMAP, 0.075 mmol, 9.2 mg) were placed in a dry reaction bottle, and dissolved in 10 ml anhydrous dichloromethane (DCM), with stirring under the protection of N2. The bottle was placed at 0° C., pyridine (0.303 mmol, 24 μl) and acetyl chloride (0.18 mmol, 14 μl) were added subsequently. After stirring for 30 min, the reaction mixture was placed at room temperature and stirred for another 2 h. TLC method was used to track the reaction. When the raw material disappeared, 20 ml water was added to quench the reaction. The dichloromethane phase was separated, the water phase was further extracted with 20 ml dichloromethane, and the dichloromethane phases were combined, washed with saturated NaCl solution, dried with anhydrous sodium sulfate, concentrated, and subjected to silica gel column chromatography for crude separation to get Compound 1b (56.3 mg, yield: 100%).

Compound 1c (20 mg, 0.049 mmol) was dissolved in 5 ml DMF, and sodium azide (10 mg, 0.15 mmol) was added. The mixture was stirred at 75° C. for 4 h. After the raw material was detected disappeared, 20 ml water was added to quench the reaction. The reaction mixture was continuously washed with ethyl acetate (3×10 ml). The organic phases were combined, washed with saturated NaCl solution, dried with anhydrous sodium sulfate, filtrated, concentrated under reduced pressure to get a concrete, the concrete was subjected to silica gel column chromatography to get Compound 1e (18 mg, yield: 88.9%).

The method for preparing other compounds (1c, 1d, 1f-1v) is similar to the method for preparing Compound 1b, wherein the acyl chloride is correspondingly chloroacetyl chloride, bromoacetyl chloride, trifluoroacetyl chloride, acryloyl chloride, 3-chloropropionyl chloride, 2-chloropropionyl chloride, benzoyl chloride, p-nitrobenzoyl chloride, p-methoxybenzoyl chloride, p-trifluoromethylbenzoyl chloride, 2-furoyl chloride, 2-thenoyl chloride, cinnamoyl chloride, methyl sulfonyl chloride, phenylmethylsulfonyl chloride, phenyl sulfonyl chloride, p-chlorophenylsulfonyl chloride, and o-nitrobenzoyl chloride. The yield is 90-100% for Compounds 1c, 1d and 1f-1t, and 20% for Compounds 1u and 1v.

Preparation of Compound 5:

Compound 1 (50 mg, 0.15 mmol) and 4-dimethylamino pyridine (DMAP, 0.075 mmol, 9.2 mg) were placed in a dry reaction bottle, dissolved with 10 ml anhydrous dichloromethane (DCM), and stirred under the protection of $N_2$. The bottle was placed at 0° C., pyridine (0.303 mmol, 24 μl) and Compound 2 (0.303 mmol, 70.0 mg) were added subsequently. After stirring for 30 min, the reaction mixture was allowed to stir at room temperature for 10 h. TLC method was used to track the reaction. When the raw material disappeared, 20 ml water was added to quench the reaction. The dichloromethane phase was separated, the water phase was further extracted with 20 ml dichloromethane, the dichloromethane phases were combined, washed with saturated NaCl solution, dried with anhydrous sodium sulfate, concentrated, and subjected to silica gel column chromatography to get Compound 3 (59.0 mg, yield: 75%). $CuSO_4$ (56.2 mg, 0.224 mmol) was dissolved in a mixed-solvent of ethanol (5 ml) and water (5 ml), then Compound 3 (59.0 mg, 0.112 mmol), Compound 4 (47.2 mg, 0.168 mmol), and ascorbic acid sodium salt (222.0 mg, 1.12 mmol) were added and stirred at room temperature for 1 h. The reaction mixture was concentrated, and subjected to silica gel column chromatography to get Compound 5 (white solid, 85.7 mg, yield: 95%).

Preparation of Compound 6:

Compound 1c (385 mg, 0.95 mol), Biotin (347 mg, 1.43 mmol), $NaHCO_3$ (119.7 mg, 1.43 mmol), and catalytic amount of CsCl (5 mg) were dissolved in 10 ml anhydrous DMF, and stirred at 75° C. for 24 h. TLC method was used to track the reaction. When the raw material disappeared, 20 ml water was added to quench the reaction. The reaction mixture was extracted with 3×20 ml ethyl acetate. The combined ethyl acetate phase was washed with saturated NaCl solution, dried with anhydrous sodium sulfate, concentrated, and subjected to silica gel column chromatography (dichloromethane-methanol 20:1) for crude separation to get Compound 6 (262.5 mg, yield: 45%).

Preparation of Compound 7:

15-oxospiramilactone (S-3) (2.00 g, 6.06 mmol) was dissolved in 50 ml anhydrous dichloromethane under the protection of $N_2$. Oxalyl chloride (7.28 mmol, 692 μl) was injected at low temperature under the protection of $N_2$ into a long-necked reaction bottle containing 5 ml anhydrous dichloromethane, the mixture was stirred at −78° C. for 20 min, DMSO solution (14.56 mmol, 1032 μl, in 5 ml DCM) was then added dropwise slowly, the addition was complete in 5 min, then the mixture was stirred at low temperature for 30 min. The solution of Compound S-3 in dichloromethane was added dropwise to the reaction bottle slowly. After stirring at −78° C. for 1 h, triethylamine (14.56 mmol, 2020 μl) was added dropwise slowly under rapid stirring, and the temperature was then increased to room temperature spontaneously. The mixture was poured into 20 ml water, the resultant mixture was extracted and separated. The water phase was further extracted with 20 ml dichloromethane, and the dichloromethane phases were combined, washed with saturated NaCl solution, dried with anhydrous sodium sulfate, and concentrated to get a residue. The residue was subjected to silica gel column chromatography to get Compound 7 (colorless powder 1888.2 mg, yield: 95.0%).

Preparation of Compound 8:

Compound 7 (1.0 mmol, 328 mg), paraformaldehyde (5 mmol, 150 mg), Bu4NI (0.2 mmol, 73.8 mg), and anhydrous potassium carbonate (2.0 mmol, 276 mg) were weighted and placed in a 50 ml dry round bottom flask. Under the protection of $N_2$, the reactants were dissolved in 15 ml anhydrous toluene, and the reaction mixture was stirred at 50° C. for 24 h. When TLC showed the raw material disappeared, the mixture was cooled to room temperature and 20 ml water was added. The resultant mixture was extracted with ethyl acetate (2×20 ml), the organic phase was subsequently washed with saturated NaCl solution, dried with anhydrous sodium sulfate, and concentrated to get a residue. The residue was subjected to silica gel column chromatography to get Compound 8 (colorless powder 204 mg, yield: 60%).

Preparation of Compound 9:

Paraformaldehyde (5 mmol, 150 mg) was weighted and suspended in 10 ml anhydrous toluene. Under the protection of $N_2$, morpholine (5 mmol, 436 μl) was injected, and stirred at 40° C. for 1 h. After the solution turned clear, it was cooled to room temperature. Compound 7 (1.0 mmol, 328 mg) in 5 ml toluene and AcOH (1.0 mmol, 60 μl) were injected subsequently, and stirred at room temperature for 3 h. When TLC showed that the raw material disappeared, the reaction was stopped. The reaction mixture was diluted with 20 ml saturated sodium hydrogen carbonate solution, extracted with ethyl acetate (2×20 ml), washed with water and saturated NaCl solution, dried with anhydrous sodium sulfate, and subjected to silica gel column chromatography to get Compound 9 (colorless powder 320 mg, yield: 75%).

Preparation of Compound 10:

Paraformaldehyde (5 mmol, 150 mg) and dimethylamine hydrochloride (5 mmol, 407.7 mg) were weighted and suspended in 10 ml anhydrous toluene. Under the protection of $N_2$, the mixture was stirred at 40° C. for 1 h. After the solution turned clear, it was cooled to room temperature. Compound 7 (1.0 mmol, 328 mg) in 5 ml toluene and AcOH (1.0 mmol, 60 μl) were injected subsequently, the resultant mixture were stirred at room temperature for 1 h. When TLC showed the raw material disappeared, the reaction was stopped. The reaction mixture was diluted with 20 ml saturated sodium hydrogen carbonate solution, extracted with ethyl acetate (2×20 ml), washed with water and saturated NaCl solution, dried with anhydrous sodium sulfate, and subjected to silica gel column chromatography to get Compound 10 (colorless powder 366 mg, yield: 95%).

Preparation of Compound 11, 12:

Compound 7 (1.0 mmol, 328 mg) was weighted and dissolved in 10 ml anhydrous DMSO. Under the protection of $N_2$, NCS (1.1 mmol, 147 mg) was added, the mixture was stirred at room temperature for 1 h. TCL showed that no reaction occurred. After heating to 45° C. and stirring for 3 h, TLC showed that the raw material disappeared, and the reaction was stopped. The mixture was cooled to room temperature, diluted with 20 ml water, extracted with ethyl acetate (2×20 ml), washed with water and saturated NaCl solution, dried with anhydrous sodium sulfate, and subjected to silica gel column chromatography to get Compound 11 (colorless powder 164.7 mg, yield: 46%) and Compound 12 (colorless oil 149.6 mg, yield: 40%).

Preparation of Compound 13:

Compound 7 (1.0 mmol, 328 mg) was weighted and dissolved in 10 ml anhydrous DMSO. Under the protection of $N_2$, NBS (1.1 mmol, 196 mg) was added, the mixture was stirred at room temperature for 1 h. TCL showed that no reaction occurred. After heating to 45° C. and stirring for 3 h, TLC showed that the raw material disappeared, and the reaction was stopped. The mixture was cooled to room temperature, diluted with 20 ml water, extracted with ethyl acetate (2×20 ml), washed with water and saturated NaCl solution, dried with anhydrous sodium sulfate, and subjected to silica gel column chromatography to get Compound 13 (brownish red powder 374 mg, yield: 92%).

Preparation of Compound 14:

Compound 7 (1.0 mmol, 328 mg) was weighted and dissolved in 5 ml anhydrous toluene. Under the protection of $N_2$, NCS (1.1 mmol, 146.8 mg) and 1 ml ionic liquid [(BMIM)$PF_4$] were added, the mixture was stirred at room temperature for 1 h. When the raw material disappeared, the stirring was stopped. The reaction mixture was diluted with 20 ml water, extracted with ethyl acetate (2×20 ml), washed with water and saturated NaCl solution, dried with anhydrous sodium sulfate, and subjected to silica gel column chromatography to get Compound 14 (colorless powder 50 mg, yield: 13.8%).

Preparation of Compound 15:

Compound S-3 (1.0 mmol, 330 mg) was dissolved in 10 ml mixed-solvent of toluene-dimethyl sulfoxide=2:1. Under the protection of $N_2$, 2-Iodoxybenzoic acid (3.0 mmol, 840 mg) was added, the resultant mixture was stirred at 70° C. for 30 h. After the raw material disappeared, the reaction mixture was cooled to room temperature, diluted with 100 ml ethyl acetate, washed subsequently with saturated sodium hydrogen carbonate solution, water, and saturated NaCl solution, dried with anhydrous sodium sulfate, and concentrated to get a residue. The residue was subjected to silica gel column chromatography to get Compound 15 (colorless powder 97.8 mg, yield: 30%).

Preparation of Compound 16:

Under the protection of $N_2$, oxalyl chloride (1.0 mmol, 95 µl) was injected into a dry long-necked reaction bottle, mixed with 5 ml anhydrous DCM, and stirred at −78° C. DMSO (2.0 mmol, 142 µl in 2 ml DCM) was added dropwise slowly and stirred for 30 min, followed by a slowly addition of S-1 (332 mg, 1.0 mmol in 2 ml DCM) dropwise, after stirring at −78° C. for 30 min, triethylamine (2.0 mmol, 278 µl) was added and the temperature was spontaneously increased to room temperature. The reaction mixture was diluted with 20 ml water, extracted with dichloromethane (2×20 ml), washed with saturated NaCl solution, dried with anhydrous sodium sulfate, and subjected to silica gel column chromatography to get Compound S-3 (165 mg), and a non-fluorescent spot (165 mg). The non-fluorescent spot was applied to a similar method for preparing Compound 8 to get Compound 16 (colorless powder 162.4 mg, two-step yield: 47.5%).

Preparation of Compound 21, 22, 23:

Compound S-1 (3.0 g, 9.04 mmol) was dissolved in 250 ml analytically pure acetone and stirred under the protection of $N_2$. p-toluene sulfonic acid (1.81 mmol, 343.5 mg) was added, and the mixture was stirred at room temperature for 24 h. During the reaction, white solid was precipitated successively. When the raw material disappeared, the reaction was stopped. The solid was filtrated, and the filter cake was washed with a solution of petroleum ether-acetone (20:1). The mother liquid was further recrystallized with a solution of petroleum ether-acetone (1:1), and air dried. The solid was combined to get the intermediate compound 17 (3.30 g, yield: 97%). The dry compound 17 was dissolved in 250 ml anhydrous THF, and stirred in an ice-bath under the protection of $N_2$. Lithium Aluminum Hydride (10.5 mmol, 400 mg) was added slowly. After stirring for 20 min, the flask was placed in a 45° C. oil bath pan and the mixture was stirred for another 3 h. When TLC showed that the raw material disappeared, the flask was replaced in an ice bath, 200 ml 2N sodium hydroxide solution was slowly added and stirred for 10 min in the ice bath. Suction filtration was performed, the filter cake was washed with ethyl acetate, and the filtrate was layered. The water phase was further extracted with ethyl acetate twice, and the ethyl acetate phases were combined, washed with saturated NaCl solution, dried with anhydrous sodium sulfate, and concentrated to get Compound 18 (colorless powder, 3.33 g, yield: 100%). Compound 18 (376.0 mg, 1.0 mmol) was dissolved in 10 ml anhydrous DCM, PDC (1.0 mmol, 376 mg) was added slowly at room temperature, and the mixture was stirred quickly at room temperature for 5 h. When TLC showed that the raw material disappeared, the reaction mixture was poured into ice water and layered. The water phase was further extracted with 20 ml dichloromethane, and the organic phases were combined, washed with saturated NaCl solution, dried with anhydrous sodium sulfate, concentrated, and subjected to silica gel column chromatography to get intermediate Compound 19 (336 mg, yield: 90%). Compound 19 (224 mg, 0.60 mmol) was dissolved in 10 ml analytically pure methanol, 2N HCl (3 ml) was added dropwise, and the mixture was stirred at 35° C. for 24 h. When the raw material disappeared, the stirring was stopped. Methanol was rotary evaporated under reduced pressure, and the resultant mixture was diluted with water, extracted with ethyl acetate, the ethyl acetate layer was washed subsequently with saturated sodium hydrogen carbonate solution and saturated NaCl solution, dried with anhydrous sodium sulfate, and subjected to silica gel column chromatography to get the intermediate compound 20 (colorless oil 198 mg, yield: 95%).

Compound 20 (50 mg, 0.144 mmol) was dissolved in 10 ml anhydrous dichloromethane, the freshly prepared active manganese dioxide were added in three batches, with an amount of 25 mg (0.288 mmol) for each batch, at an interval of 10 h. When the raw material disappeared substantively, the stirring was stopped. The manganese dioxide was filtered out, and washed with dichloromethane repeatedly. The dichloromethane phase was concentrated to get a grey oil, and the grey oil was subjected to silica gel column chromatography to get Compound 21 (colorless oil 28 mg, yield: 56.2%).

Under the protection of $N_2$, oxalyl chloride (1.28 mmol, 110 µl) was injected into a long-necked reaction bottle, and mixed with 5 ml anhydrous DCM, the solution was stirred at −78° C. DMSO (2.56 mmol, 182 µl in 2 ml DCM) was added dropwise slowly and stirred for 30 min, followed by slowly adding of Compound 20 (148 mg, 0.425 mmol in 2 ml DCM) dropwise, after stirring at −78° C. for 30 min, triethylamine (2.56 mmol, 369 µl) was added and the temperature was spontaneously increased to room temperature. The mixture was diluted with 10 ml water, extracted with dichloromethane (2×20 ml), washed with saturated NaCl solution, dried with anhydrous sodium sulfate, and subjected to silica gel column chromatography to get Compound 22 (colorless powder 146 mg, yield: 100%).

Compound 22 (0.29 mmol, 100 mg), paraformaldehyde (1.45 mmol, 44 mg), n-$Bu_4NI$ (0.06 mmol, 21 mg), and anhydrous potassium carbonate (0.58 mmol, 80 mg) were weighted and placed in a 25 ml dry round bottom flask. Under the protection of $N_2$, the reactants were dissolved in 10 ml anhydrous toluene, and the reaction mixture was stirred at 50° C. for 24 h. When TLC showed that the raw material disappeared, the mixture was cooled to room temperature and 10 ml water was added. The resultant mixture was extracted with ethyl acetate (2×15 ml), the organic phase was subsequently washed with saturated NaCl solution, dried with anhydrous sodium sulfate, and concentrated to get a residue, the residue was subjected to silica gel column chromatography to get Compound 23 (colorless powder 56.7 mg, yield: 55%).

Preparation of Compound 25, 28-33:

Compound 18 (376.0 mg, 1.0 mmol) was dissolved in 10 ml anhydrous THF. Under the protection of $N_2$, triphenyl phosphine (1.1 mmol, 288 mg) was added, followed by a slowly addition of Diisopropyl azodicarboxylate (1.1 mmol, 222 mg, diluted in 2 ml anhydrous THF), and the mixture was stirred at room temperature for 30 min. When TLC showed that the raw material disappeared, 2N dilute hydrochloric acid (5 ml) was added, the mixture was stirred at 35° C. for 24 h. When TLC showed acetonylidene was removed completely, water was added to dilute the reaction solution. The reaction solution was extracted with ethyl acetate, washed with saturated NaCl solution, dried with anhydrous sodium sulfate, and concentrated to get a residue. The residue was subjected to silica gel column chromatography to get Compound 24 (colorless oil 318 mg, yield: 100%).

Compounds 25, 33 were prepared via a similar method for the preparation of Compound 16; and Compounds 28, 31 were prepared via a similar method for the preparation of Compounds 22, 23.

In a 25 ml round bottom flask, Compound 28 (100 mg, 0.318 mmol), potassium carbonate (0.636 mmol, 87.8 mg), and paraformaldehyde (1.59 mmol, 47.7 mg) were weighted subsequently, and under the protection of $N_2$, the reactants were dissolved in 10 ml anhydrous toluene and stirred at room temperature for 24 h. TLC was used to monitor the progress of the reaction. When the raw material disappeared, the stirring was stopped. The mixture was diluted with 10 ml water, and extracted with ethyl acetate (2×15 ml), the organic phase was washed with saturated NaCl solution, dried with anhydrous sodium sulfate, and concentrated to get a residue, and the residue was subjected to silica gel column chromatography to get Compound 30 (colorless powder 82 mg, yield: 75%). In a 10 ml round bottle flask, Compound 30 (50 mg, 0.15 mmol) and 4-dimethylamino pyridine (5 mg) were weighted subsequently, and dissolved in 5 ml anhydrous dichloromethane under the protection of $N_2$. Pyridine (0.18 mmol, 15 µl), and methanesulfonyl chloride (0.18 mmol, 14 µl) were subsequently injected into the flask with an injector, and stirred at room temperature for 3 h. TLC was used to monitor the progress of the reaction. When the raw material disappeared, the stirring was stopped. The mixture was diluted with 10 ml water, and extracted with dichloromethane (2×15 ml). The organic phase was washed with saturated NaCl solution, dried with anhydrous sodium sulfate, and concentrated to get a residue, and the residue was subjected to silica gel column chromatography to get Compound 32 (colorless oil 62 mg, yield: 98%). In a 15 ml round bottom flask, Compound 32 (50 mg, 0.118 mmol) was weighted, and dissolved in 5 ml anhydrous tetrahydrofuran under the protection of $N_2$. DBU (0.236 mmol, 35 µl) was added, the mixture was stirred at room temperature for 24 h. TLC showed that the raw material disappeared. The mixture was directly concentrated under reduced pressure, and subjected to silica gel column chromatography to get Compound 31 (colorless powder 27 mg, yield: 70%).

Compound 24 (1.0 mmol, 318 mg) was dissolved in 20 ml analytically pure acetone, and slowly added with the freshly prepared Jones reagent (2.2 mmol, 0.84 ml) in an ice bath. Rapid stirring was performed for 30 min. When the raw material disappeared, isopropanol (5 ml) was added to quench the reaction. The resultant mixture was concentrated to remove acetone, diluted with water, extracted with ethyl acetate twice, washed with saturated NaCl solution, dried with anhydrous sodium sulfate, and concentrated to get a residue. The residue was subjected to silica gel column chromatography to get Compound 28 (72 mg, yield: 20.7%) and Compound 27 (45 mg, yield: 13.6%). Compound 27 was suspended in 5 ml ion liquid (BMIM)$PF_4$), morpholine (0.136 mmol, 141), acetic acid (0.136 mmol, 9 µl), and paraformaldehyde (0.68 mmol, 20 mg) were added subsequently, the mixture was stirred at 70° C. for 10 h. When the raw material disappeared, the reaction was quenched with 10 ml saturated sodium hydrogen carbonate solution. The resultant mixture was extracted with ethyl acetate (2×20 ml), the organic phase was subsequently washed with saturated NaCl solution, dried with anhydrous sodium sulfate, and concentrated to get a residue. The residue was subjected to silica gel column chromatography to get Compound 29 (32 mg, yield: 70%).

Preparation of Compound 34-36:

In a 25 ml round bottom flask, Compound 19 (112 mg, 0.3 mmol) was weighted and dissolved in 10 ml dichloromethane. Under the protection of $N_2$, 4-dimethylamino pyridine (5 mg), pyridine (1.0 mmol, 80.6 µl), and $Ac_2O$ (0.45 mmol, 42.5 µl) were added subsequently and stirred at room temperature for 3 h. When the raw material disappeared, the mixture was concentrated to get the residue 34, the residue was dissolved in 10 ml methanol. 2N HCl (5 ml) was added, and the mixture was stirred at 35° C. for 24 h. TLC showed that the raw material disappeared, and new spot appeared. The reaction mixture was concentrated to remove methanol, extracted with ethyl acetate twice. The ethyl acetate layer was subsequently washed with saturated sodium hydrogen carbonate solution, and saturated NaCl solution, dried with anhydrous sodium sulfate, and concentrated to get a residue. The residue was subjected to silica gel column chromatography to get Compound 35. Compound 35 was subjected to Swern oxidation to afford Compound 36 (79 mg, two-step yield: 95%).

Preparation of Compound 37, 38, 39:

Compound S-1 (500 mg, 1.50 mmol) was placed in a 250 ml round bottom flask, dissolved with 100 ml analytically pure methanol, and KOH (7.5 mmol, 420 mg) was added. The mixture was heated to reflux and stirred for 24 h. When the raw material disappeared, the reaction was stopped. The mixture was diluted with water, and concentrated under reduced pressure to remove methanol. The resultant solution was neutralized with 2N dilute hydrochloric acid, extracted with ethyl acetate twice, washed with saturated NaCl solution, dried with anhydrous sodium sulfate, and concentrated under reduced pressure to get Compound 37 (crude 550 mg). The dry crude Compound 37 (100 mg, 0.28 mmol) was dissolved in 50 ml anhydrous DCM contained in a round bottom flask. Under the protection of $N_2$, freshly prepared $MnO_2$ (1.42 mmol, 123.5 mg) was added in batches, and stirred at room temperature for 72 h. When the amount of the raw material remained unchanged, $MnO_2$ was filtered out. The filtrate was concentrated, and the residue was subjected to silica gel column chromatography to get Compound 38 (colorless powder 30 mg, yield: 30.2%). The dry crude Compound 37 (200 mg, 0.56 mmol) was dissolved in 50 ml analytically pure acetone contained in a round bottom flask. The flask was placed in an ice bath, Jones reagent (2.52 mmol, 0.96 ml) was added slowly. After stirring in the ice bath for 30 min, TLC showed that the raw material disappeared. The reaction was quenched with isopropanol (5 ml), and acetone was removed by concentration. The resultant mixture was diluted with water, extracted with ethyl acetate twice, washed with saturated NaCl solution, dried with anhydrous sodium sulfate, and concentrated to get a residue.

The residue was subjected to silica gel column chromatography to get Compound 39 (colorless powder, 80 mg, yield: 40.8%).

Preparation of Compound 40-53:

Compound 18 (376.0 mg, 1.0 mmol) was dissolved in 10 ml anhydrous dichloromethane, and placed at 0° C. Under the protection of $N_2$, $SOCl_2$ (1.1 mmol, 80 µl) was injected slowly. After the injection, the temperature was increased to room temperature and the mixture was stirred for 30 min. The raw material disappeared, water was added to quench the reaction, and DCM was removed by rotary evaporation. The residue was dissolved in 10 ml THF, 5 ml 2N dilute hydrochloric acid was added, and the mixture was stirred at 35° C. for 24 h. After the acetonylidene was completely removed, the stirring was stopped. The mixture was extracted with ethyl acetate twice, and the ethyl acetate phase was washed subsequently with saturated sodium hydrogen carbonate solution and saturated NaCl solution, dried with anhydrous sodium sulfate, and concentrated to get a residue. The residue was subjected to silica gel column chromatography to get the intermediate Compound 40. Compound 40 was oxidized by $MnO_2$ to get Compound 41, and Compounds 42 and 43 were prepared by Compound 40 via a similar method for the preparation of Compounds 22 and 23 correspondingly.

In a 50 ml round bottom flask, Compound 18 (752.0 mg, 2.0 mmol) and 4-dimethylamino pyridine (10 mg) were dissolved in 15 ml anhydrous dichloromethane, and placed at 0° C. Under the protection of $N_2$, pyridine (6.0 mmol, 484 µl), and acetic anhydride (6.0 mmol, 567 µl) were subsequently injected slowly. After the injection, the temperature was increased to room temperature and the mixture was stirred for 24 h. When TLC showed that the raw material disappeared, 20 ml water was added to quench the reaction. The mixture was extracted with dichloromethane (2×20 ml), and washed with saturated NaCl solution. The dichloromethane phase was dried with anhydrous sodium sulfate and concentrated to get a residue. The residue was dissolved in 15 ml THF, 8 ml 2N dilute hydrochloric acid was added, and the mixture was stirred at 35° C. for 24 h. After the acetonylidene was completely removed, the stirring was stopped. The mixture was extracted with ethyl acetate twice, and the ethyl acetate phase was washed subsequently with saturated sodium hydrogen carbonate solution and saturated NaCl solution, dried with anhydrous sodium sulfate, and concentrated to get a residue. The residue was subjected to silica gel column chromatography to get the intermediate Compound 44 (colorless oil 773 mg, yield: 92%).

Compound 44 (150 mg, 0.36 mmol) was weighted and dissolved in anhydrous dichloromethane, and the freshly prepared active manganese dioxide (2.16 mmol, 188 mg) was added in batches. The mixture was stirred at room temperature for 72 h. When the raw material disappeared substantively, the manganese dioxide was filtered out, and the filter cake was washed with dichloromethane repeatedly. The filtrate was concentrated to get a residue. The residue was subjected to silica gel column chromatography to get Compound 45 (colorless oil 113 mg, yield: 75%). Compound 45 (80 mg, 0.19 mmol) was dissolved in analytically pure tetrahydrofuran, 2N HCl (5 ml) was added, and the mixture was stirred at room temperature for 24 h. After the raw material disappeared, the mixture was diluted with 10 ml water, and extracted with ethyl acetate twice (2×20 ml). The ethyl acetate phase was washed subsequently with saturated sodium hydrogen carbonate solution, water, and saturated NaCl solution, dried with anhydrous sodium sulfate, and concentrated to get a residue. The residue was subjected to silica gel column chromatography to get Compound 46 (colorless powder, 38 mg, yield: 60%).

Compound 47, 48, 49, 52, 53 were prepared via similar methods for the preparation of Compounds 28, 30, 31, 32 correspondingly; Compound 47 was hydrolyzed with hydrochloric acid to get Compound 51, the preparation method of which was similar to that of Compound 46 from Compound 45; Compound 50 was prepared via a similar method for the preparation of Compound 9.

Preparation of Compound 55:

In a 25 ml round bottom flask, under the protection of $N_2$, the weighted Compound 18 (376.0 mg, 1.0 mmol) was dissolved in 10 ml anhydrous DMF, with stirring in an ice bath. 60% NaH (3.0 mmol, 120 mg) was added slowly, and stirred for 20 min. Bromoacetonitrile (3.0 mmol, 209 µl) was slowly injected, with stirring in an ice bath for 2 h. TLC showed that the raw material disappeared. The stirring was stopped, and water was added to quench the reaction. The mixture was extracted with 50 ml ethyl acetate and layered, the organic layer was washed with 20 ml water for three times, then washed with saturated NaCl solution, dried with anhydrous sodium sulfate, and concentrated to get a residue. The residue was subjected to silica gel column chromatography to get intermediate 54 (colorless oil 311 mg, yield: 75%). The intermediate 54 was then dissolved in 10 ml anhydrous dichloromethane, and 4-dimethylamino pyridine (5 mg) was added. Under the protection of $N_2$, pyridine (2.0 mmol, 161 µl), and 2-thiophenecarbonyl chloride (2.0 mmol, 215 µl) were subsequently added. The mixture was refluxed at 40° C. for 12 h. After the raw material disappeared, the product was subjected to deprotection of acetonylidene, and Swern oxidization to afford Compound 55 (colorless oil, 264 mg, two-step yield: 55%).

Preparation of Compound 59, 61:

Compound 18 (376.0 mg, 1.0 mmol) was placed in a 25 ml round bottom flask, dissolved in 10 ml anhydrous THF under the protection of $N_2$, and stirred in an ice bath, 60% NaH (3.0 mmol, 120 mg) was added slowly. After stirring for 20 min, 4-morpholinecarbonyl chloride (3.0 mmol, 354 µl) was injected slowly, then increased to room temperature and stirred for 3 h. No reaction occurred. After refluxing at 40° C. for 12 h, the raw material disappeared, and the reaction was quenched with 10 ml water. The mixture was extracted with an equal volume of ethyl acetate twice. The ethyl acetate phases were combined, washed with saturated NaCl solution, dried with anhydrous sodium sulfate, and concentrated to get a residue. The residue was subjected to silica gel column chromatography to get intermediates 56 (269 mg, yield: 55%) and 57 (171 mg, yield: 35%), both of which were oil-like compounds. The intermediates 56 and 57 were subjected to mesylation of hydroxyl, deprotection of acetonylidene, and Swern oxidization to get Compound 59 (colorless oil 230 mg, two-step yield: 44%) and Compound 61 (colorless oil 143 mg, two-step yield: 27%).

Preparation of Compound 62-67:

Methods for preparing of Compounds 62, 63, 64 were similar to that of Compounds 44, 45, 47 correspondingly. The methods for preparing Compounds 65, 66, 67 from Compound 64 were similar to that of Compound 29, wherein the yield was 55% for Compound 65, 20% for Compound 66, and 10% for Compound 67.

Preparation of Compound 68-70:

Compound 18 (376 mg, 1.0 mmol) and 4-dimethylamino pyridine (10 mg) were placed in a dry reaction bottle, and dissolved in 10 ml anhydrous dichloromethane (DCM) with stirring under the protection of $N_2$. The bottle was placed at 0° C., pyridine (2.0 mmol, 161 µl) and 2-thenoyl chloride (2.0 mmol, 223 µl) were added subsequently, and stirred for 30 min. The mixture was stirred at room temperature for 2 h. TLC was used to monitor the progress of the reaction, when the raw material disappeared, and two new spots appeared, the reaction was quenched with 20 ml water. The dichloromethane phase was separated, and the water phase was further extracted with 20 ml dichloromethane. The dichloromethane phases were combined, washed with saturated NaCl solution, dried with anhydrous sodium sulfate, and concentrated to get a concrete. The concrete was dissolved in anhydrous dichloromethane (10 ml), and stirred under the protection of $N_2$. Pyridine (2.0 mmol, 161 µl) and acetic anhydride (2.0 mmol, 189 µl) were added subsequently at 0° C., and stirred for 30 min. The mixture was stirred at room temperature for another 12 h. TLC was used to monitor the progress of the reaction, when the raw material disappeared, and two new spots appeared, the reaction was quenched with 20 ml water. The dichloromethane phase was separated, and the water phase was further extracted with 20 ml dichloromethane. The dichloromethane phases were combined, washed with saturated NaCl solution, dried with anhydrous sodium sulfate, and subjected to silica gel column chromatography. Compound 68 (237.6 mg, yield: 45%) was identified by two-dimensional spectrum. Compounds 69, 70 and 66, 67 may be prepared via similar methods as described above.

Preparation of Compounds (72a-72e), (73a-73e), (74a-74e): as to the synthetic methods, please refer to similar methods as described above.

Preparation of Compound 75, 76:

Compound 1 (330 mg, 1.0 mmol) was dissolved in 10 ml methanol, morpholine (1.5 mmol, 131 µl) was added, and the mixture was stirred at room temperature for 10 h. After the raw material disappeared, the reaction was stopped. The mixture was concentrated at reduced pressure to get a residue, and the residue was subjected to silica gel column chromatography to get Compounds 75 (187 mg, yield: 45%) and 76 (179 mg, yield: 43%).

Preparation of Compound 77:

Under the protection of $N_2$, spiramine C-D (357 mg, 1.0 mmol) was dissolved in 2 ml anhydrous dichloromethane to get the solution of spiramine C-D in dichloromethane. Oxalyl chloride (2.0 mmol, 190 µl) was injected into a long-necked reaction bottle containing 5 ml anhydrous dichloromethane at low temperature under the protection of $N_2$. After stirring at −78° C. for 20 min, DMSO (4.0 mmol, 283.6 µl, in 1 ml DCM) was added dropwise slowly, the addition was finished after 5 mins., the mixture was stirred at low temperature for 30 min. The solution of Compound spiramine C-D in dichloromethane was slowly added to the reaction bottle, the reaction mixture was stirred at −78° C. for 1 h. With rapid stirring, triethylamine (4.0 mmol, 555.0 µl) was added slowly. After the addition, the mixture was increased to room temperature spontaneously. 20 ml dichloromethane was added, and the mixture was poured in a separatory funnel, and washed subsequently with water and saturated NaCl solution, dried with anhydrous sodium sulfate, and concentrated to get a residue. The residue was subjected to silica gel column chromatography to get Compound 77 (colorless powder 340.8 mg, yield: 96.0%).

Preparation of Compound 78:

Spiramine C-D (357 mg, 1.0 mmol) was dissolved in 20 ml acetone, and self-made active $MnO_2$ (2610 mg, 30.0 mmol) was added in batches. After stirring at room temperature for 72 h, it was by TLC that the raw material disappeared substantively, the mixture was filtered, and the filter residue was washed with $CH_2Cl_2$ repeatedly. The filtrate was concentration at reduced pressure to get a residue, and the residue was subjected to silica gel column chromatography (petroleum ether-acetone 3:1) to get product 78 (148.4 mg, yield: 40%).

Preparation of Compound 79, 80:

The alkaloid spiramine C-D (2000 mg, 5.6 mmol) was dissolved in 200 ml analytically pure methanol, sodium borohydride (424 mg, 11.2 mmol) was added in batches, and the mixture was stirred at room temperature for 3 h. When the raw material disappeared, the reaction was quenched with acetone. The reaction mixture was concentrated under reduced pressure to remove methanol, extracted with dichloromethane (2×100 ml), washed with water and saturated NaCl solution, and dried with anhydrous sodium sulfate to get Compound 79 (1980 mg, yield: 98%), which was further oxidized by $MnO_2$ to get Compound 80 (colorless solid, 39.0 mg, 12.5% at 79=361 mg).

Preparation of Compound 81-84:

The dry Compound 79 (361 mg, 1.0 mmol) was dissolved in 10 ml methanol, an aqueous solution of $K_3Fe(CN)_6$ (1273 mg, 3.8 mmol in 10 ml $H_2O$) was added, followed by an addition of aqueous solution of KOH (8% KOH solution, 14.5 ml). The mixture was stirred for 30 min. After the raw material disappeared, the mixture was extracted with dichloromethane (2×100 ml), washed with water, dried with anhydrous sodium sulfate, and concentrated at reduced pressure to get a concrete. The concrete was subjected to silica gel column chromatography to get Compound 81 (colorless oil, 254.8 mg, 71%), one half of which was oxidized by $MnO_2$ (152.2 mg, 1.75 mmol) to get Compound 82, and the other half of which was oxidized by large excess of $MnO_2$ (1.0 g, 11.5 mmol) to get Compound 83 (45.4 mg, 35%), Compound 84 (20 mg, 18%).

Preparation of Compound 85-93:

The anhydrous Compound 79 (904 mg, 2.5 mmol) was dissolved in 20 ml anhydrous DMF. The solution was placed in an ice bath, under the protection of $N_2$, t-butyldimethylsilyl chloride (TBDMSCl, 2.5 mmol, 375 mg) and imidazole (imidazole, 2.5 mmol, 170 mg) were added subsequently, the mixture was stirred at room temperature for 2 h. After the raw material disappeared, the mixture was diluted with water (50 ml), extracted with ethyl acetate (2×100 ml), washed subsequently with water and saturated NaCl solution, dried with anhydrous sodium sulfate, and concentrated under reduced pressure to get a residue. The residue was subjected to silica gel column chromatography (petroleum ether-acetone 5:1-3:1) to get the intermediate Compound 85 (colorless oil, 1068 mg, yield: 90.0%). Under the protection of $N_2$, oxalyl chloride (2.5 mmol, 216 µl) was injected into a long-necked dry reaction bottle, and mixed with 10 ml anhydrous DCM. The solution was stirred at −78° C., DMSO (5.0 mmol, 354.5 µl in 2 ml DCM) was added dropwise slowly. After stirring for 30 min, Compound 85 (1068 mg, 2.25 mmol, in 5 ml DCM) was added slowly. After stirring at −78° C. for 30 min, trimethylamine (5.0 mmol, 693.7 µl) added, and the reaction mixture was increased to room temperature spontaneously, diluted with 20 ml water, extracted with dichloromethane (2×20 ml), washed with saturated NaCl solution, dried with anhydrous sodium sulfate, and concentrated to get a cream. The cream was subjected to silica gel column chromatography to get Compound 86 (212.8 mg, 0.45 mmol, 20%), Compound 87 (179.7 mg, 0.38 mmol, 16.8%), and a mixture of Compound 86 and Compound 87 (572.3 mg, 1.21 mmol, 53.7%). Compound 86 (212.8 mg, 0.45 mmol), paraformaldehyde (67.5 mg, 2.25 mmol), n-Bu$_4$NI (7 mg, 0.02 mmol), and anhydrous potassium carbonate (186 mg, 1.35 mmol) were placed in a 50 ml dry round bottom flask, and dissolved in 10 ml anhydrous toluene under the protection of $N_2$. The reaction mixture was stirred at 50° C. for 24 h. When TLC showed that the raw material disappeared, the mixture was cooled to room temperature, and 20 ml water was added. The resultant mixture was extracted with ethyl acetate (2×20 ml), and the organic phase was subsequently washed with saturated NaCl solution, dried with anhydrous sodium sulfate, and concentrated to get a residue. The dried residue was dissolved in 10 ml anhydrous THF. Under the protection of $N_2$, TBAF (1110 μl, 1 MTBAF in THF) was injected with stirring. After stirred at room temperature for 3 h, the raw material disappeared, the mixture was diluted with 20 ml water, extracted with ethyl acetate (2×20 ml), washed with saturated NaCl solution, dried with anhydrous sodium sulfate, and concentrated to get a residue. The residue was subjected to silica gel column chromatography to get Compound 89 (colorless oil, 66.7 mg, yield: 40.0%). Compound 87 (179.7 mg, 0.38 mmol) was deprotected with TBAF to get Compound 88 (colorless oil, 75 mg, 55%). The mixture of Compounds 86 and 87 (572.3 mg, 1.21 mmol) was further subjected to Swern oxidization to get Compound 90 (541 mg, 1.15 mmol, 95%). Compounds 91-93 may be prepared from Compound 90 via similar methods as described above.

Spectrum Data of the Compounds

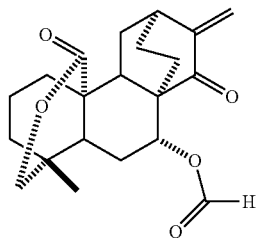

Compound 1a: $^1$H NMR (400 MHz, CDCl$_3$) δ: 8.05 (1H, s), 5.95 (1H, d, J=1.4 Hz), 5.43 (1H, dd, J=4.4, 10.8 Hz), 5.25 (1H, d, J=1.4 Hz), 4.24 (1H, dd, J=2.4, 11.6 Hz), 4.12 (1H, d, J=11.6 Hz), 3.14 (1H, m), 2.81 (1H, brs), 2.16-2.27 (4H, m), 1.85-1.92 (1H, m), 1.60-1.78 (5H, m), 1.53-1.57 (1H, m), 1.33-1.48 (3H, m), 1.18-1.26 (1H, m), 0.95 (3H, s). $^{13}$C NMR (100 MHz, CDCl$_3$) δ: 200.6, 173.7, 160.4, 147.3, 117.3, 76.4, 70.6, 48.7, 46.4, 45.7, 44.6, 40.6, 37.3, 35.6, 32.8, 26.9, 25.8, 23.7, 23.4, 20.1, 17.2. HREIMS m/z 358.1781 [M]$^+$ (C$_{21}$H$_{26}$O$_5$, calcd. 358.1780).

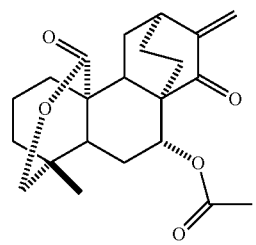

Compound 1b: $^1$H NMR (400 MHz, CDCl$_3$) δ: 5.84 (1H, d, J=1.6 Hz), 5.22 (1H, dd, J=4.4, 11.6 Hz), 5.15 (1H, d, J=1.6 Hz), 4.15 (1H, dd, J=3.6, 11.6 Hz), 4.13 (1H, d, J=11.6 Hz), 3.05 (1H, m), 2.72 (1H, t, J=2.8, 2.8 Hz), 2.05-2.16 (3H, m), 1.92 (3H, s), 1.68-1.82 (1H, m), 1.08-1.68 (11H, m), 0.86 (3H, s). $^{13}$C NMR (100 MHz, CDCl$_3$) δ: 200.4, 173.7, 169.9, 147.4, 116.7, 76.2, 70.4, 48.5, 46.1, 45.6, 44.4, 40.4, 37.1, 35.6, 32.6, 26.8, 25.6, 23.6, 23.3, 20.9, 20.0, 17.1. HREIMS m/z 372.1930 [M]$^+$ (C$_{22}$H$_{28}$O$_5$, calcd. 372.1937).

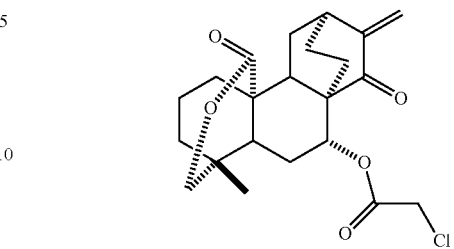

Compound 1c: $^1$H NMR (400 MHz, CDCl$_3$) δ: 5.93 (1H, d, J=1.2 Hz), 5.39 (1H, dd, J=5.2, 11.2 Hz), 5.25 (1H, d, J=1.2 Hz), 4.23 (1H, dd, J=2.4, 12.0 Hz), 4.12 (1H, d, J=12.0 Hz), 4.03 (2H, dd, J=14.8, 18.8 Hz), 3.14 (1H, m), 2.82 (1H, brs), 2.18-2.27 (3H, m), 1.86-1.92 (1H, m), 1.62-1.78 (6H, m), 1.53-1.59 (1H, m), 1.34-1.49 (3H, m), 1.16-1.23 (1H, m), 0.96 (3H, s). $^{13}$C NMR (100 MHz, CDCl$_3$) δ: 200.4, 173.7, 166.4, 147.2, 117.3, 76.4, 72.7, 48.7, 46.3, 45.9, 44.5, 41.0, 40.6, 37.3, 35.6, 32.8, 26.9, 25.6, 23.7, 23.5, 20.1, 17.2. HREIMS m/z 406.1550 [M]$^+$ (C$_{22}$H$_{27}$ClO$_5$, calcd. 406.1547).

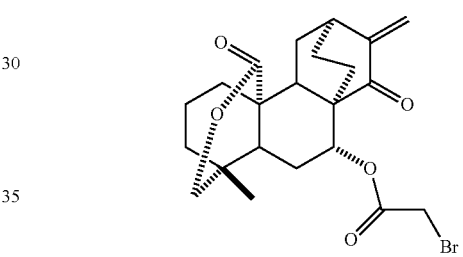

Compound 1d: $^1$H NMR (400 MHz, CDCl$_3$) δ: 5.93 (1H, d, J=1.2 Hz), 5.37 (1H, dd, J=4.4, 11.2 Hz), 5.24 (1H, d, J=1.2 Hz), 4.24 (1H, dd, J=2.4, 11.6 Hz), 4.11 (1H, d, J=11.6 Hz), 3.81 (2H, dd, J=12.4, 16.4 Hz), 3.14 (1H, m), 2.81 (1H, brs), 2.15-2.25 (3H, m), 1.86-1.92 (1H, m), 1.62-1.78 (6H, m), 1.33-1.57 (4H, m), 1.15-1.22 (1H, m), 0.95 (3H, s). $^{13}$C NMR (100 MHz, CDCl$_3$) δ: 200.4, 173.7, 166.2, 147.3, 117.3, 76.4, 72.6, 48.7, 46.2, 45.7, 44.5, 40.5, 37.3, 35.6, 32.8, 26.9, 26.2, 25.4, 23.7, 23.4, 20.1, 17.1. HREIMS m/z 450.1045 [M]$^+$ (C$_{22}$H$_{27}$O$_5$Br, calcd. 450.1042).

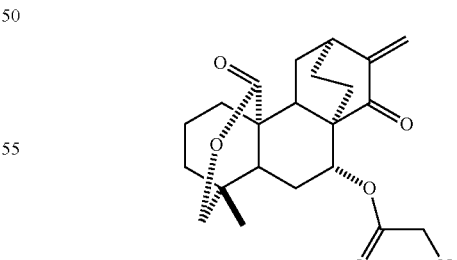

Compound 1e: $^1$H NMR (400 MHz, CDCl$_3$) δ: 5.93 (1H, d, J=1.2 Hz), 5.41 (1H, dd, J=4.0, 11.2 Hz), 5.24 (1H, d, J=1.2 Hz), 3.82 (2H, dd, J=16.8, 32.4 Hz), 3.15 (1H, m), 2.82 (1H, brs), 2.18-2.27 (3H, m), 1.86-1.92 (1H, m), 1.62-1.75 (6H, m), 1.54-1.58 (1H, m), 1.35-1.49 (3H, m), 1.16-1.34 (3H, m), 0.96 (3H, s). $^{13}$C NMR (100 MHz, CDCl$_3$) δ: 200.5, 173.7, 167.5, 147.2, 117.3, 76.4, 72.5, 50.3, 48.7, 46.3, 45.7, 44.5, 40.5, 37.2, 35.6, 32.8, 26.9, 25.8, 23.6, 23.5, 20.1, 17.3. HREIMS m/z 413.1956 [M]$^+$ (C$_{22}$H$_{27}$N$_3$O$_5$, calcd. 413.1951).

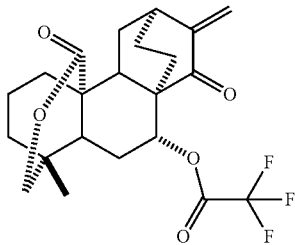

Compound 1f: $^1$H NMR (400 MHz, CDCl$_3$) δ: 5.88 (1H, d, J=1.6 Hz), 5.49 (1H, dd, J=4.4, 12.0 Hz), 5.21 (1H, d, J=1.6 Hz), 4.21 (1H, dd, J=2.4, 12.0 Hz), 4.08 (1H, d, J=12.0 Hz), 3.11 (1H, m), 2.77 (1H, t, J=3.6, 3.6 Hz), 2.11-2.22 (3H, m), 1.74-1.89 (1H, m), 1.55-1.74 (7H, m), 1.37-1.48 (3H, m), 1.15-1.29 (1H, m), 0.93 (3H, s). $^{13}$C NMR (100 MHz, CDCl$_3$) δ: 199.8, 173.5, 156.2 (q, J=41.9 Hz, COCF$_3$), 146.8, 117.6, 114.8 (d, J=283.8 Hz, CF$_3$), 76.3, 75.1, 48.7, 46.1, 45.5, 44.1, 40.4, 37.1, 35.5, 32.7, 26.9, 25.3, 23.4, 23.3, 20.0, 17.0. HREIMS m/z 426.1661 [M]$^+$ (C$_{22}$H$_{25}$F$_3$O$_5$, calcd. 426.1654).

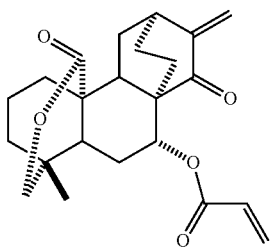

Compound 1g: $^1$H NMR (400 MHz, CDCl$_3$) δ: 6.35 (1H, dd, J=0.8, 17.2 Hz), 6.05 (1H, dd, J=10.4, 17.2 Hz), 5.93 (1H, d, J=0.8 Hz), 5.79 (1H, dd, J=0.8, 10.4 Hz), 5.40 (1H, dd, J=4.4, 12.0 Hz), 5.23 (1H, d, J=0.8 Hz), 4.22 (1H, dd, J=2.0, 11.6 Hz), 4.10 (1H, d, J=11.6 Hz), 3.14 (1H, m), 2.81 (1H, t, J=2.8, 2.8 Hz), 2.19-2.28 (3H, m), 1.88-1.95 (1H, m), 1.16-1.80 (11H, m), 0.94 (3H, s). $^{13}$C NMR (100 MHz, CDCl$_3$) δ: 200.4 173.9, 165.2, 147.4, 130.6, 128.5, 117.0, 76.4, 70.6, 48.8, 46.3, 45.7, 44.6, 40.6, 37.3, 35.7, 32.8, 26.9, 25.7, 23.8, 23.4, 20.1, 17.3. HREIMS m/z 384.1923 [M]$^+$ (C$_{23}$H$_{28}$O$_5$, calcd. 384.1937).

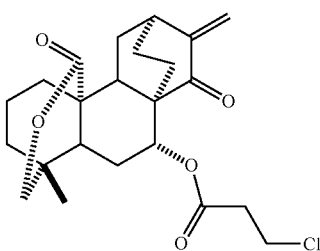

Compound 1h: $^1$H NMR (400 MHz, CDCl$_3$) δ: 5.90 (1H, d, J=1.6 Hz), 5.31 (1H, dd, J=4.0, 10.0 Hz), 5.20 (1H, d, J=1.6 Hz), 4.19 (1H, dd, J=2.0, 11.6 Hz), 4.07 (1H, d, J=11.6 Hz), 3.69 (2H, m), 3.11 (1H, m), 2.78 (1H, t, J=2.8, 2.8 Hz), 2.73 (2H, m), 2.12-2.22 (2H, m), 1.83-1.89 (1H, m), 1.31-1.74 (11H, m), 1.49-1.61 (1H, m), 0.92 (3H, s). $^{13}$C NMR (100 MHz, CDCl$_3$) δ: 200.6, 173.8, 169.3, 147.3, 117.2, 76.4, 71.2, 48.7, 46.3, 45.7, 44.5, 40.6, 38.9, 37.6, 37.3, 35.6, 32.8, 26.9, 25.7, 23.6, 23.5, 20.1, 17.3. HREIMS m/z 420.1701 [M]$^+$ (C$_{23}$H$_{29}$ClO$_5$, calcd. 420.1704).

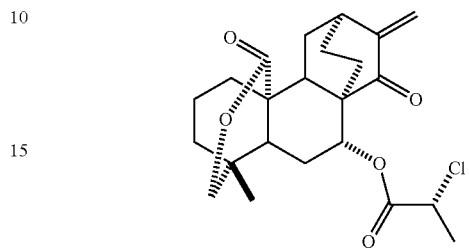

Compound 1i: $^1$H NMR (400 MHz, CDCl$_3$) δ: 5.93 (1H, s), 5.36 (1H, m), 5.23 (1H, s), 4.36 (1H, m), 4.21 (1H, d, J=12.0 Hz), 4.11 (1H, d, J=12.0 Hz), 3.14 (1H, m), 2.81 (1H, brs), 2.15-2.27 (2H, m), 1.87-1.93 (1H, m), 1.35-1.78 (13H, m), 1.23-1.65 (1H, m), 0.96 (3H, s). $^{13}$C NMR (100 MHz, CDCl$_3$) δ: 200.1, 173.7, 168.8, 147.2, 117.2, 76.3, 72.2, 52.9, 48.7, 46.1, 45.6, 44.3, 40.5, 37.1, 35.6, 32.7, 26.9, 25.4, 23.6, 23.4, 21.5, 20.1, 17.2. HREIMS m/z 420.1687 [M]$^+$ (C$_{23}$H$_{29}$ClO$_5$, calcd. 420.1704).

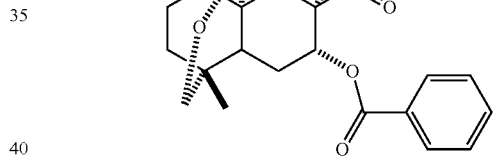

Compound 1j: $^1$H NMR (400 MHz, CDCl$_3$) δ: 7.95 (2H, d, J=7.2 Hz), 7.52 (1H, t, J=7.2, 8.0 Hz), 7.40 (2H, t, J=7.2, 8.0 Hz), 5.91 (1H, d, J=1.6 Hz), 5.23 (1H, d, J=1.6 Hz), 4.23 (1H, dd, J=2.0, 12.0 Hz), 4.12 (1H, d, J=12.0 Hz), 3.16 (1H, m), 2.84 (1H, brs), 2.17-2.31 (3H, m), 2.01-2.08 (1H, m), 1.88-1.96 (1H, m), 1.61-1.69 (5H, m), 1.41-1.51 (3H, m), 1.18-1.27 (2H, m), 0.96 (3H, s). $^{13}$C NMR (100 MHz, CDCl$_3$) δ: 200.4 173.9, 165.5, 147.3, 132.8, 130.4, 129.6 (2C$_{Ar}$), 128.2 (2C$_{Ar}$), 117.2, 76.5, 70.9, 49.0, 46.3, 45.8, 44.6, 40.6, 37.3, 35.7, 32.8, 27.1, 25.9, 23.8, 23.4, 20.2, 17.5. HREIMS m/z 434.2086 [M]$^+$ (C$_{27}$H$_{30}$O$_5$, calcd. 434.2093).

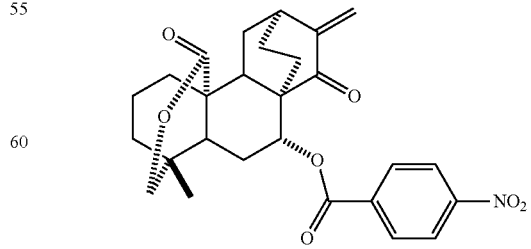

Compound 1k: $^1$H NMR (400 MHz, CDCl$_3$) δ: 7.50 (2H, d, J=9.6 Hz), 8.12 (2H, d, J=9.6 Hz), 5.92 (1H, s), 5.63 (1H, dd, J=4.0, 11.6 Hz), 5.26 (1H, s), 4.24 (1H, d, J=12.0 Hz), 4.13 (1H, d, J=12.0 Hz), 3.19 (1H, m), 2.86 (1H, brs), 2.17-2.32 (3H, m), 2.04-2.11 (1H, m), 1.61-1.91 (7H, m), 1.43-1.55 (3H, m), 1.23-1.27 (1H, m), 0.97 (3H, s). $^{13}$C NMR (100 MHz, CDCl$_3$) δ: 200.4, 173.8, 163.6, 150.4, 147.2, 135.8, 130.7 (2C$_{Ar}$), 123.4 (2C$_{Ar}$), 117.5, 76.4, 72.3, 49.0, 46.4, 45.8, 44.5, 40.6, 37.2, 35.6, 32.8, 27.0, 25.8, 23.7, 23.5, 20.2, 17.6. HREIMS m/z 479.1945 M]$^+$ (C$_{27}$H$_{29}$NO$_7$, calcd. 479.1945).

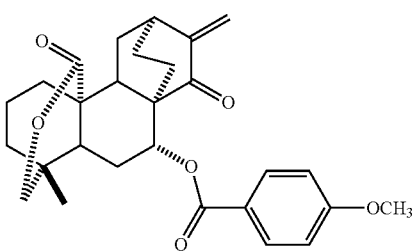

Compound 1l: $^1$H NMR (400 MHz, CDCl$_3$) δ: 7.91 (2H, d, J=8.8 Hz), 6.88 (2H, d, J=8.8 Hz), 5.92 (1H, d, J=1.6 Hz), 5.55 (1H, dd, J=4.0, 10.8 Hz), 5.23 (1H, d, J=1.6 Hz), 4.24 (1H, dd, J=2.4, 11.6 Hz), 4.11 (1H, d, J=11.6 Hz), 3.84 (3H, s), 3.15 (1H, m), 2.83 (1H, t, J=2.8, 2.8 Hz), 1.21-2.31 (11H, m), 0.95 (3H, s). $^{13}$C NMR (100 MHz, CDCl$_3$) δ: 200.4, 174.0, 165.2, 163.2, 147.4, 131.6 (2C$_{Ar}$), 122.9, 117.1, 113.4 (2C$_{Ar}$), 76.5, 70.6, 55.4, 49.0, 46.3, 45.8, 44.7, 40.6, 37.3, 35.8, 32.8, 27.0, 25.9, 23.8, 23.5, 20.2, 17.6. HREIMS m/z 464.2602 [M]$^+$ (C$_{28}$H$_{32}$O$_6$, calcd. 464.2199).

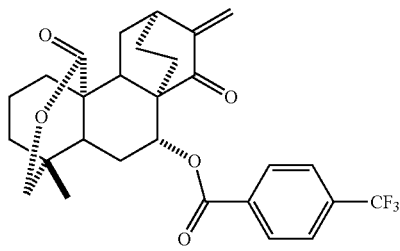

Compound 1m: $^1$H NMR (400 MHz, CDCl$_3$) δ: 8.07 (2H, d, J=8.0 Hz), 7.67 (2H, d, J=8.0 Hz), 5.92 (1H, d, J=1.2 Hz), 5.61 (1H, dd, J=4.0, 10.0 Hz), 5.25 (1H, d, J=1.2 Hz), 4.24 (1H, dd, J=1.6, 12.0 Hz), 4.12 (1H, d, J=12.0 Hz), 3.17 (1H, m), 2.85 (1H, brs), 2.22-2.34 (2H, m), 2.02-2.10 (1H, m), 1.60-1.92 (7H, m), 1.41-1.54 (3H, m), 1.19-1.25 (2H, m), 0.97 (3H, s). $^{13}$C NMR (100 MHz, CDCl$_3$) δ: 200.4, 173.9, 164.3, 147.2, 134.1 (q, J=32.0 Hz), 133.6, 129.9 (2C$_{Ar}$), 125.3 (2C$_{Ar}$), 123.5 (q, J=270.9 Hz), 117.4, 76.4, 71.7, 49.0, 46.3, 45.8, 44.5, 40.6, 37.2, 35.7, 32.8, 27.0, 25.8, 23.7, 23.5, 20.2, 17.6. HREIMS m/z 502.1962 [M]$^+$ (C$_{28}$H$_{29}$F$_3$O$_5$, calcd. 502.1967).

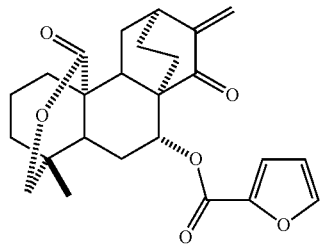

Compound 1n: $^1$H NMR (400 MHz, CDCl$_3$) δ: 7.54 (1H, s), 7.08 (1H, d, J=3.2 Hz), 6.46 (1H, d, J=2.0 Hz), 5.93 (1H, s), 5.56 (1H, brs), 5.23 (1H, s), 4.23 (1H, d, J=11.6 Hz), 4.09 (1H, d, J=11.6 Hz), 3.16 (1H, m), 2.83 (1H, brs), 2.17-2.28 (4H, m), 1.96-2.02 (1H, m), 1.72-1.90 (6H, m), 1.39-1.46 (3H, m), 1.21-1.25 (1H, m), 0.95 (3H, s). $^{13}$C NMR (100 MHz, CDCl$_3$) δ: 200.4, 173.9, 157.7, 147.3, 146.2, 144.7, 117.8, 117.2, 111.7, 76.4, 70.9, 48.8, 46.3, 45.7, 44.6, 40.6, 37.3, 35.7, 32.8, 27.0, 25.9, 23.7, 23.4, 20.1, 17.4. HREIMS m/z 424.1871 [M]$^+$ (C$_{25}$H$_{28}$O$_6$, calcd. 424.1886).

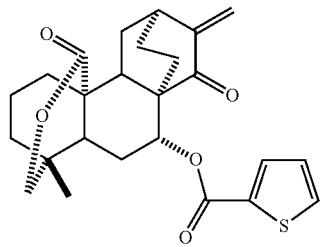

Compound 1o: $^1$H NMR (400 MHz, CDCl$_3$) δ: 7.74 (1H, d, J=3.2 Hz), 7.51 (1H, d, J=4.8 Hz), 7.06 (1H, m), 5.92 (1H, s), 5.54 (1H, dd, J=4.0, 10.4 Hz), 5.24 (1H, s), 4.23 (1H, dd, J=1.2, 12.0 Hz), 4.12 (1H, d, J=12.0 Hz), 3.16 (1H, m), 2.83 (1H, brs), 2.17-2.31 (3H, m), 1.86-2.17 (1H, m), 1.58-1.82 (7H, m), 1.42-1.58 (3H, m), 1.18-1.39 (1H, m), 0.96 (3H, s). $^{13}$C NMR (100 MHz, CDCl$_3$) δ: 200.4, 173.9, 161.1, 147.3, 133.9, 133.3, 132.2, 127.6, 117.3, 76.4, 71.2, 48.9, 46.3, 45.8, 44.6, 40.6, 37.3, 35.7, 32.8, 27.0, 25.9, 23.8, 23.5, 20.2, 17.5. HREIMS m/z 440.1656 [M]$^+$ (C$_{25}$H$_{28}$O$_5$S, calcd. 440.1657).

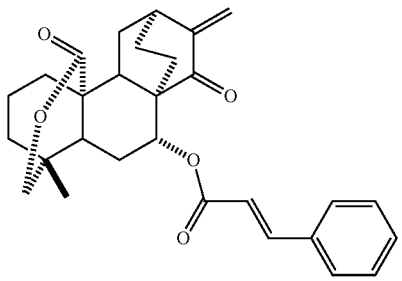

Compound 1p: $^1$H NMR (400 MHz, CDCl$_3$) δ: 7.64 (1H, d, J=12.0 Hz), 7.50 (2H, m), 7.36 (3H, m), 6.37 (1H, d, J=12.0 Hz), 5.94 (1H, s), 5.48 (1H, m), 5.23 (1H, s), 4.24 (1H, dd, J=2.4, 12.0 Hz), 4.11 (1H, d, J=12.0 Hz), 3.15 (1H, m), 2.82 (1H, brs), 2.17-2.26 (3H, m), 1.92-1.99 (1H, m), 1.56-1.87 (8H, m), 1.39-1.49 (2H, m), 1.17-1.23 (1H, m), 0.95 (3H, s). $^{13}$C NMR (100 MHz, CDCl$_3$) δ: 200.6, 174.0, 165.9, 147.4, 144.7, 134.4, 130.1, 128.7 (2C$_{Ar}$), 128.0 (2C$_{Ar}$), 118.2, 117.1, 76.4, 70.5, 48.8, 46.3, 45.8, 44.6, 40.6, 37.7, 35.7, 32.8, 30.9, 27.0, 25.8, 23.8, 20.2, 17.4. HREIMS m/z 460.2247 [M]$^+$ (C$_{29}$H$_{32}$O$_5$, calcd. 460.2250).

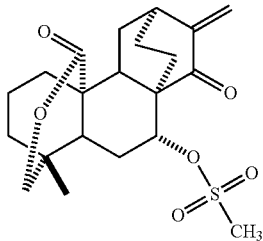

Compound 1q: $^1$H NMR (400 MHz, CDCl$_3$) δ: 5.97 (1H, s), 5.29 (1H, s), 5.10 (1H, dd, J=4.4, 12.0 Hz), 4.27 (1H, dd, J=2.4, 12.0 Hz), 4.24 (1H, d, J=12.0 Hz), 3.18 (3H, s), 3.13 (1H, m), 2.83 (1H, brs), 2.45-2.50 (1H, m), 2.18-2.28 (3H, m), 1.85-1.90 (1H, m), 1.60-1.76 (5H, m), 1.40-1.59 (2H, m), 1.25-1.32 (2H, m), 1.15-1.19 (1H, m), 0.97 (3H, s). $^{13}$C NMR (100 MHz, CDCl$_3$) δ: 200.7, 173.5, 147.3, 117.8, 79.9, 76, 3, 49.1, 46.3, 45.5, 44.9, 40.5, 38.6, 37.2, 35.5, 32.8, 28.2, 26.8, 23.5, 23.3, 20.0, 16.8. HREIMS m/z 408.1613 [M]$^+$ (C$_{21}$H$_{28}$O$_6$S, calcd. 408.1607).

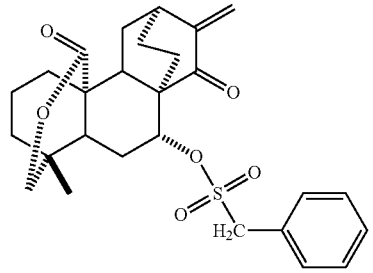

Compound 1r: $^1$H NMR (400 MHz, CDCl$_3$) δ: 7.35 (5H, m), 6.04 (1H, d, J=1.2 Hz), 5.33 (1H, d, J=1.2 Hz), 5.25 (1H, dd, J=5.2, 12.0 Hz), 4.64 (1H, d, J=14.0 Hz), 4.46 (1H, d, J=14.0 Hz), 4.17 (1H, dd, J=2.4, 11.6 Hz), 4.08 (1H, d, J=11.6 Hz), 3.14 (1H, m), 2.85 (1H, t, J=2.8, 2.8 Hz), 2.16-2.29 (3H, m), 1.36-1.83 (11H, m), 1.26-1.29 (1H, m), 1.10-1.85 (1H, m), 0.91 (3H, s). $^{13}$C NMR (100 MHz, CDCl$_3$) δ: 200.8, 173.5, 147.3, 130.8, 128.7 (2C$_{Ar}$), 128.6 (2C$_{Ar}$), 128.4, 117.9, 79.8, 76.3, 57.2, 49.1, 46.2, 45.4, 44.9, 40.5, 37.1, 35.5, 32.8, 28.1, 26.8, 23.7, 23.3, 20.1, 16.7. HREIMS m/z 484.1921 [M]$^+$ (C$_{27}$H$_{32}$O$_6$S, calcd. 484.1920).

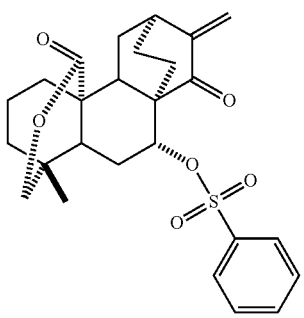

Compound 1s: $^1$H NMR (400 MHz, CDCl$_3$) δ: 7.95 (2H, m), 7.61 (1H, m), 7.53 (2H, m), 5.83 (1H, d, J=1.6 Hz), 5.29 (1H, dd, J=4.8, 12.0 Hz), 5.18 (1H, d, J=1.6 Hz), 4.22 (1H, dd, J=2.4, 12.0 Hz), 4.10 (1H, d, J=12.0 Hz), 3.08 (1H, m), 2.76 (1H, t, J=2.8, 2.8 Hz), 2.49 (1H, m), 2.15-2.22 (2H, m), 1.53-1.84 (7H, m), 1.40-1.51 (2H, m), 1.25-1.32 (1H, m), 1.10-1.18 (1H, m), 0.96 (3H, s). $^{13}$C NMR (100 MHz, CDCl$_3$) δ: 199.2, 173.4, 147.0, 137.6, 133.3, 128.7 (2C$_{Ar}$), 127.8 (2C$_{Ar}$), 117.3, 79.2, 76.3, 49.1, 46.2, 45.4, 45.0, 40.5, 37.1, 35.4, 32.8, 27.5, 26.7, 23.6, 23.3, 20.0, 16.6. HREIMS m/z 470.1770[M]$^+$ (C$_{26}$H$_{30}$O$_6$S, calcd. 470.1763).

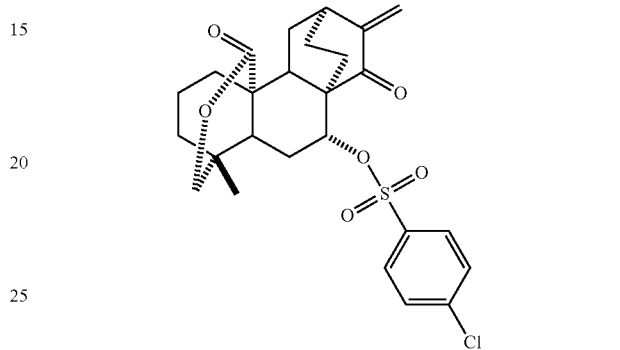

Compound 1t: $^1$H NMR (400 MHz, CDCl$_3$) δ: 7.92 (2H, d, J=6.4 Hz), 7.50 (2H, d, J=6.4 Hz), 5.83 (1H, d, J=2.0 Hz), 5.27 (1H, dd, J=5.2, 12.4 Hz), 5.19 (1H, d, J=2.0 Hz), 4.26 (1H, dd, J=2.4, 12.0 Hz), 4.12 (1H, d, J=12.0 Hz), 3.09 (1H, m), 2.76 (1H, m), 2.51 (1H, m), 2.16-2.22 (3H, m), 1.10-1.84 (12H, m), 0.99 (3H, s). $^{13}$C NMR (100 MHz, CDCl$_3$) δ: 199.7, 173.7, 147.3, 140.2, 136.3, 129.6 (2C$_{Ar}$), 129.2 (2C$_{Ar}$), 117.8, 80.2, 76.6, 49.3, 46.5, 45.7, 45.3, 40.8, 37.4, 35.7, 33.1, 28.0, 27.1, 23.8, 20.3, 20.1, 17.0, HREIMS m/z 504.1386 [M]$^+$ (C$_{26}$H$_{29}$ClO$_6$S, calcd. 504.1373).

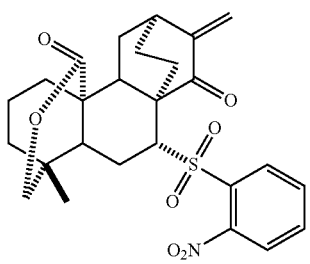

Compound 1u: $^1$H NMR (400 MHz, CDCl$_3$) δ: 8.31 (1H, d, J=8.0 Hz), 8.20 (1H, d, J=8.0 Hz), 7.88 (1H, t, J=7.6, 7.6 Hz), 7.71 (1H, t, J=7.6, 7.6 Hz), 6.05 (1H, s), 5.26 (1H, s), 5.12 (1H, dd, J=4.8, 11.2 Hz), 4.18 (1H, dd, J=2.0, 11.6 Hz), 4.08 (1H, d, J=11.6 Hz), 3.06 (1H, m), 2.78 (1H, brs), 1.11-2.17 (15H, m), 0.98 (3H, s). $^{13}$C NMR (100 MHz, CDCl$_3$) δ: 200.8, 173.5, 147.3, 145.8, 143.3, 134.8, 132.2, 126.5, 124.8, 117.9, 78.6, 76.3, 50.2, 46.5, 45.2, 40.6, 37.1, 35.5, 32.8, 30.9, 27.2, 27.0, 23.8, 23.3, 20.1, 16.5. HREIMS m/z 499.1670 [M]$^+$ (C$_{26}$H$_{29}$NO$_7$S, calcd. 499.1665).

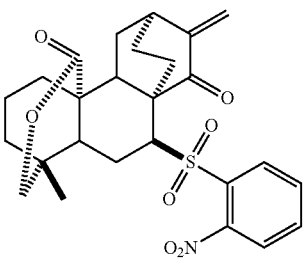

Compound ¹H NMR (400 MHz, CDCl₃) δ: 8.25 (1H, d, J=8.0 Hz), 8.18 (1H, d, J=8.0 Hz), 7.86 (1H, t, J=7.6, 7.6 Hz), 7.69 (1H, t, J=7.6, 7.6 Hz), 5.99 (1H, s), 5.28 (1H, s), 5.05 (1H, dd, J=4.8, 12.0 Hz), 4.23 (1H, dd, J=2.0, 11.6 Hz), 4.08 (1H, d, J=11.6 Hz), 3.07 (1H, m), 2.78 (1H, brs), 1.11-2.29 (15H, m), 0.97 (3H, s). ¹³C NMR (100 MHz, CDCl₃) δ: 200.4, 173.6, 147.2, 145.6, 143.1, 134.6, 132.3, 125.6, 124.7, 117.6, 76.6, 76.3, 49.9, 46.6, 45.3, 40.6, 37.2, 35.5, 32.8, 30.9, 28.8, 26.9, 23.8, 23.5, 20.1, 16.2. HREIMS m/z 499.1651 [M]⁺ ($C_{26}H_{29}NO_7S$, calcd. 499.1665).

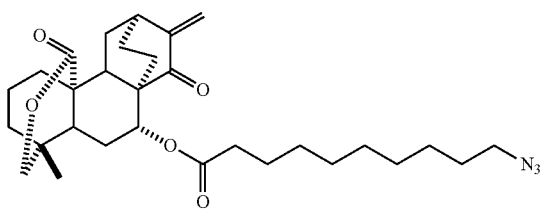

Compound 3: ¹H NMR (300 MHz, CDCl₃) δ: 5.89 (1H, s), 5.30 (1H, m), 5.20 (1H, s), 4.19 (1H, d, J=11.7 Hz), 4.08 (1H, d, J=11.7 Hz), 0.92 (3H, s). ESIMS: m/z 526.3 (M+H)⁺.

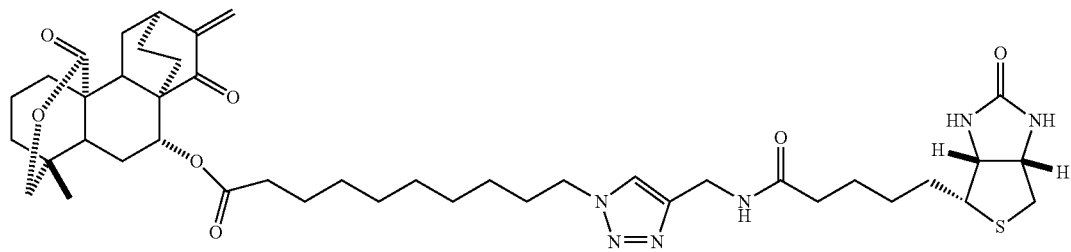

Compound 5: ¹H NMR (300 MHz, CDCl₃) δ: 5.9 (1H, s), 5.29 (1H, m), 5.21 (1H, s), ESIMS: m/z 829.4 (M+Na)⁺.

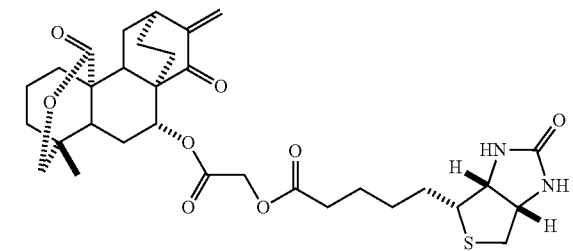

Compound 6: ¹H NMR (400 MHz, CDCl₃) δ: 5.93 (1H, d, J=1.6 Hz), 5.83 (1H, brs), 5.41 (1H, dd, J=4.4, 11.2 Hz), 5.15 (1H, brs), 4.57 (1H, s), 4.55 (1H, s), 4.51 (1H, m), 4.36 (1H, m), 4.23 (1H, dd, J=2.0, 12.0 Hz), 4.11 (1H, d, J=12.0 Hz), 3.10-3.19 (2H, m), 2.92 (1H, dd, J=4.8, 12.8 Hz), 2.81 (1H, brs), 2.74 (1H, d, J=12.8 Hz), 2.45 (1H, t, J=7.2 Hz), 2.13-2.24 (4H, m), 1.18-1.89 (19H, m), 0.95 (3H, s). ¹³C NMR (100 MHz, CDCl₃) δ: 200.3, 173.9, 172.9, 167.2, 163.4, 147.3, 117.2, 77.2, 76.4, 71.9, 61.7, 60.5, 60.0, 55.4, 48.6, 46.1, 45.6, 44.4, 40.5, 37.2, 35.6, 33.4, 32.8, 28.1, 28.0, 26.9, 25.7, 24.6, 23.6, 23.4, 20.1, 17.2. HREIMS m/z 614.2651 [M]⁺ ($C_{32}H_{42}N_2O_5S$, calcd. 614.2662).

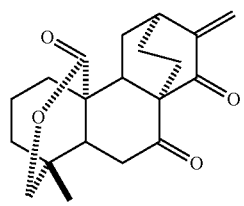

Compound 7: ¹H NMR (400 MHz, CDCl₃) δ: 6.05 (1H, d, J=1.2 Hz), 5.34 (1H, d, J=1.2 Hz), 4.24 (1H, dd, J=2.4, 12.4 Hz), 4.16 (1H, d, J=12.4 Hz), 2.86-2.91 (2H, m), 2.78 (1H, dd, J=6.0, 18.0 Hz), 2.05-2.32 (5H, m), 1.66-1.95 (7H, m), 1.48-1.50 (1H, m), 1.25-1.38 (2H, m), 0.91 (3H, s). ¹³C NMR (100 MHz, CDCl₃) δ: 206.2, 195.9, 173.2, 146.6, 119.4, 76.0, 57.5, 45.8, 44.9, 44.8, 40.4, 38.2, 36.6, 35.9, 33.1, 27.2, 25.9, 24.3, 22.8, 20.1. HREIMS m/z 328.1673 [M]⁺ ($C_{20}H_{24}O_4$, calcd. 328.1675).

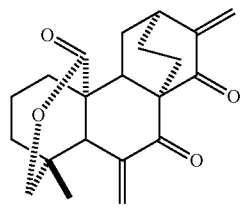

Compound 8: ¹H NMR (400 MHz, CDCl₃) δ: 5.98 (1H, s), 5.93 (1H, s), 5.34 (1H, s), 5.26 (1H, s), 3.93 (2H, s), 2.83 (1H, d, J=3.2 Hz), 2.68 (1H, t, J=11.2 Hz), 2.52 (1H, d, J=1.2 Hz), 2.16-2.22 (3H, m), 2.01-2.08 (1H, m), 1.87-1.97 (2H, m), 1.54-1.82 (5H, m), 1.35 (1H, ddd, J=4.4, 12.4, 16.8 Hz), 0.94 (3H, s). ¹³C NMR (100 MHz, CDCl₃) δ: 202.3, 195.7, 173.3, 146.2, 144.8, 125.8, 119.9, 75.4, 57.8, 53.5, 44.7, 42.5, 39.5, 36.3, 36.2, 35.0, 27.3, 25.9, 24.3, 20.9, 20.8. HREIMS m/z 340.1682 [M]$^+$ (C$_{21}$H$_{24}$O$_4$, calcd. 340.1675).

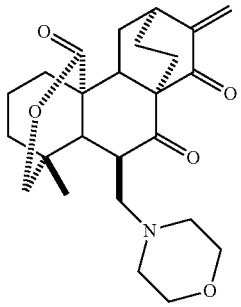

Compound 9: $^1$H NMR (400 MHz, CDCl$_3$) δ: 6.02 (1H, s), 5.37 (1H, s), 4.17 (1H, d, J=12.0 Hz), 4.02 (1H, d, J=12.0 Hz), 3.71 (4H, t, J=4.4 Hz), 2.85 (1H, d, J=2.4 Hz), 2.66-2.75 (3H, m), 2.53 (4H, brs), 2.10-2.53 (5H, m), 1.89-2.01 (2H, m), 1.62-1.82 (3H, m), 1.53-1.60 (3H, m), 1.31-1.35 (1H, m), 0.92 (3H, s). $^{13}$C NMR (100 MHz, CDCl3) δ: 208.2, 197.0, 173.0, 146.6, 119.7, 75.5, 68.8 (2CH2-morpholine), 63.5, 58.2, 53.6 (2CH2-morpholine), 52.5, 47.4, 44.6, 42.5, 40.4, 37.1, 36.3, 34.4, 27.6, 26.0, 22.5, 22.3, 20.6. HREIMS m/z 427.2366 [M]$^+$ (C$_{25}$H$_{33}$NO$_5$, calcd. 427.2359).

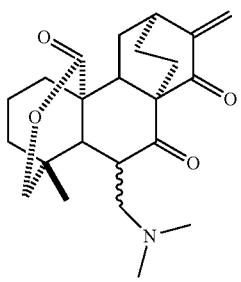

Compound 10: $^1$H NMR (400 MHz, CDCl$_3$) δ: 6.04 (1H, d, J=1.6 Hz), 5.39 (1H, d, J=1.6 Hz), 4.22 (1H, dd, J=2.4, 12.0 Hz), 4.04 (1H, dd, J=1.6, 12.0 Hz), 2.40-2.90 (6H, m), 2.38 (6H, s), 1.25-2.29 (13H, m), 0.91 (3H, s). HREIMS m/z 385.2266 [M]$^+$ (C$_{23}$H$_{31}$NO$_4$, calcd. 385.2253).

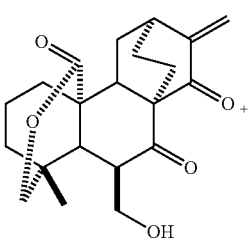

Compound 11: $^1$H NMR (400 MHz, CDCl$_3$) δ: 6.10 (1H, s), 5.47 (1H, s), 4.16 (1H, d, J=12.0 Hz), 4.06 (1H, d, J=12.0 Hz), 3.88 (1H, m), 3.61 (1H, m), 2.88 (1H, m), 2.81 (1H, m), 2.63-2.69 (3H, m), 2.34 (1H, t, J=10.0, 10.0 Hz), 2.20-2.28 (2H, m), 1.92-2.12 (3H, m), 1.49-1.84 (6H, m), 1.34-1.42 (1H, m), 0.90 (3H, s). $^{13}$C NMR (100 MHz, CDCl$_3$) δ: 210.4, 198.8, 172.7, 145.8, 121.1, 75.2, 65.9, 58.2, 52.6, 48.5, 44.0, 42.2, 40.1, 36.4, 35.9, 33.6, 27.1, 25.9, 22.2, 21.7, 20.2. HREIMS m/z 358.1791 [M]$^+$ (C$_{21}$H$_{26}$O$_5$, calcd. 358.1980).

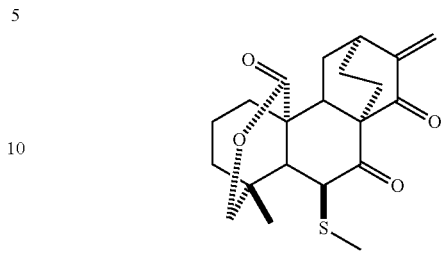

Compound 12: $^1$H NMR (400 MHz, CDCl$_3$) δ: 6.04 (1H, d, J=1.6 Hz), 5.36 (1H, d, J=1.6 Hz), 4.22 (1H, dd, J=2.0, 12.0 Hz), 4.09 (1H, dd, J=1.2, 12.0 Hz), 3.08 (1H, d, J=4.8 Hz), 2.86 (1H, m), 2.67 (1H, m), 2.50 (1H, t, J=10.0, 10.0 Hz), 2.21-2.29 (2H, m), 2.17 (3H, s), 1.90-2.11 (3H, m), 1.68-1.84 (2H, m), 1.53-1.67 (4H, m), 1.30-1.38 (1H, ddd, J=4.4, 11.0, 15.2 Hz), 1.02 (3H, s). $^{13}$C NMR (100 MHz, CDCl$_3$) δ: 200.4, 197.1, 172.8, 146.6, 119.5, 75.5, 57.4, 54.8, 48.9, 44.5, 44.0, 40.3, 40.2, 36.8, 34.0, 27.6, 25.8, 23.6, 22.2, 20.5, 16.2. HREIMS m/z 374.1536 [M]$^+$ (C$_2$H$_{26}$O$_4$S, calcd. 374.1552).

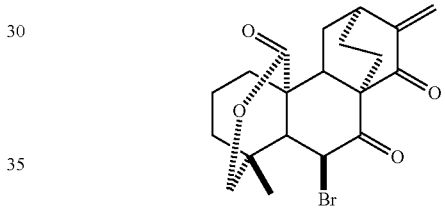

Compound 13: $^1$H NMR (400 MHz, CDCl$_3$) δ: 6.11 (1H, d, J=1.2 Hz), 5.42 (1H, d, J=1.2 Hz), 4.20 (1H, d, J=4.8 Hz), 4.19 (1H, d, J=1.6 Hz), 4.10 (1H, dd, J=1.6, 12.4 Hz), 2.90 (1H, d, J=3.2 Hz), 2.67 (1H, m), 2.56 (1H, m), 2.50 (1H, m), 2.21-2.29 (2H, m), 1.41-2.10 (9H, m), 1.12 (3H, s). $^{13}$C NMR (100 MHz, CDCl$_3$) δ: 199.8, 194.8, 172.1, 145.7, 120.3, 75.3, 59.1, 58.4, 45.0, 43.3, 41.0, 40.3, 36.9, 36.0, 34.1, 27.5, 25.8, 23.3, 22.4, 20.2. HREIMS m/z 406.0786 [M]$^+$ (C$_{20}$H$_{23}$BrO$_4$, calcd. 406.0780).

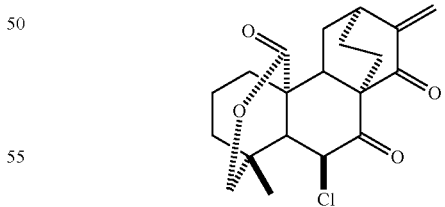

Compound 14: $^1$H NMR (400 MHz, CDCl$_3$) δ: 6.10 (1H, d, J=1.2 Hz), 5.42 (1H, d, J=1.2 Hz), 4.09-4.16 (3H, m), 2.89 (1H, s), 2.67 (1H, t, J=11.6 Hz), 2.54 (1H, t, J=9.6 Hz), 2.22-2.99 (3H, m), 1.92-2.13 (3H, m), 1.81-1.85 (2H, m), 1.59-1.70 (4H, m), 1.42 (1H, m), 1.25 (1H, m), 1.08 (1H, s). $^{13}$C NMR (100 MHz, CDCl$_3$) δ: 199.9, 194.9, 172.1, 146.0, 120.4, 75.6, 58.9, 58.8, 54.6, 44.5, 41.3, 40.3, 37.0, 36.2, 33.9, 27.5, 25.9, 23.2, 22.5, 20.3. HREIMS m/z 362.1287 [M]$^+$ (C$_{20}$H$_{23}$ClO$_4$, calcd. 362.1285).

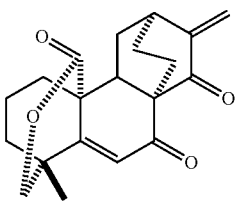

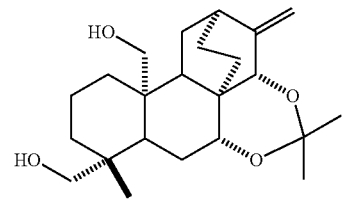

Compound 15: $^1$H NMR (400 MHz, CDCl$_3$) δ: 6.13 (1H, s), 6.02 (1H, d, J=1.6 Hz), 5.31 (1H, d, J=1.6 Hz), 4.27 (1H, d, J=10.8 Hz), 3.83 (1H, dd, J=2.4, 10.8 Hz), 3.26 (1H, m), 2.88 (1H, t, J=2.8 Hz), 2.49-2.54 (2H, m), 2.17 (1H, m), 1.70-1.96 (7H, m), 1.56 (1H, m), 1.18 (3H, s). $^{13}$C NMR (100 MHz, CDCl$_3$) δ: 196.9, 195.6, 171.5, 159.8, 147.3, 123.4, 118.4, 79.8, 54.9, 47.6, 42.5, 39.9, 38.8 (C$_t$ and C$_s$), 35.8, 25.5, 24.5, 23.4, 21.8, 19.5. HREIMS m/z 326.1512 [M]$^+$ (C$_{20}$H$_{22}$O$_4$, calcd. 326.1518).

Compound 18: $^1$H NMR (400 MHz, CDCl$_3$) δ: 5.02 (1H, d, J=2.0 Hz), 4.12 (1H, d, J=12.4 Hz), 3.93 (3H, m), 3.46 (2H, m), 2.46 (2H, brs), 2.30 (1H, s), 1.90-2.10 (3H, m), 1.40-1.74 (12H, m), 1.11-1.28 (5H, m), 1.05 (3H, s), 0.80-0.88 (2H, m). 13C NMR (100 MHz, CDCl3) δ: 151.4, 109.6, 100.5, 78.9, 76.6, 68.6, 63.0, 54.2, 49.7, 41.7, 38.2, 37.8, 37.1, 36.7, 35.8, 30.0, 28.5, 27.0, 26.8, 25.7, 20.1, 18.8, 14.0. ESI-MS: m/z 399.5 [M+Na]$^+$.

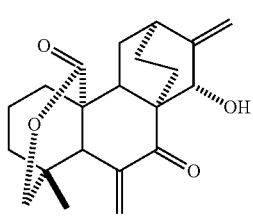

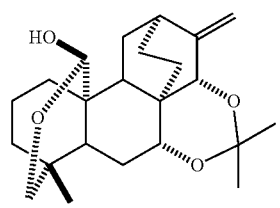

Compound 16: $^1$H NMR (400 MHz, CDCl$_3$) δ: 5.89 (1H, s), 5.43 (1H, s), 5.10 (1H, brs), 4.08 (1H, d, J=11.6 Hz), 4.00 (1H, d, J=11.6 Hz), 3.95 (1H, s), 2.70 (1H, s), 2.64 (1H, t, J=10.8 Hz), 2.51 (1H, brs), 2.47 (1H, brs), 2.46 (1H, d, J=13.2 Hz), 2.17 (2H, s), 2.05-2.13 (1H, m), 1.56-1.83 (8H, m), 1.32-1.38 (1H, m), 1.03 (3H, s). $^{13}$C NMR (100 MHz, CDCl$_3$) δ: 208.5, 173.4, 151.2, 144.1, 125.8, 112.6, 75.3, 74.8, 53.0, 44.1, 40.2, 36.6, 35.5, 27.8, 25.1, 24.3, 20.8, 17.0. HREIMS m/z 342.1839 [M]$^+$ (C$_{21}$H$_{26}$O$_4$, calcd. 342.1831).

Compound 19: $^1$H NMR (400 MHz, CDCl$_3$) δ: 5.60 (1H, d, J=4.4 Hz), 4.99 (2H, s), 3.94 (1H, s), 3.60-3.67 (2H, m), 3.53 (1H, d, J=11.2 Hz), 3.18 (1H, brs), 2.47-2.53 (1H, m), 2.11-2.41 (4H, m), 1.25-1.79 (8H, m), 1.55 (3H, s), 1.48 (3H, s), 1.05-1.09 (1H, m), 0.78-0.93 (3H, m), 0.73 (3H, s), $^{13}$C NMR (100 MHz, CDCl$_3$) δ: 151.8, 109.1, 100.4, 97.1, 76.8, 76.7, 71.6, 50.7, 46.2, 41.8, 40.9, 36.9, 36.0, 34.0, 33.2, 30.0, 26.3, 25.6, 23.4, 23.2, 21.9, 20.0, 16.8. ESI MS: m/z 397.2 [M+Na]$^+$.

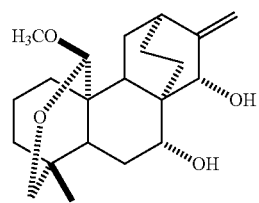

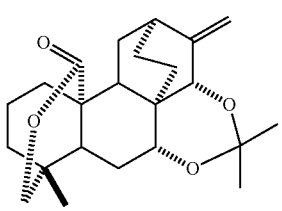

Compound 17: $^1$H NMR (400 MHz, CDCl$_3$) δ: 5.01 (1H, s), 4.97 (1H, s), 4.24 (1H, dd, J=2.4, 11.6 Hz), 4.07 (1H, d, J=11.6 Hz), 3.99 (1H, d, J=2.0 Hz), 3.60 (1H, dd, J=4.0, 11.6 Hz), 2.98 (1H, m), 2.30 (1H, m), 1.96 (1H, m), 1.97 (2H, m), 1.36-1.78 (8H, m), 1.55 (3H, s), 1.48 (3H, s), 1.17-1.28 (3H, m), 0.93 (3H, s), 0.83-0.89 (1H, m). $^{13}$C NMR (100 MHz, CDCl$_3$) δ: 174.2, 151.8, 108.7, 100.4, 76.7, 75.7, 75.5, 48.3, 45.9, 45.5, 40.7, 38.3, 36.7, 35.9, 33.0, 30.0, 26.1, 25.3, 24.4, 23.9, 20.4, 19.9, 14.6. ESI-MS: m/z 395.1 [M+Na]$^+$.

Compound 20: $^1$H NMR (400 MHz, CDCl$_3$) δ: 5.08 (1H, s), 5.01 (1H, s), 4.98 (1H, s), 3.92 (2H, s), 3.72 (1H, dd, J=4.8, 11.6 Hz), 3.65 (1H, dd, J=2.4, 11.6 Hz), 3.53 (1H, dd, J=1.2, 11.6 Hz), 3.46 (3H, s), 2.55 (1H, brs), 2.43 (1H, m), 2.28-2.41 (3H, m), 1.87-1.93 (1H, m), 1.24-1.84 (9H, m), 1.16-1.22 (1H, m), 0.94-0.99 (1H, m), 0.77-0.89 (1H, m), 0.73 (3H, s). ESI-MS: m/z 371.2 [M+Na]$^+$.

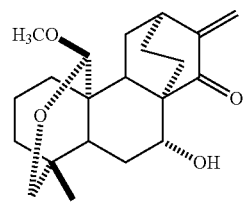

Compound 21: $^1$H NMR (400 MHz, CDCl$_3$) δ: 5.96 (1H, d, J=1.6 Hz), 5.25 (1H, d, J=1.6 Hz), 5.11 (1H, s), 4.18 (1H, dd, J=4.8, 12.0 Hz), 3.66 (1H, dd, J=2.4, 11.2 Hz), 3.55 (1H, dd, J=1.2, 11.2 Hz), 3.49 (3H, s), 2.73 (1H, brs), 2.64-2.72 (2H, m), 1.18-1.94 (14H, m), 0.78 (1H, m), 0.75 (3H, s). $^{13}$C NMR (100 MHz, CDCl$_3$) δ: 204.5, 147.2, 117.5, 103.7, 71.3, 70.5, 55.9, 50.5, 49.0, 43.6, 41.9, 40.7, 35.8, 34.2, 33.0, 27.1, 24.9, 24.1, 23.1, 21.9, 18.7. HREIMS m/z 346.2122 [M]$^+$ (C$_{21}$H$_{30}$O$_4$, calcd. 346.2144).

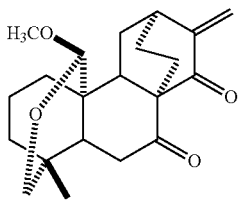

Compound 22: $^1$H NMR (400 MHz, CDCl$_3$) δ: 6.02 (1H, d, J=1.6 Hz), 5.32 (1H, d, J=1.6 Hz), 4.40 (1H, s), 3.45 (2H, m), 3.42 (3H, s), 2.77 (1H, brs), 2.48-2.64 (2H, m), 2.16-2.40 (4H, m), 1.96 (1H, t, J=10.4 Hz), 1.63-1.88 (6H, m), 1.51-1.54 (1H, m), 1.41-1.43 (1H, m), 0.97 (1H, m), 0.66 (3H, s). $^{13}$C NMR (100 MHz, CDCl$_3$) δ: 209.9, 196.7, 146.5, 119.3, 102.7, 70.4, 57.7, 55.5, 47.9, 45.7, 40.4, 39.7, 37.5, 35.7, 33.6, 31.2, 27.2, 26.8, 23.5, 21.6, 21.4. HREIMS m/z 344.1998 [M]$^+$ (C$_{21}$H$_{28}$O$_4$, calcd. 344.1988).

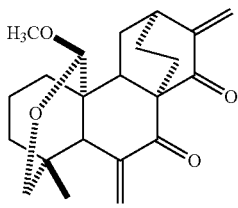

Compound 23: $^1$H NMR (400 MHz, CDCl$_3$) δ: 5.99 (1H, d, J=1.2 Hz), 5.98 (1H, dd, J=1.2, 2.4 Hz), 5.33 (1H, dd, J=1.2, 2.4 Hz), 5.32 (1H, d, J=1.2 Hz), 4.39 (1H, d, J=1.2 Hz), 3.46 (1H, dd, J=1.8, 11.2 Hz), 3.43 (3H, s), 3.27 (1H, dd, J=1.8, 11.2 Hz), 2.78 (1H, d, J=3.0 Hz), 2.33-2.45 (4H, m), 2.15 (1H, t, J=10.4 Hz), 1.94 (1H, t, J=10.4 Hz), 1.52-1.88 (7H, m), 1.07 (1H, m), 0.84 (3H, s). $^{13}$C NMR (100 MHz, CDCl$_3$) δ: 203.3, 196.3, 146.6, 145.5, 126.2, 119.3, 103.3, 71.6, 57.0, 55.2, 54.8, 44.2, 41.0, 39.2, 35.9, 35.5, 30.6, 27.4, 26.6, 24.0, 22.7, 21.3. HREIMS m/z 356.1985 [M]$^+$ (C$_{22}$H$_{28}$O$_4$, calcd. 356.1988).

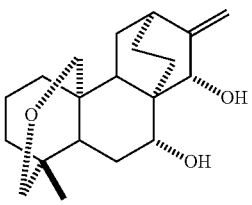

Compound 24: $^1$H NMR (400 MHz, CDCl$_3$) δ: 5.04 (1H, s), 5.01 (1H, s), 4.06 (1H, dd, J=3.2, 11.6 Hz), 3.78-3.92 (3H, m), 3.68-3.72 (1H, m), 3.52 (1H, dd, J=2.8, 11.6 Hz), 3.43 (1H, d, J=11.6 Hz), 2.88 (1H, brs), 2.31-2.42 (2H, m), 1.87-2.02 (2H, m), 1.34-1.74 (10H, m), 1.15-1.20 (1H, m), 0.96-1.18 (2H, m), 0.71 (3H, s). ESI-MS: m/z 341.2 [M+Na]$^+$.

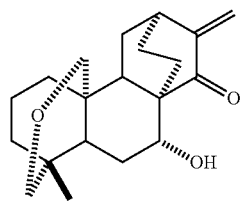

Compound 25: $^1$H NMR (400 MHz, CDCl$_3$) δ: 6.00 (1H, d, J=1.6 Hz), 5.29 (1H, d, J=1.6 Hz), 4.13 (1H, dddd, J=2.8, 5.2, 11.6, 12.8 Hz), 4.07 (1H, dd, J=2.8, 11.6 Hz), 3.87 (1H, d, 11.6 Hz), 3.54 (1H, dd, J=2.8, 11.6 Hz), 3.47 (1H, d, 11.6 Hz), 2.77 (1H, brs), 2.64 (1H, d, J=3.2 Hz), 2.33-2.41 (1H, m), 1.97-2.17 (2H, m), 0.78-1.83 (13H, m), 0.73 (3H, s). $^{13}$C NMR (100 MHz, CDCl3) δ: 203.8, 146.3, 118.5, 73.0, 70.5, 67.5, 50.0, 47.3, 42.2, 40.8, 39.3, 38.3, 35.8, 33.0, 27.3, 25.1, 24.6, 23.4, 22.2, 18.7. HREIMS m/z 316.2043 [M]$^+$ (C$_{20}$H$_{28}$O$_3$, calcd. 316.2038).

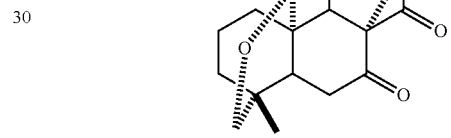

Compound 28: $^1$H NMR (400 MHz, CDCl$_3$) δ: 6.04 (1H, s), 5.33 (1H, s), 3.90 (1H, d, J=11.2 Hz), 3.76 (1H, dd, J=2.4, 11.2 Hz), 3.45 (2H, s), 2.82 (1H, d, J=2.4 Hz), 2.58 (1H, d, J=9.2 Hz), 2.38-2.46 (1H, m), 2.08-2.18 (2H, m), 1.39-1.98 (11H, m), 1.14-1.23 (1H, m), 0.66 (3H, s). $^{13}$C NMR (100 MHz, CDCl$_3$) δ: 208.6, 195.6, 145.8, 119.6, 71.7, 66.9, 56.9, 45.6, 45.0, 40.4, 37.4, 37.2, 36.9, 35.5, 33.3, 26.9, 26.1, 25.1, 22.3, 21.8. HREIMS m/z 314.1889 [M]$^+$ (C$_{20}$H$_{26}$O$_3$, calcd. 314.1882).

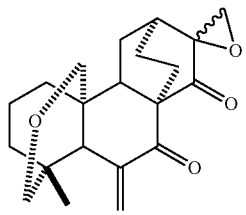

Compound 29: $^1$H NMR (400 MHz, CDCl$_3$) δ: 5.98 (1H, s), 5.35 (1H, s), 3.97 (1H, d, J=12.0 Hz), 3.53 (1H, dd, J=2.8, 12.0 Hz), 3.43 (1H, dd, J=1.2, 11.6 Hz), 3.14 (1H, dd, J=3.2, 11.6 Hz), 3.12 (1H, d, J=6.0 Hz), 2.87 (1H, d, J=6.0 Hz), 2.42-2.57 (2H, m), 2.41 (1H, brs), 2.07-2.18 (3H, m), 1.52-1.99 (9H, m), 1.53 (1H, m), 1.34-1.36 (1H, m), 0.83 (3H, s). $^{13}$C NMR (100 MHz, CDCl$_3$) δ: 203.8, 201.1, 145.1, 126.9, 73.9, 68.9, 60.3, 58.0, 53.2, 52.8, 43.1, 41.0, 37.2, 35.4, 34.1, 24.5, 24.3, 24.1, 23.4, 21.7. HREIMS m/z 342.1840 [M]$^+$ (C$_{21}$H26O4, calcd. 342.1831).

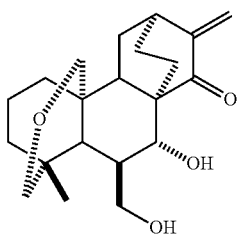

Compound 30: 1H NMR (400 MHz, CDCl3) δ: 6.07 (1H, d, J=0.8 Hz), 5.41 (1H, d, J=0.8 Hz), 3.82-3.89 (2H, m), 3.55 (1H, m), 3.52 (1H, d, J=10.8 Hz), 3.29-3.36 (2H, m), 2.85 (1H, brs), 2.67-2.71 (2H, m), 2.36-2.47 (2H, m), 2.02-2.13 (2H, m), 1.93-1.99 (1H, m), 1.70-1.80 (3H, m), 1.56-1.63 (2H, m), 1.44-1.52 (3H, m), 1.25-1.30 (1H, m), 0.70 (3H, s). $^{13}$C NMR (100 MHz, CDCl$_3$) δ: 212.2, 198.8, 145.6, 120.7, 72.8, 68.9, 66.1, 57.6, 52.2, 49.3, 43.7, 40.6, 37.4, 35.8, 35.6, 34.2, 26.8, 25.8, 24.1, 21.8, 21.6. HREIMS m/z 344.1989 [M]$^+$ (C$_{21}$H$_{28}$O$_4$, calcd. 344.1988).

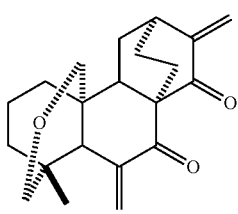

Compound 31: $^1$H NMR (400 MHz, CDCl$_3$) δ: 5.99 (2H, s), 5.35 (1H, s), 5.33 (1H, s), 3.93 (1H, d, J=11.6 Hz), 3.53 (1H, dd, J=2.4, 11.6 Hz), 3.42 (1H, d, J=11.6 Hz), 3.13 (1H, dd, J=2.4, 11.6 Hz), 2.83 (1H, d, J=2.4 Hz), 2.41-2.50 (3H, m), 1.47-2.06 (10H, m), 1.25-1.34 (1H, m), 0.83 (3H, s). $^{13}$C NMR (100 MHz, CDCl$_3$) δ: 202.7, 195.8, 145.9, 145.7, 126.4, 119.3, 73.9, 69.2, 57.0, 53.2, 44.0, 41.1, 37.1, 35.7, 35.5, 35.4, 26.8, 26.1, 24.3, 23.7, 21.7. HREIMS m/z 326.1879 [M]$^+$ (C$_{21}$H$_{26}$O$_3$, calcd. 326.1882).

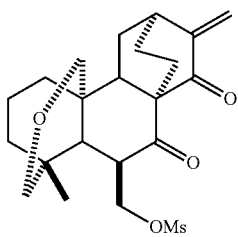

Compound 32: $^1$H NMR (400 MHz, CDCl$_3$) δ: 6.00 (1H, s), 5.34 (1H, s), 4.32 (1H, dd, J=3.6, J=9.6 Hz), 4.25 (1H, dd, J=5.6, 9.6 Hz), 3.91 (1H, d, J=11.2 Hz), 3.49 (1H, d, J=12.0 Hz), 3.30-3.37 (2H, m), 3.12 (3H, s), 2.77-2.82 (2H, m), 2.34-2.45 (2H, m), 2.04-2.17 (2H, m), 1.96-1.97 (1H, m), 1.46-1.81 (8H, m), 1.25-1.31 (1H, m), 0.73 (3H, s). $^{13}$C NMR (100 MHz, CDCl$_3$) δ: 209.0, 195.6, 145.8, 119.7, 72.5, 72.0, 68.8, 57.8, 48.5, 47.5, 42.8, 40.6, 37.3, 36.9, 35.8, 35.5, 34.3, 26.6, 26.1, 25.3, 22.1, 21.6. HREIMS m/z 422.1759 [M]$^+$ (C$_{22}$H$_{30}$O$_6$S, calcd. 422.1763).

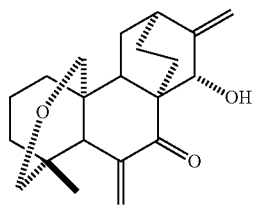

Compound 33: $^1$H NMR (400 MHz, CDCl$_3$) δ: 5.94 (1H, s), 5.46 (1H, s), 5.08 (2H, s), 3.93 (1H, s), 3.91 (1H, d, J=12.0 Hz), 3.58 (1H, dd, J=2.8, 12.0 Hz), 3.44 (1H, d, J=11.2 Hz), 3.25 (1H, dd, J=2.8, 11.2 Hz), 2.34-2.49 (4H, m), 2.03 (1H, m), 1.21-2.06 (11H, m), 0.86 (3H, s). $^{13}$C NMR (100 MHz, CDCl$_3$) δ: 209.4, 150.0, 144.8, 126.8, 113.1, 74.5, 73.7, 69.6, 53.2, 48.6, 44.9, 41.6, 36.7, 35.7, 35.3, 35.2, 26.6, 25.6, 24.4, 21.8, 20.3. HREIMS m/z 328.2040 [M]$^+$ (C$_{21}$H$_{28}$O$_3$, calcd. 328.2038).

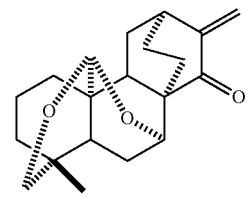

Compound 35: $^1$H NMR (400 MHz, CDCl$_3$) δ: 5.21 (1H, s), 5.06 (1H, s), 5.04 (1H, s), 3.98 (1H, s), 3.92 (1H, d, J=4.8 Hz), 3.85 (1H, dd, J=7.2, 11.6 Hz), 3.28 (1H, d, J=11.6 Hz), 2.47 (1H, t, J=4.4 Hz), 2.19-2.29 (1H, m), 1.96-2.02 (1H, m), 1.10-1.94 (14H, m), 0.80-0.89 (1H, m), 0.70 (3H, s). ESI-MS: m/z 339.5 [M+Na]$^+$.

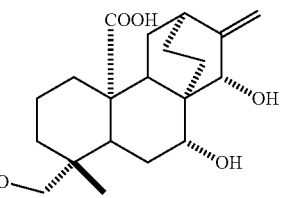

Compound 36: $^1$H NMR (400 MHz, CDCl$_3$) δ: 5.93 (1H, d, J=1.6 Hz), 5.25 (1H, d, J=2.0 Hz), 5.24 (1H, d, J=1.6 Hz), 4.12 (1H, d, J=5.2 Hz), 3.86 (1H, dd, J=3.2, 11.6 Hz), 3.30 (1H, dd, J=1.6, 11.6 Hz), 2.81 (1H, m), 2.25-2.35 (2H, m), 2.02-2.08 (1H, m), 1.48-1.91 (10H, m), 1.17-1.27 (3H, m), 0.69 (3H, s). $^{13}$C NMR (100 MHz, CDCl$_3$) δ: 200.7, 148.0, 117.4, 96.3, 68.9, 66.1, 49.1, 43.7, 43.4, 40.3, 36.7, 34.7, 33.7, 29.6, 27.3, 24.5, 24.1, 23.5, 22.5, 20.8. HREIMS m/z 314.1882 [M]$^+$ (C$_{20}$H$_{26}$O$_3$, calcd. 314.1882).

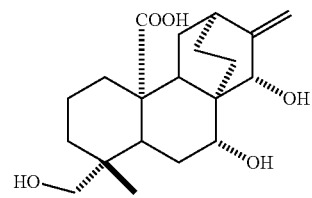

Compound 37: ¹H NMR (400 MHz, DMSO) δ: 12.52 (1H, s), 5.53 (1H, d, J=3.6 Hz), 4.89 (1H, s), 4.85 (1H, s), 4.58 (1H, s), 4.09 (1H, s), 3.73 (1H, s), 3.52 (1H, m), 3.35 (1H, m), 3.12 (1H, m), 2.27-2.36 (2H, m), 2.19 (1H, s), 1.15-1.94 (11H, m), 0.88 (3H, s), 0.699-0.85 (2H, m). ¹³C-NMR (100 MHz, DMSO) δ: 177.3, 155.0, 108.1, 80.0, 78.1, 62.7, 52.3, 48.3, 47.5, 41.4, 38.3, 37.7, 35.3, 35.0, 27.2, 27.0, 26.9, 26.1, 19.5, 12.7. ESI-MS: m/z 373.2 [M+Na]⁺.

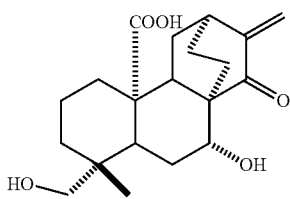

Compound 38: ¹H NMR (400 MHz, CD₃OD) δ: 5.89 (1H, d, J=3.2 Hz), 5.26 (1H, d, J=3.2 Hz), 4.10 (1H, dd, J=4.8, 12.0 Hz), 3.49 (1H, d, J=11.6 Hz), 3.41 (1H, d, J=11.6 Hz), 2.73 (1H, brs), 2.14-2.57 (3H, m), 1.97-2.03 (1H, m), 1.42-1.90 (10H, m), 1.21-1.28 (1H, m), 0.99 (3H, s), 0.97 (1H, m), 0.80 (1H, td, J=3.6, 12.8 Hz). ¹³C NMR (100 MHz, CD₃OD) δ: 203.7, 179.1, 149.0, 117.9, 71.5, 65.3, 53.9, 51.7, 50.3, 46.7, 39.7, 36.5, 30.7, 29.4, 28.0, 27.3, 26.5, 24.2, 20.8, 17.2. HREIMS m/z 348.1937 [M]⁺ (C₂₀H₂₈O₅, calcd. 348.1937).

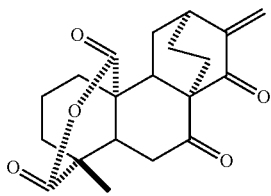

Compound 39: ¹H NMR (400 MHz, CDCl₃) δ: 6.08 (1H, s), 5.39 (1H, s), 2.71-2.91 (3H, m), 2.41-2.22 (1H, m), 2.23 (1H, t, J=9.6 Hz), 1.47-2.13 (12H, m), 1.30 (3H, s). ¹³C NMR (100 MHz, CDCl₃) δ: 203.5, 194.9, 170.5, 169.8, 146.1, 120.2, 57.2, 45.8, 45.5, 44.8, 44.0, 39.1, 37.3, 35.7, 35.4, 26.8, 25.9, 24.9, 21.7, 19.9. HREIMS m/z 342.1456 [M]⁺ (C₂₀H₂₂O₅, calcd. 342.1467).

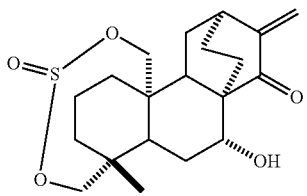

Compound 41: ¹H NMR (400 MHz, CDCl₃) δ: 6.00 (1H, d, J=1.6 Hz), 5.29 (1H, d, J=1.6 Hz), 4.81 (1H, d, J=14.0 Hz), 4.16 (1H, dd, J=6.4, 12.4 Hz), 4.02 (1H, d, J=12.4 Hz), 3.95 (1H, d, J=14.0 Hz), 3.61 (1H, brs), 2.82 (1H, m), 2.74 (1H, d, J=2.0 Hz), 2.18-2.26 (3H, m), 1.71-1.86 (6H, m), 1.66 (1H, d, J=14.0 Hz), 1.43-1.55 (3H, m), 1.35 (1H, ddd, J=4.0, 14.4 Hz), 1.79 (1H, d, J=12.0 Hz), 0.85-0.91 (4H, m).

¹³C NMR (100 MHz, CDCl₃) δ: 204.8, 146.7, 117.9, 77.2, 71.2, 58.2, 51.3, 50.4, 46.0, 38.8, 38.5, 36.1, 35.4, 30.9, 28.7, 28.1, 25.3, 25.0, 19.1, 15.5. HREIMS m/z 380.1651 [M]⁺ (C₂₀H₂₈O₅S, calcd. 380.1657).

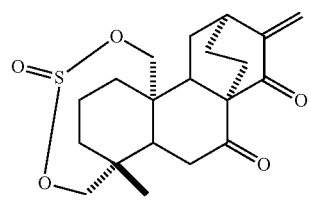

Compound 42: ¹H NMR (400 MHz, CDCl₃) δ: 6.07 (1H, s), 5.37 (1H, s), 5.00 (1H, brs), 3.00-4.20 (3H, brs), 2.87 (1H, brs), 2.53 (1H, m), 0.86-2.26 (18H, m). ¹³C NMR (100 MHz, CDCl₃) δ: 207.7, 195.8, 145.9, 119.8, 63.2, 57.4, 50.0, 46.8, 38.7, 38.2, 37.7, 36.3, 35.4, 27.7, 27.2, 26.9, 26.8, 23.2, 18.7. HREIMS m/z 378.1504 [M]⁺ (C₂₀H₂₆O₅S, calcd. 378.1501).

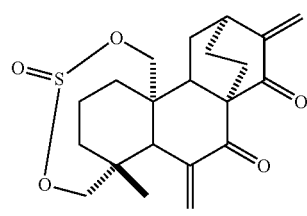

Compound 43: ¹H NMR (400 MHz, CDCl₃) δ: 6.14 (1H, d, J=2.4 Hz), 6.04 (1H, d, J=1.2 Hz), 5.80 (1H, d, J=2.4 Hz), 5.36 (1H, d, J=1.2 Hz), 4.86 (1H, d, J=13.6 Hz), 4.02 (1H, brs), 3.87 (1H, d, J=13.6 Hz), 2.87 (1H, m), 2.65 (1H, m), 2.22-2.36 (2H, m), 1.15-2.14 (15H, m). ¹³C NMR (125 MHz, CDCl₃) δ: 198.7, 195.5, 146.3, 146.1, 124.2, 119.7, 66.4, 57.7, 56.2, 54.5, 45.2, 38.5, 37.9, 35.8, 32.5, 31.7, 29.2, 27.3, 26.9, 22.4, 18.1. HREIMS m/z 390.1512 [M]⁺ (C₂₁H₂₆O₅S, calcd. 390.1501).

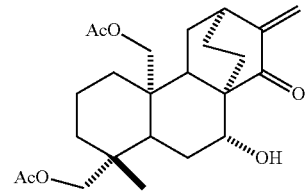

Compound 45: ¹H NMR (400 MHz, CDCl₃) δ: 5.98 (1H, d, J=1.2 Hz), 5.28 (1H, d, J=1.2 Hz), 4.59 (1H, d, J=13.2 Hz), 4.25 (1H, d, J=13.2 Hz), 4.10 (1H, m), 3.99 (1H, d, J=11.2 Hz), 2.79 (1H, s), 2.48 (1H, s), 2.13 (3H, s), 2.06 (3H, s), 1.43-1.97 (15H, m), 1.12-1.16 (1H, m), 1.03 (3H, s), 0.82 (1H, m). ¹³C NMR (100 MHz, CDCl3) δ: 203.8, 171.1, 170.8, 146.7, 118.2, 71.2, 66.8, 63.3, 53.0, 50.5, 46.8, 41.5, 36.5, 36.4, 35.6, 35.3, 28.0, 27.5, 25.6, 25.0, 21.1, 20.9, 19.5, 18.0. HREIMS m/z 418.2341 [M]⁺ (C₂₄H₃₄O₆, calcd. 418.2355).

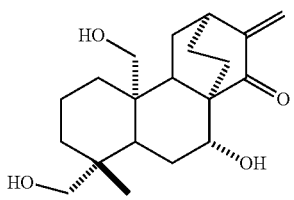

Compound 46: ¹H NMR (400 MHz, CD₃OD) δ: 5.90 (1H, d, J=1.6 Hz), 5.26 (1H, d, J=1.6 Hz), 4.05 (1H, dd, J=4.8, 12.0 Hz), 3.97 (1H, d, J=12.4 Hz), 3.91 (1H, d, J=12.4 Hz), 3.72 (1H, d, J=11.2 Hz), 3.57 (1H, d, J=11.2 Hz), 2.75 (1H, brs), 2.06-2.12 (4H, m), 1.66-1.92 (8H, m), 1.53-1.63 (1H, m), 1.28-1.41 (2H, m), 0.95-1.06 (3H, m), 0.99 (3H, s), 0.70 (1H, m). ¹³C NMR (100 MHz, CD₃OD) δ: 204.1, 149.3, 117.5, 71.6, 65.9, 62.3, 54.4, 51.6, 43.9, 39.2, 37.3, 37.2, 36.4, 29.0, 28.0, 27.8, 26.5, 20.5, 19.0. HREIMS m/z 334.2146 [M]⁺ (C₂₀H₃₀O₄, calcd. 334.2144).

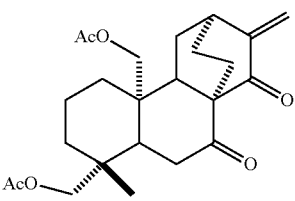

Compound 47: ¹H NMR (400 MHz, CDCl3) δ: 6.05 (1H, d, J=0.8 Hz), 5.35 (1H, d, J=0.8 Hz), 4.34 (1H, d, J=12.8 Hz), 4.17 (1H, d, J=12.8 Hz), 4.06 (1H, d, J=11.2 Hz), 3.99 (1H, d, J=11.2 Hz), 2.85 (1H, brs), 2.66 (1H, s), 2.63 (1H, s), 2.28 (1H, m), 2.07-2.13 (1H, m), 2.05 (3H, s), 2.02 (3H, s), 1.57-1.93 (10H, m), 1.03-1.09 (2H, m), 0.93 (3H, s). ¹³C NMR (100 MHz, CDCl₃) δ: 207.6, 196.1, 170.6, 170.1, 146.0, 119.3, 64.9, 63.6, 57.8, 51.5, 48.0, 38.5, 38.1, 36.6, 36.0, 35.4, 33.3, 26.8, 26.1, 25.7, 23.2, 20.6 (2CH3), 17.8. HREIMS m/z 416.2220 [M]⁺ (C₂₄H₃₂O₆, calcd. 416.2199).

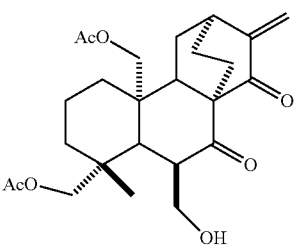

Compound 48: ¹H NMR (400 MHz, CDCl₃) δ: 5.99 (1H, d, J=1.2 Hz), 5.35 (1H, d, J=1.2 Hz), 4.19 (1H, d, J=13.2 Hz), 3.98 (1H, d, J=13.2 Hz), 3.93 (1H, d, J=11.6 Hz), 3.87 (1H, d, J=11.6 Hz), 3.83 (1H, d, J=4.0 Hz), 3.47 (1H, m), 2.81 (2H, m), 2.69 (1H, m), 2.12-2.26 (2H, m), 1.98 (3H, s), 1.94 (3H, s), 1.75-1.86 (1H, m), 1.69-1.73 (2H, m), 1.43-1.63 (7H, m), 0.99-1.10 (1H, m), 0.93 (3H, s). ¹³C NMR (100 MHz, CDCl₃) δ: 208.9, 199.1, 170.8, 170.4, 145.8, 120.7, 65.8, 65.6, 63.3, 57.4, 54.0, 53.6, 44.9, 38.5, 37.8, 36.6, 35.6, 32.9, 27.1, 26.6, 26.4, 22.5, 20.8, 20.7, 17.8. HREIMS m/z 446.2305 [M]⁺ (C₂₅H₃₄O₇, calcd. 446.2305).

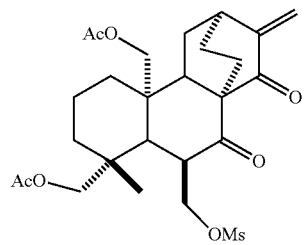

Compound 49: ¹H NMR (400 MHz, CDCl₃) δ: 5.94 (1H, s), 5.31 (1H, s), 4.43 (1H, dd, J=6.0, 10.0 Hz), 4.27 (1H, dd, J=2.4, 10.0 Hz), 4.23 (1H, d, J=13.2 Hz), 4.06 (1H, d, J=13.2 Hz), 3.99 (1H, d, J=11.6 Hz), 3.92 (1H, d, J=11.6 Hz), 3.07 (3H, s), 3.01 (1H, m), 2.80 (1H, brs), 2.13-2.27 (2H, m), 2.02 (3H, s), 1.95 (3H, s), 1.70-1.91 (2H, m), 1.58-1.68 (6H, m), 1.46 (1H, t, J=12.0 Hz), 1.07-1.21 (2H, m), 1.01 (3H, s), 0.82 (1H, m). ¹³C NMR (100 MHz, CDCl₃) δ: 206.7, 196.0, 170.8, 170.3, 146.3, 119.5, 71.9, 65.8, 63.6, 57.9, 52.3, 49.7, 44.2, 38.3, 38.1, 36.8 (3CH3), 35.6, 33.0, 27.1, 26.6, 26.5, 23.6, 20.8, 20.7, 17.8. HREIMS m/z 524.2072 [M]⁺ (C₂₆H₃₆O₉S, calcd. 524.2080).

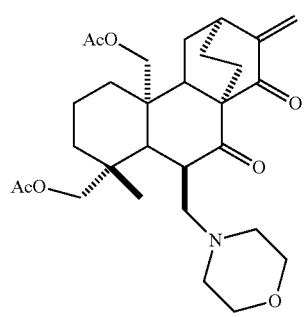

Compound 50: ¹H NMR (400 MHz, CDCl₃) δ: 5.92 (1H, d, J=1.2 Hz), 5.26 (1H, d, J=1.2 Hz), 4.22 (1H, d, J=13.2 Hz), 3.97 (1H, d, J=11.2 Hz), 3.92 (1H, d, J=13.2 Hz), 3.87 (1H, d, J=11.2 Hz), 3.64-3.71 (4H, m), 2.77-2.85 (1H, m), 2.57 (1H, brs), 2.05-2.53 (9H, m), 1.99 (3H, s), 1.96 (3H, s), 1.45-1.83 (9H, m), 1.39 (1H, d, J=7.6 Hz), 1.00-1.19 (1H, m), 0.98 (3H, s). ¹³C NMR (100 MHz, CDCl₃) δ: 205.1, 197.3, 170.8, 170.5, 146.5, 118.9, 66.8 (2CH2-morpholine), 65.9, 63.1, 62.5, 57.6, 57.1, 53.0 (2CH2-morpholine), 47.7, 45.5, 38.7, 38.1, 36.9, 35.7, 33.2, 26.9, 26.7, 26.6, 22.9, 20.8, 20.7, 17.8. HREIMS m/z 515.2879 [M]⁺ (C₂₉H₄₁NO₇, calcd. 515.2833).

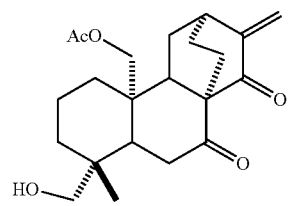

Compound 51: ¹H NMR (400 MHz, CDCl₃) δ: 6.04 (1H, s), 5.34 (1H, s), 4.30 (1H, d, J=12.8 Hz), 4.22 (1H, d, J=12.8 Hz), 3.60 (1H, d, J=11.2 Hz), 3.56 (1H, d, J=11.2 Hz), 2.83 (1H, brs), 2.58-2.77 (2H, m), 2.28 (1H, t, J=11.2 Hz), 2.02-2.13 (2H, m), 2.00 (3H, s), 1.52-1.93 (11H, m), 1.25

(1H, brs), 1.00-1.07 (2H, m), 0.96 (3H, s). $^{13}$C NMR (100 MHz, CDCl$_3$) δ: 208.4, 196.5, 170.5, 146.2, 119.5, 64.1, 64.0, 58.1, 51.8, 48.4, 38.7, 38.4, 38.1, 35.6, 33.6, 27.1, 26.3, 25.7, 23.5, 20.9, 18.0. HREIMS m/z 374.2082 [M]$^+$ (C$_{22}$H$_{30}$O$_5$, calcd. 374.2093).

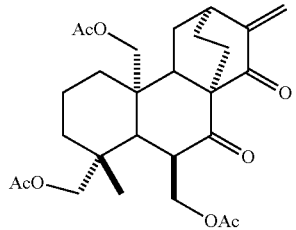

Compound 52: $^1$H NMR (400 MHz, CDCl$_3$) δ: 5.98 (1H, s), 5.33 (1H, s), 4.31 (1H, dd, J=3.2, 11.2 Hz), 4.29 (1H, d, J=13.6 Hz), 4.11 (1H, d, J=8.0 Hz), 4.08 (1H, d, J=13.6 Hz), 4.06 (1H, d, J=8.0 Hz), 3.99 (2H, d, J=3.6 Hz), 3.10 (1H, m), 2.84 (1H, brs), 2.29-2.30 (2H, m), 2.05 (3H, s), 2.04 (3H, s), 2.00 (3H, s), 1.48-1.96 (9H, m), 1.09-1.25 (2H, m), 1.04 (3H, s). $^{13}$C NMR (100 MHz, CDCl$_3$) δ: 206.7, 195.9, 170.9, 170.8, 170.5, 146.6, 119.0, 66.3, 65.8, 63.4, 57.6, 53.9, 49.5, 44.7, 38.5, 38.9, 36.8, 35.7, 33.3, 27.1, 26.7, 26.5, 23.3, 20.8 (3CH3), 17.9. HREIMS m/z 488.2397 [M]$^+$ (C$_{27}$H$_{36}$O$_8$, calcd. 488.2410).

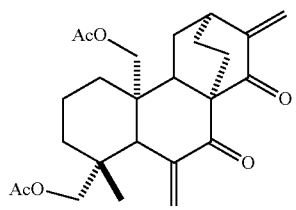

Compound 53: $^1$H NMR (400 MHz, CDCl$_3$) δ: 6.51 (1H, t, J=3.6 Hz), 6.05 (1H, s), 5.82 (1H, t, J=3.6 Hz), 5.34 (1H, s), 4.38 (1H, d, J=11.2 Hz), 4.30 (1H, d, J=12.8 Hz), 4.16 (1H, d, J=11.2 Hz), 4.14 (1H, d, J=12.8 Hz), 2.84 (1H, s), 2.52 (1H, s), 2.22 (1H, m), 2.13 (1H, m), 2.06 (3H, s), 2.01 (3H, s), 1.51-1.96 (8H, m), 1.21 (3H, s), 1.11 (2H, m), 0.87 (1H, m). $^{13}$C NMR (100 MHz, CDCl$_3$) δ: 197.2, 195.8, 171.0, 170.3, 146.1, 142.5, 125.1, 119.6, 63.6, 63.5, 57.4, 57.0, 47.8, 39.6, 38.5, 37.6, 35.7, 33.3, 28.1, 27.2, 24.7, 20.8, 20.7, 17.7. HREIMS m/z 428.2202 [M]$^+$ (C$_{25}$H$_{32}$O$_6$, calcd. 428.2199).

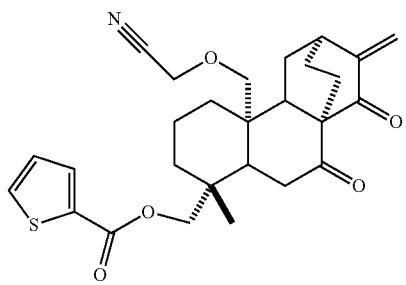

Compound 55: $^1$H NMR (400 MHz, CDCl$_3$) δ: 7.80 (1H, dd, J=1.2, 3.6 Hz), 7.59 (1H, dd, J=1.2, 4.8 Hz), 7.12 (1H, dd, J=3.6, 4.8 Hz), 6.05 (1H, d, J=1.2 Hz), 5.35 (1H, d, J=1.2 Hz), 4.39 (1H, d, J=11.6 Hz), 4.34 (1H, d, J=16.0 Hz), 4.18 (1H, d, J=16.0 Hz), 4.15 (1H, d, J=11.6 Hz), 4.06 (1H, d, J=10.8 Hz), 3.69 (1H, d, J=10.8 Hz), 2.86 (1H, brs), 2.65 (2H, m), 2.27 (1H, m), 2.03-2.11 (2H, m), 1.84-1.92 (4H, m), 1.57-1.73 (5H, m), 1.08-1.19 (1H, m), 1.00-1.08 (1H, m), 1.06 (3H, s). $^{13}$C NMR (100 MHz, CDCl$_3$) δ: 207.8, 196.4, 162.2, 146.1, 133.3, 133.2, 132.6, 127.8, 119.5, 114.7, 71.5, 66.2, 57.9, 56.2, 51.5, 48.1, 39.4, 38.6, 36.9, 36.1, 35.6, 33.7, 26.9, 26.5, 26.0, 24.0, 18.1. HREIMS m/z 481.1932 [M]$^+$ (C$_{27}$H$_{31}$NO$_5$S, calcd. 481.1923).

Compound 59: $^1$H NMR (400 MHz, CDCl$_3$) δ: 6.05 (1H, s), 5.36 (1H, s), 4.39 (1H, d, J=12.8 Hz), 4.32 (1H, d, J=12.8 Hz), 4.20 (1H, d, J=9.6 Hz), 4.06 (1H, d, J=9.6 Hz), 3.68 (4H, brs), 3.50 (1H, brs), 3.46 (1H, brs), 3.30 (2H, brs), 3.01 (3H, s), 2.85 (1H, brs), 2.70 (1H, dd, J=8.8, 20.0 Hz), 2.46 (1H, dd, J=12.0, 20.0 Hz), 2.22 (1H, t, J=12.0 Hz), 2.10 (1H, t, J=10.0 Hz), 1.59-1.99 (10H, m), 1.05-1.17 (2H, m), 1.01 (3H, s). $^{13}$C NMR (100 MHz, CDCl$_3$) δ: 207.6, 195.9, 154.6, 145.8, 119.0, 70.6, 66.4, 64.8, 57.9, 51.1, 48.0, 38.5, 38.3, 36.8, 35.5, 35.4, 33.6, 26.9, 26.3, 25.5, 23.5, 17.8. HREIMS m/z 523.2231 [M]$^+$ (C$_{26}$H$_{37}$NO$_8$S, calcd. 523.2240).

Compound 61: $^1$H NMR (400 MHz, CDCl$_3$) δ: 6.03 (1H, s), 5.34 (1H, s), 4.49 (1H, d, J=11.2 Hz), 4.29 (1H, d, J=11.2 Hz), 4.19 (1H, d, J=10.8 Hz), 4.05 (1H, d, J=10.8 Hz), 3.64 (4H, brs), 3.43 (4H, brs), 3.07 (3H, s), 2.83 (1H, brs), 2.65 (1H, dd, J=8.8, 20.0 Hz), 2.48 (1H, dd, J=12.4, 19.6 Hz), 2.26 (1H, t, J=13.2 Hz), 2.07-2.15 (2H, m), 1.81-1.94 (6H, m), 1.59-1.70 (4H, m), 1.04-1.11 (2H, m), 0.94 (3H, s). $^{13}$C NMR (100 MHz, CDCl$_3$) δ: 207.4, 196.1, 155.1, 145.9, 119.7, 66.8, 66.1, 58.0, 51.4, 48.3, 39.2, 38.2, 37.6, 37.0, 35.8, 35.5, 33.1, 26.8, 26.4, 26.2, 23.6, 17.7. HREIMS m/z 523.2245 [M]$^+$ (C$_{26}$H$_{37}$NO$_8$S, calcd. 523.2240).

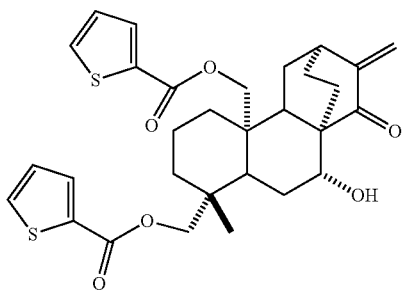

Compound 63: $^1$H NMR (400 MHz, CDCl$_3$) δ: 7.87 (1H, d, J=3.8 Hz), 7.79 (1H, d, J=3.8 Hz), 7.11 (2H, m), 6.00 (1H, s), 5.29 (1H, s), 4.98 (1H, s), 4.98 (1H, d, J=13.0 Hz), 4.50 (2H, m), 4.38 (1H, d, J=11.0 Hz), 4.17 (1H, m), 2.81 (1H, s), 2.44 (1H, brs), 2.09-2.15 (2H, m), 1.48-2.05 (12H, m), 1.15-1.25 (2H, m), 1.15 (3H, s), 0.90 (1H, m). $^{13}$C NMR (100 MHz, CDCl$_3$) δ: 203.7, 162.1, 146.7, 133.8, 133.7, 133.4, 133.3, 132.7, 132.3, 128.0, 127.8, 118.2, 71.4, 67.7, 64.0, 53.1, 50.6, 46.8, 42.2, 36.9, 35.7, 35.3, 28.1, 27.8, 26.1, 25.0, 19.6, 18.2. HREIMS m/z 554.1798 [M]$^+$ (C$_{30}$H$_{34}$O$_6$S$_2$, calcd. 554.1797).

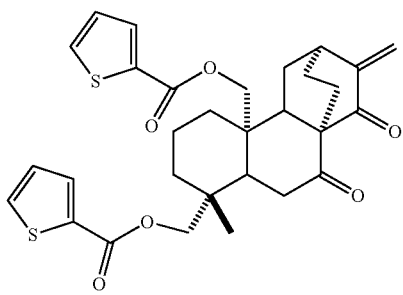

Compound 64: $^1$H NMR (400 MHz, CDCl$_3$) δ: 7.67-7.70 (2H, m), 7.50-7.53 (2H, m), 7.02-7.06 (2H, m), 6.06 (1H, d, J=1.6 Hz), 5.35 (1H, d, J=1.6 Hz), 4.61 (2H, d, J=3.2 Hz), 4.37 (1H, d, J=11.2 Hz), 4.25 (1H, d, J=11.2 Hz), 2.78-2.94 (3H, m), 2.12-2.28 (2H, m), 1.61-2.03 (11H, m), 1.10-1.28 (1H, m), 1.06 (3H, s). $^{13}$C NMR (100 MHz, CDCl3) δ: 207.5, 195.8, 161.6, 161.5, 145.9, 133.7, 133.0 (Cd and Cs), 132.9, 132.1, 132.0, 127.8, 127.4, 119.3, 66.3, 64.2, 57.8, 51.2, 48.1, 38.5, 38.4, 36.8, 36.6, 35.4, 33.7, 26.7, 26.3, 26.0, 23.8, 17.8. HREIMS m/z 552.1655 [M]$^+$ (C$_{30}$H$_{32}$O$_6$S$_2$, calcd. 552.1640).

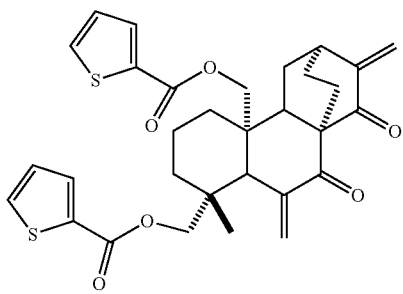

Compound 65: $^1$H NMR (400 MHz, CDCl$_3$) δ: 7.75-7.80 (2H, m), 7.55-7.60 (2H, m), 7.09-7.13 (2H, m), 6.70 (1H, d, J=2.8 Hz), 6.07 (1H, d, J=1.6 Hz), 6.00 (1H, d, J=2.8 Hz), 5.35 (1H, d, J=1.6 Hz), 4.74 (1H, d, J=11.6 Hz), 4.60 (1H, d, J=12.8 Hz), 4.49 (1H, d, J=11.6 Hz), 4.40 (1H, d, J=12.8 Hz), 2.86 (1H, m), 2.60 (1H, t, J=2.8 Hz), 1.56-2.28 (12H, m), 1.30 (3H, s), 1.14-1.25 (1H, m). $^{13}$C NMR (100 MHz, CDCl$_3$) δ: 196.8, 195.8, 162.0, 161.7, 146.2, 141.3, 134.2, 133.5, 133.4, 133.1, 132.6, 132.5, 128.1, 127.8, 126.4, 119.6, 64.2, 63.8, 57.4, 57.1, 47.9, 40.4, 38.8, 38.0, 35.7, 33.4, 27.7, 27.2, 27.0, 25.2, 17.6. HREIMS m/z 564.1643 [M]$^+$ (C$_{31}$H$_{32}$O$_6$S$_2$, calcd. 564.1640).

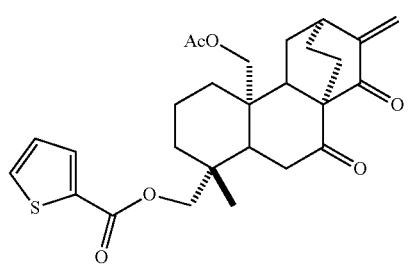

Compound 66: $^1$H NMR (400 MHz, CDCl$_3$) δ: 7.80 (1H, d, J=3.2 Hz), 7.57 (1H, d, J=4.4 Hz), 7.12 (1H, m), 6.06 (1H, s), 5.36 (1H, s), 4.20-4.38 (4H, m), 2.85 (1H, s), 2.66-2.81 (2H, m), 2.29 (1H, m), 2.12 (1H, m), 1.99 (3H, s), 1.57-1.97 (10H, m), 1.06-1.25 (2H, m), 1.04 (3H, s). $^{13}$C NMR (100 MHz, CDCl$_3$) δ: 207.6, 196.3, 170.4, 162.0, 146.1, 133.3 (Cd and Cs), 132.5, 127.8, 119.6, 70.8, 65.9, 63.8, 58.0, 51.7, 48.3, 38.8, 38.3, 37.2, 36.4, 35.6, 33.6, 27.0, 26.3, 25.9, 23.4, 20.8, 17.9. HREIMS m/z 484.1923 [M]$^+$ (C$_{27}$H$_{32}$O$_6$S, calcd. 484.1920).

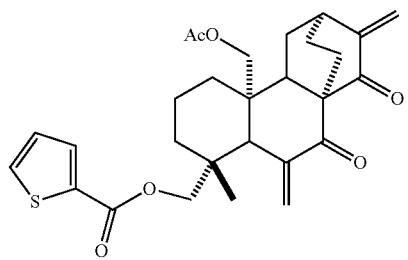

Compound 67: $^1$H NMR (400 MHz, CDCl$_3$) δ: 7.81 (1H, dd, J=1.2, 3.6 Hz), 7.57 (1H, dd, J=1.2, 5.2 Hz), 7.21 (1H, m), 6.54 (1H, d, J=2.4 Hz), 6.06 (1H, d, J=1.2 Hz), 5.90 (1H, d, J=2.4 Hz), 5.34 (1H, d, J=1.2 Hz), 4.59 (1H, dd, J=1.2, 11.6 Hz), 4.90 (1H, d, J=1.2 Hz), 4.32 (1H, d, J=12.8 Hz), 4.21 (1H, d, J=12.8 Hz), 2.85 (1H, d, J=3.2 Hz), 2.58 (1H, m), 2.23-2.31 (1H, m), 2.14-2.19 (1H, m), 2.02 (3H, s), 1.70-2.03 (8H, m), 1.54-1.59 (1H, m), 1.31 (3H, s), 1.10-1.30 (2H, m). $^{13}$C NMR (100 MHz, CDCl$_3$) δ: 197.1, 195.8, 170.3, 162.2, 146.1, 142.6, 133.5 (Cd and Cs), 132.5, 127.8, 125.2, 119.6, 64.2, 63.4, 57.4, 56.9, 47.8, 39.6, 38.5, 38.1, 35.6, 33.4, 28.1, 27.2, 27.1, 24.7, 20.7, 17.8. HREIMS m/z 496.1918 [M]$^+$ (C$_{28}$H$_{32}$O$_6$S, calcd. 496.1920).

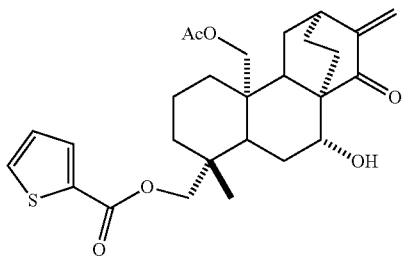

Compound 70: $^1$H NMR (400 MHz, CDCl$_3$) δ: 7.80 (1H, dd, J=1.2, 3.6 Hz), 7.55 (1H, dd, J=1.2, 4.8 Hz), 7.11 (1H, dd, J=3.6, 4.8 Hz), 5.99 (1H, d, J=1.6 Hz), 5.29 (1H, d, J=1.6 Hz), 4.64 (1H, d, J=12.8 Hz), 4.47 (1H, d, J=11.2 Hz), 4.27 (1H, d, J=12.8 Hz), 4.22 (1H, d, J=11.2 Hz), 4.13 (1H, m), 2.80 (1H, brs), 2.45 (1H, d, J=3.2 Hz), 2.15 (3H, s), 2.06-2.10 (1H, m), 1.62-1.98 (11H, m), 1.44-1.52 (2H, m), 1.17-1.22 (1H, m), 1.13 (3H, s), 0.82-0.90 (1H, m). $^{13}$C NMR (100 MHz, CDCl$_3$) δ: 203.8, 170.8, 162.1, 146.6, 133.7, 133.3, 132.4, 127.8, 118.2, 71.3, 67.5, 63.3, 53.0, 50.5, 46.9, 41.5, 36.8, 36.6, 35.6, 35.4, 28.0, 27.6, 25.9, 25.0, 21.1, 19.5, 18.0. HREIMS m/z 486.2076 [M]$^+$ (C$_{27}$H$_{34}$O$_6$S, calcd. 486.2076).

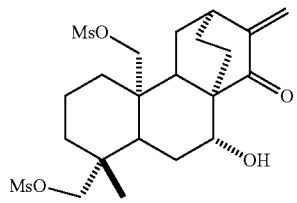

Compound 72a: $^1$H NMR (400 MHz, CDCl$_3$) δ: 5.98 (1H, d, J=1.2 Hz), 5.30 (1H, d, J=1.2 Hz), 4.56 (1H, d, J=11.2 Hz), 4.24 (1H, d, J=11.2 Hz), 4.22 (1H, d, J=13.2 Hz), 4.20 (1H, d, J=13.2 Hz), 4.07 (1H, d, J=12.0 Hz), 3.13 (3H, s), 3.04 (3H, s), 2.8 (1H, s), 2.60 (1H, s), 2.08 (1H, d, J=13.6 Hz), 2.00 (1H, dd, J=4.8, 13.6 Hz), 1.65-1.84 (6H, m), 1.58-1.65 (1H, m), 1.38-1.49 (3H, m), 1.12-1.23 (1H, m), 1.09 (3H, s), 0.84-0.92 (1H, m). $^{13}$C NMR (100 MHz, CDCl$_3$) δ: 202.9, 146.2, 118.6, 72.3, 70.6, 67.8, 52.3, 50.1, 46.7, 41.5, 37.4, 36.6, 36.9, 35.7, 35.3, 34.7, 27.9, 27.0, 25.6, 24.8, 19.2, 17.9. HREIMS m/z 490.1703 [M]$^+$ (C$_{22}$H$_{34}$O$_8$S$_2$, calcd. 490.1695).

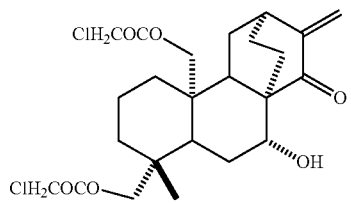

Compound 72b: $^1$H NMR (400 MHz, CDCl$_3$) δ: 5.99 (1H, d, J=1.6 Hz), 5.30 (1H, d, J=1.6 Hz), 4.71 (1H, d, J=13.0 Hz), 4.35-4.72 (2H, m), 4.06-4.17 (6H, m), 2.80 (1H, s), 2.49 (1H, brs), 1.98-2.03 (2H, m), 1.45-1.82 (11H, m), 1.08-1.20 (2H, m), 1.08-1.20 (2H, m), 1.06 (3H, s), 0.84-0.90 (1H, m). $^{13}$C NMR (100 MHz, CDCl$_3$) δ: 203.4, 167.3, 167.2, 146.4, 118.4, 71.0, 68.4, 65.2, 52.9, 50.4, 46.7, 41.7, 40.8, 36.6, 36.1, 35.5, 34.9, 28.0, 27.4, 25.5, 24.9, 19.4, 18.1. HREIMS m/z 486.1578 [M]$^+$ (C$_{24}$H$_{32}$O$_6$Cl$_2$, calcd. 486.1576).

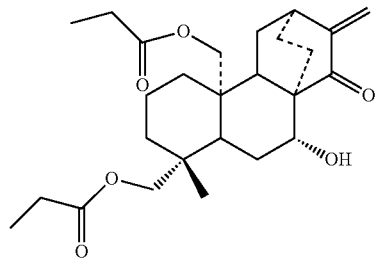

Compound 72c: $^1$H NMR (400 MHz, CDCl$_3$) δ: 5.98 (1H, d, J=1.6 Hz), 5.28 (1H, d, J=1.6 Hz), 4.64 (1H, d, J=12.8 Hz), 4.21-4.25 (2H, m), 4.02 (1H, d, J=11.2 Hz), 3.74 (1H, m), 2.79 (1H, brs), 2.32-2.45 (4H, m), 1.41-2.04 (13H, m), 1.20-1.27 (1H, m), 1.13-1.18 (7H, m), 1.08-1.10 (1H, m), 1.02 (3H, s), 0.78-0.88 (1H, m). $^{13}$C NMR (100 MHz, CDCl$_3$) δ: 203.8, 174.4, 174.2, 146.7, 118.1, 71.3, 66.7, 63.2, 53.1, 50.5, 46.8, 41.7, 36.6, 36.5, 35.6, 35.3, 28.0, 27.7, 27.67, 27.62, 25.7, 25.0, 19.5, 18.1, 9.1, 8.9. HREIMS m/z 446.2673 [M]$^+$ (C$_{26}$H$_{38}$O$_6$, calcd. 446.2668).

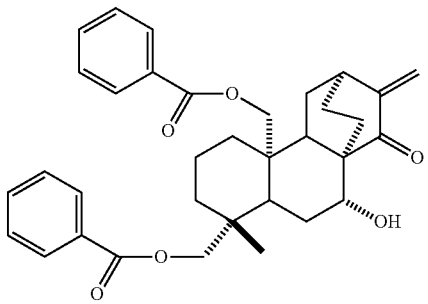

Compound 72d: $^1$H NMR (400 MHz, CDCl$_3$) δ: 8.02-8.13 (4H, m), 7.52-7.63 (2H, m), 7.41-7.49 (4H, m), 6.01 (1H, d, J=1.6 Hz), 5.30 (1H, d, J=1.6 Hz), 5.04 (1H, d, J=12.8 Hz), 4.63 (1H, d, J=11.2 Hz), 4.50 (1H, d, J=12.8 Hz), 4.38 (1H, d, J=11.2 Hz), 4.18-4.22 (1H, m), 2.81 (1H, brs), 2.14-2.19 (2H, m), 1.63-2.03 (8H, m), 1.49-1.54 (2H, m), 1.14-1.28 (2H, m), 1.19 (3H, s), 0.85-0.96 (1H, m). $^{13}$C NMR (100 MHz, CDCl$_3$) δ: 203.7, 171.1, 166.6, 166.5, 146.6, 133.6, 133.1, 132.8, 130.2, 130.1, 129.8, 129.6, 129.5, 129.3, 128.5, 128.42, 128.40, 118.4, 71.3, 67.2, 63.9, 53.2, 50.5, 46.7, 42.3, 37.0, 36.7, 35.6, 35.2, 28.1, 27.7, 25.9, 25.0, 19.6, 18.2. HREIMS m/z 542.2670 [M]$^+$ (C$_{34}$H$_{38}$O$_6$, calcd. 542.2668).

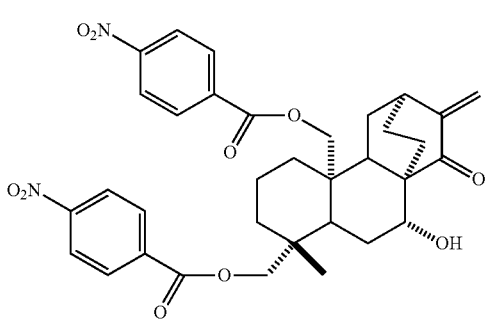

Compound 72e: $^1$H NMR (400 MHz, CDCl$_3$) δ: 8.18-8.34 (8H, m), 6.03 (1H, d, J=1.2 Hz), 5.32 (1H, d, J=1.2 Hz), 5.05 (1H, d, J=12.8 Hz), 4.73 (1H, d, J=11.2 Hz), 4.54 (1H, d, J=12.8 Hz), 4.34 (1H, d, J=11.2 Hz), 4.21 (1H, d, J=3.2 Hz), 2.85 (1H, brs), 2.50 (1H, s), 2.14-2.18 (2H, m), 1.53-1.94 (11H, m), 1.18-1.33 (2H, m), 1.22 (3H, s), 0.94-1.02 (1H, m). $^{13}$C NMR (100 MHz, CDCl$_3$) δ: 203.3, 164.8, 164.6, 150.6, 150.5, 146.3, 135.3, 135.0, 130.8, 130.6, 123.7, 123.6, 118.7, 71.0, 67.9, 64.9, 53.1, 46.8, 36.4, 35.5, 35.1, 28.2, 27.6, 25.8, 25.1, 19.6, 18.2. HREIMS m/z 632.2377 [M]$^+$ (C$_{34}$H$_{36}$N$_2$O$_{10}$, calcd. 632.2370).

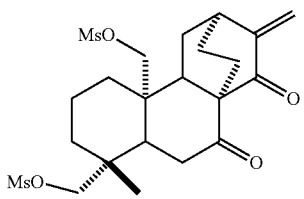

Compound 73a: $^1$H NMR (400 MHz, CDCl$_3$) δ: 6.05 (1H, s), 5.39 (1H, s), 4.80 (1H, d, J=11.2 Hz), 4.33 (1H, d, J=11.2 Hz), 4.30 (1H, d, J=10.0 Hz), 4.15 (1H, d, J=10.0 Hz), 3.06 (3H, s), 3.04 (3H, s), 2.89 (1H, brs), 2.66 (1H, dd, J=9.6, 9.6 Hz), 2.51 (1H, dd, J=11.6, 11.6 Hz), 2.31 (1H, t, J=12.4, 14.0 Hz), 2.17 (1H, t, J=8.8, 10.4 Hz), 1.86-2.06 (5H, m), 1.76-1.80 (1H, d, J=13.6 Hz), 1.60-1.71 (4H, m), 1.08-1.20 (2H, m), 1.03 (3H, s). $^{13}$C-NMR (100 MHz, CDCl$_3$) δ: 207.3, 195.9, 145.8, 119.9, 71.6, 65.8, 57.9, 51.1, 47.9, 38.8, 38.5, 37.9, 37.1, 36.6, 35.3, 35.2, 32.8, 26.7, 26.1, 25.5, 23.3, 17.5. HREIMS m/z 488.1512 [M]$^+$ (C22H32O8S2, calcd. 488.1539).

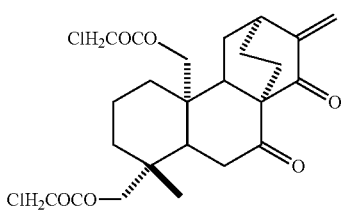

Compound 73b: $^1$H NMR (400 MHz, CDCl$_3$) δ: 6.06 (1H, d, J=1.2 Hz), 5.36 (1H, d, J=1.2 Hz), 4.52 (1H, d, J=12.8 Hz), 4.20-4.26 (3H, m), 3.97-4.10 (5H, m), 2.86 (1H, s), 2.57-2.70 (2H, m), 2.10-2.31 (2H, m), 1.61-1.98 (8H, m), 1.08-1.25 (3H, m), 1.07 (3H, s). $^{13}$C NMR (100 MHz, CDCl$_3$) δ: 207.6, 196.1, 167.3, 167.0, 145.9, 119.9, 66.9, 65.4, 58.0, 51.6, 48.3, 40.7, 40.5, 38.6, 38.5, 37.0, 36.0, 35.5, 33.3, 26.9, 26.3, 25.9, 23.6, 17.9. HREIMS m/z 484.1423 [M]$^+$ (C$_{24}$H$_{30}$Cl$_2$O$_6$, calcd. 484.1419).

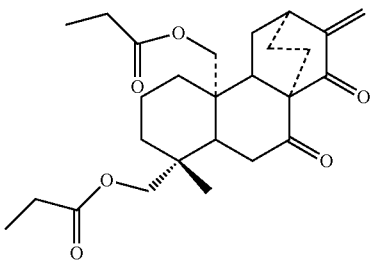

Compound 73c: $^1$H NMR (400 MHz, CDCl$_3$) δ: 6.04 (1H, d, J=1.6 Hz), 5.34 (1H, d, J=1.6 Hz), 4.36 (1H, d, J=13.2 Hz), 4.16 (1H, d, J=13.2 Hz), 4.05 (1H, d, J=11.2 Hz), 4.00 (1H, d, J=11.2 Hz), 2.84 (1H, brs), 2.66 (1H, s), 2.63 (1H, s), 2.23-2.35 (5H, m), 2.10 (1H, m), 1.57-1.93 (10H, m), 1.12-1.15 (6H, m), 1.03-1.10 (2H, m), 0.92 (3H, s). $^{13}$C NMR (100 MHz, CDCl$_3$) δ: 207.5, 196.1, 174.0, 173.8, 146.0, 119.3, 64.7, 63.5, 57.8, 51.6, 48.1, 38.6, 38.1, 36.7, 35.9, 35.4, 33.4, 27.33, 27.31, 26.9, 26.1, 25.7, 23.3, 17.8, 8.90, 8.57. HREIMS m/z 444.2523 [M]$^+$ (C$_{26}$H$_{36}$O$_6$, calcd. 444.2512).

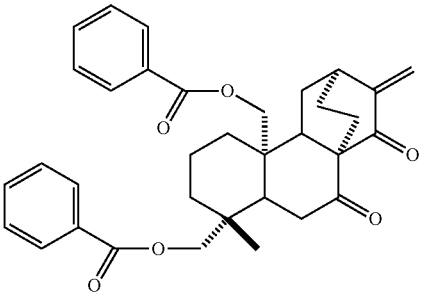

Compound 73d: $^1$H NMR (400 MHz, CDCl$_3$) δ: 7.87-7.90 (4H, m), 7.48-7.52 (2H, m), 7.36-7.38 (4H, m), 6.06 (1H, s), 5.35 (1H, s), 4.69 (1H, d, J=13.2 Hz), 4.62 (1H, d, J=13.2 Hz), 4.41 (1H, d, J=11.2 Hz), 4.23 (1H, d, J=11.2 Hz), 2.82-2.94 (2H, m), 2.16-2.25 (2H, m), 1.74-2.06 (9H, m), 1.61-1.64 (2H, m), 1.13-1.27 (2H, m), 1.09 (3H, s). $^{13}$C NMR (100 MHz, CDCl$_3$) δ: 207.9, 196.0, 166.5, 166.0, 146.0, 133.2, 132.7, 129.7, 129.4, 129.3, 128.8, 128.4, 128.2, 119.5, 66.4, 64.4, 58.1, 51.4, 48.3, 38.8, 38.6, 37.0, 36.8, 35.5, 33.9, 26.9, 26.5, 26.2, 24.0, 18.0. HREIMS m/z 540.2524 [M]$^+$ (C$_{34}$H$_{36}$O$_6$, calcd. 540.2512).

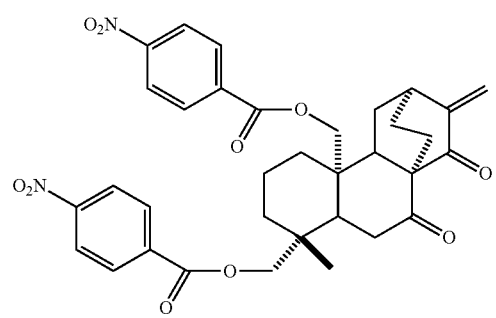

Compound 73e: $^1$H NMR (400 MHz, CDCl$_3$) δ: 8.20-8.23 (4H, m), 8.01-8.06 (4H, m), 6.09 (1H, s), 5.39 (1H, s), 4.72 (1H, d, J=13.2 Hz), 4.61 (1H, d, J=13.2 Hz), 4.35 (1H, d, J=11.2 Hz), 4.21 (1H, d, J=11.2 Hz), 2.75-2.90 (3H, m), 2.21-2.33 (2H, m), 1.66-2.10 (9H, m), 1.53-1.56 (1H, m), 1.15-1.30 (2H, m), 1.10 (3H, s). $^{13}$C NMR (100 MHz, CDCl$_3$) δ: 208.1, 195.8, 165.0, 164.3, 150.6, 150.5, 145.8, 134.9, 134.1, 130.7, 130.4, 123.7, 123.5, 120.1, 67.4, 65.5, 58.2, 51.4, 48.3, 39.0, 38.7, 37.0, 36.8, 35.5, 33.9, 27.0, 26.5, 26.1, 25.5, 23.9, 18.0. HREIMS m/z 630.2222 [M]$^+$ (C$_{34}$H$_{34}$N$_2$O$_{10}$, calcd. 630.2213).

Compound 74c: $^1$H NMR (500 MHz, CDCl$_3$) δ: 6.52 (1H, d, J=3.0 Hz), 6.05 (1H, s), 5.84 (1H, d, J=3.0 Hz), 5.34 (1H, s), 4.42 (1H, d, J=11.5 Hz), 4.32 (1H, d, J=12.9 Hz), 4.14 (1H, d, J=11.5 Hz), 4.13 (1H, d, J=12.9 Hz), 2.83 (1H, brs), 2.51 (1H, m), 2.34 (1H, q, J=7.45, 15.1 Hz), 2.27 (1H, q, J=7.45, 15.1 Hz), 2.26 (1H, q, J=7.45, 15.1 Hz), 2.23 (1H, m), 2.14 (1H, m). $^{13}$C NMR (125 MHz, CDCl$_3$) δ: 197.1, 195.9, 174.4, 173.9, 146.1, 142.5, 125.2, 119.6, 63.4, 63.3, 57.4, 57.0, 39.7, 38.5, 37.8, 35.7, 33.4, 28.1, 27.5, 27.4, 27.2, 27.1. HREIMS m/z 456.2502 [M]$^+$ (C$_{27}$H$_{36}$O$_6$, calcd. 456.2512).

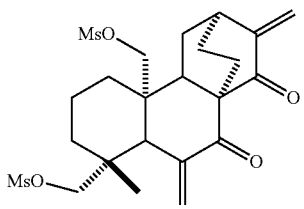

Compound 74a: $^1$H NMR (400 MHz, CDCl$_3$) δ: 6.48 (1H, d, J=2.8 Hz), 6.06 (1H, d, J=1.2 Hz), 5.79 (1H, d, J=2.8 Hz), 5.38 (1H, d, J=2.8 Hz), 4.43 (1H, d, J=10.4 Hz), 4.41 (1H, d, J=10.8 Hz), 4.33 (1H, d, J=10.4 Hz), 4.27 (1H, d, J=10.8 Hz), 3.05 (3H, s), 2.98 (3H, s), 2.88 (1H, s), 2.66 (1H, t, J=2.8 Hz), 2.33 (1H, m), 2.12-2.20 (1H, m), 2.02-2.08 (2H, m), 1.89-1.94 (3H, m), 1.63-1.74 (5H, m), 1.35 (3H, s), 1.13-1.25 (1H, m). $^{13}$C NMR (100 MHz, CDCl$_3$) δ: 197.2, 195.5, 145.8, 142.5, 125.2, 120.1, 70.0, 65.9, 56.9, 47.4, 39.8, 38.0, 37.8, 37.5, 37.0, 35.5, 32.8, 28.3, 26.9, 24.5, 17.7. HREIMS m/z 500.1541 [M]$^+$ (C$_{23}$H$_{32}$O$_8$S$_2$, calcd. 500.1539).

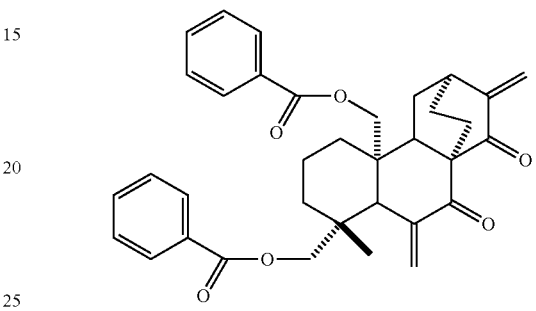

Compound 74d: $^1$H NMR (500 MHz, CDCl$_3$) δ: 8.02 (2H, d, J=10.0 Hz), 7.95 (2H, d, J=10.0 Hz), 7.57 (2H, m), 7.45 (4H, m), 6.71 (1H, d, J=3.0 Hz), 6.07 (1H, s), 6.01 (1H, d, J=3.0 Hz), 5.35 (1H, s), 4.74 (1H, d, J=11.4 Hz), 4.61 (1H, d, J=13.0 Hz), 4.56 (1H, d, J=11.4 Hz), 4.52 (1H, d, J=13.0 Hz), 2.85 (1H, s), 2.63 (1H, m), 1.33 (3H, s). $^{13}$C NMR (125 MHz, CDCl$_3$) δ: 196.8, 195.8, 166.4, 166.3, 146.1, 141.5, 133.3, 132.9, 129.9, 129.6, 129.5, 129.1, 128.5, 128.3, 126.2, 119.6, 64.2, 63.6, 57.6, 57.2, 48.0, 40.5, 38.8, 38.0, 35.6, 33.6, 27.7, 27.3, 27.1, 25.2, 17.6. HREIMS m/z 552.2499 [M]$^+$ (C$_{35}$H$_{36}$O$_6$, calcd. 552.2512).

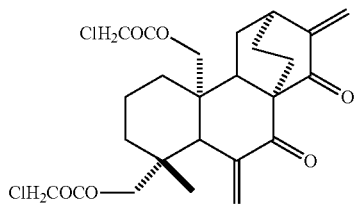

Compound 74b: $^1$H NMR (400 MHz, CDCl$_3$) δ: 6.53 (1H, d, J=2.4 Hz), 6.06 (1H, s), 5.82 (1H, d, J=2.4 Hz), 5.36 (1H, s), 4.48 (1H, m), 4.33 (1H, d, J=11.2 Hz), 4.21 (1H, d, J=13.2 Hz), 4.10 (2H, s), 4.04 (2H, s), 2.86 (1H, s), 2.57 (1H, s), 2.12-2.30 (2H, m), 1.55-1.93 (10H, m), 1.25 (3H, s), 1.12-1.22 (2H, m). $^{13}$C NMR (100 MHz, CDCl$_3$) δ: 197.2, 195.6, 167.4, 166.8, 145.9, 142.1, 125.8, 119.8, 65.4, 65.1, 57.3, 57.0, 47.7, 40.7, 40.5, 39.9, 38.2, 37.7, 35.6, 32.9, 28.0, 27.1, 27.0, 24.8, 17.7. HREIMS m/z 496.1422 [M]$^+$ (C$_{25}$H$_{30}$Cl$_2$O$_6$, calcd. 496.1419).

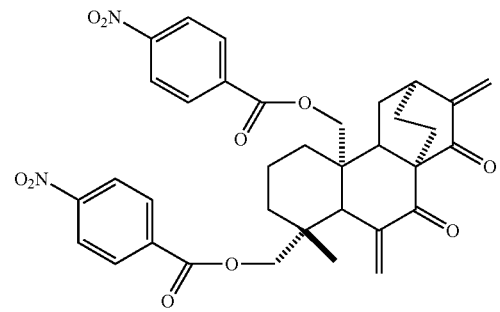

Compound 74e: $^1$H NMR (400 MHz, CDCl$_3$) δ: 8.27-8.30 (4H, m), 8.10-8.15 (4H, m), 6.67 (1H, d, J=1.2 Hz), 6.09 (1H, s), 5.95 (1H, d, J=1.2 Hz), 5.39 (1H, s), 4.61-4.63 (3H, m), 4.51 (1H, d, J=11.6 Hz), 2.89 (1H, brs), 2.72 (1H, s), 2.26-2.30 (2H, m), 1.60-2.04 (8H, m), 1.39 (3H, s), 1.25-1.30 (4H, m), 0.88 (1H, m). $^{13}$C NMR (100 MHz, CDCl$_3$) δ: 196.9, 195.4, 164.8, 164.5, 150.7, 150.5, 145.8, 142.3, 135.1, 134.2, 130.9, 130.6, 125.8, 123.7, 123.6, 120.1, 65.1, 65.0, 57.3, 57.0, 47.7, 40.0, 38.6, 38.1, 35.5, 33.6, 29.6, 28.3, 27.2, 27.1, 24.9, 17.7. HREIMS m/z 642.2219 [M]$^+$ (C$_{35}$H$_{34}$N$_2$O$_{10}$, calcd. 642.2213).

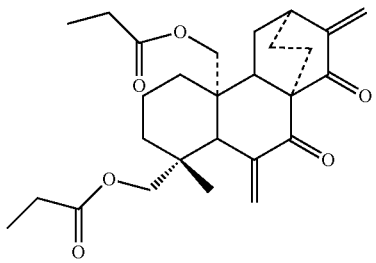

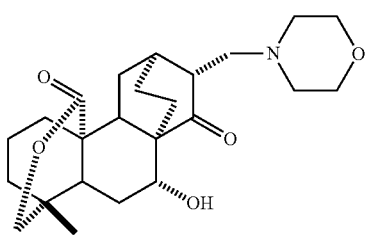

Compound 75: $^1$H NMR (400 MHz, CDCl$_3$) δ: 4.26 (1H, dd, J=2.0, 11.6 Hz), 4.09 (1H, d, J=11.6 Hz), 4.03 (1H, dd, J=4.4, 11.6 Hz), 3.69 (4H, m), 3.17-3.21 (1H, m), 2.87 (1H, m), 2.67 (1H, dd, J=4.4, 12.4 Hz), 2.49-2.52 (3H, m), 2.43-2.46 (1H, d, J=12.4 Hz), 2.31-2.38 (4H, m), 2.21-2.24 (1H, d, J=13.2 Hz), 1.98-2.05 (1H, m), 1.15-1.80 (12H, m), 0.95 (3H, s). $^{13}$C NMR (100 MHz, CDCl$_3$) δ: 220.7, 174.0, 76.3, 69.8, 66.8, 56.9, 53.5, 50.8, 49.8, 46.9, 45.9, 43.3, 40.5, 37.3, 32.7, 29.4, 27.3, 27.2, 23.5, 20.2, 18.4, 17.3. HREIMS m/z 417.2514 [M]$^+$ (C$_{24}$H$_{35}$NO$_5$, calcd. 417.2515).

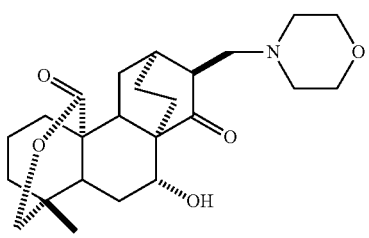

Compound 76: $^1$H NMR (400 MHz, CDCl$^3$) δ: 4.25 (1H, d, J=11.6 Hz), 4.03-4.10 (2H, m), 3.69-3.74 (4H, m), 3.00-3.03 (1H, m), 2.59-3.61 (4H, m), 2.36-2.43 (4H, m), 2.17-2.27 (3H, m), 1.98-2.01 (1H, m), 1.13-1.82 (12H, m), 0.94 (3H, s). $^{13}$C NMR (100 MHz, CDCl$_3$) δ: 220.1, 174.0, 76.4, 69.6, 66.9, 56.9, 53.5, 51.0, 49.7, 47.1, 45.9, 44.2, 40.6, 37.6, 32.8, 29.2, 27.3, 24.0, 23.5, 21.2, 20.2, 16.4. HREIMS m/z 417.2532 [M]$^+$ (C24H35NO5, calcd. 417.2515).

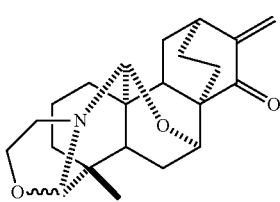

Compound 77: $^1$H NMR (400 MHz, CDCl$_3$) δ: 5.93 (1H, d, J=1.6 Hz), 5.91 (1H, d, J=1.6 Hz), 5.23 (1H, d, J=1.6 Hz), 5.22 (1H, d, J=1.6 Hz), 4.90 (1H, d, J=1.6 Hz), 4.67 (1H, d, J=1.6 Hz), 4.20 (1H, s), 3.83-3.96 (5H, m), 3.68-3.74 (2H, m), 3.46-3.51 (2H, m), 3.19-3.27 (2H, m), 3.04-3.07 (2H, m), 2.78-2.82 (1H, m), 1.09 (3H, s), 0.91 (3H, s). $^{13}$C NMR (100 MHz, CDCl$_3$) δ: 200.8, 148.2, 117.3, 95.1, 91.1, 85.7, 83.4, 67.8, 67.3, 64.9, 63.1, 51.0, 49.2, 49.0, 47.4, 45.5, 44.3, 43.1, 43.0, 40.6, 36.8, 36.7, 35.7, 35.3, 35.1, 33.7, 29.9, 29.8, 29.6, 27.4, 24.5, 24.0, 23.5, 23.3, 22.8, 22.7, 20.6, 20.3. HREIMS m/z 355.2137 [M]$^+$ (C$_{22}$H$_{29}$NO$_3$, calcd. 355.2147).

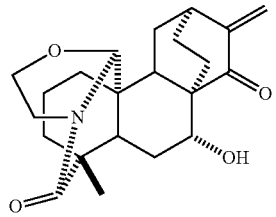

Compound 78: $^1$H NMR (400 MHz, CDCl$_3$) δ: 6.03 (1H, d, J=1.6 Hz), 5.34 (1H, d, J=1.6 Hz), 5.09 (1H, s), 4.15-4.21 (2H, m), 3.86-3.98 (2H, m), 3.24-3.32 (1H, m), 2.81 (1H, brs), 2.49 (1H, d, J=3.6 Hz), 2.33-2.37 (1H, m), 2.19-2.25 (1H, m), 2.07-2.14 (1H, m), 1.99-2.02 (1H, m), 1.80-1.87 (3H, m), 1.63-1.77 (3H, m), 1.25-1.54 (5H, m), 1.23 (3H, s), 0.82-0.89 (1H, m). $^{13}$C NMR (100 MHz, CDCl$_3$) δ: 202.9, 173.1, 146.2, 119.1, 88.9, 70.1, 64.8, 50.1, 49.6, 42.6, 42.2, 41.4, 40.8, 40.2, 35.7, 33.8, 28.4, 26.4, 25.2, 22.3, 20.7, 18.9. HREIMS m/z 371.2107 [M]$^+$ (C22H29NO4, calcd. 371.2097).

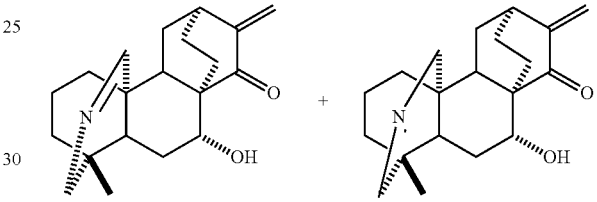

Compound 80: $^1$H NMR (400 MHz, CDCl3) δ: 8.00 (1H, s), 6.01 (1H, d, J=1.6 Hz), 5.32 (1H, d, J=1.6 Hz), 4.37 (1H, d, J=13.6 Hz), 0.91 (3H, s). $^{13}$C NMR (100 MHz, CDCl$_3$) δ: 203.9, 161.9, 146.2, 118.9, 70.4, 52.3, 50.1, 48.7, 42.7, 40.2, 40.0, 39.3, 35.7, 32.7, 27.4, 25.6, 25.0, 24.6, 20.6, 18.4. ESIMS: m/z 314.2 (M+H)$^+$.

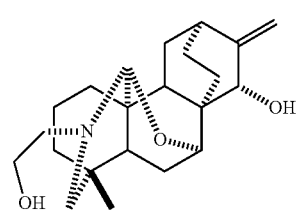

Compound 81: $^1$H NMR (400 MHz, CDCl$_3$) δ: 5.05 (1H, s), 5.03 (1H, s), 4.59 (1H, s), 3.91 (1H, s), 3.82 (1H, m), 3.72-3.76 (1H, m), 3.37-3.41 (1H, m), 2.96-3.00 (1H, m), 2.79-2.82 (2H, m), 2.45 (1H, m), 2.23-2.29 (1H, m), 2.17 (2H, m), 1.10-1.89 (15H, m), 0.82-0.87 (1H, m), 0.78 (3H, s). ESIMS: m/z 360.2 (M+H)$^+$.

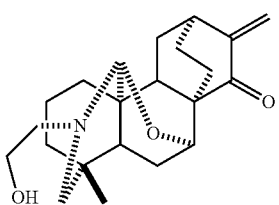

Compound 82: ¹H NMR (400 MHz, CDCl₃) δ: 5.93 (1H, d, J=1.6 Hz), 5.23 (1H, d, J=1.6 Hz), 4.63 (1H, s), 4.00 (1H, d, J=4.8 Hz), 3.73 (1H, m), 3.41 (1H, m), 2.99 (1H, m), 2.84 (2H, m) 2.20-2.36 (2H, m), (1H, d, J=11.2 Hz), 1.79-1.97 (5H, m), 1.42-1.67 (7H, m), 1.15-1.26 (7H, m), 0.71 (3H, s). ¹³C NMR (100 MHz, CDCl₃) δ: 200.7, 148.1, 117.2, 87.3, 68.2, 57.8, 57.4, 51.5, 48.9, 44.5, 44.1, 41.0, 36.8, 35.5, 33.4, 30.0, 27.4, 25.0, 24.6, 24.4, 23.5, 21.1. ESI MS: m/z 358.2 (M+H)⁺.

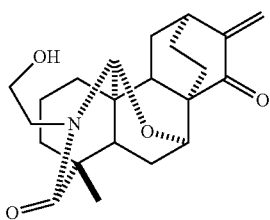

Compound 83: ¹H NMR (400 MHz, CDCl₃) δ: 5.95 (1H, d, J=1.6 Hz), 5.28 (1H, d, J=1.6 Hz), 4.93 (1H, d, J=2.4 Hz), 4.99 (1H, d, J=3.6 Hz), 3.95-3.97 (1H, m), 3.81-3.87 (1H, m), 3.76-3.79 (1H, m), 3.65-3.72 (1H, m), 3.21-3.28 (1H, m), 2.85 (1H, brs), 2.27-2.36 (1H, m), 2.11-2.17 (1H, m), 1.97-2.03 (1H, m), 1.83-1.92 (2H, m), 1.74-1.79 (2H, m), 1.40-1.67 (7H, m), 1.28-1.40 (2H, m), 1.16 (3H, s). ¹³C NMR (100 MHz, CDCl₃) δ: 199.9, 175.5, 147.5, 117.9, 86.6, 67.6, 61.8, 51.8, 48.5, 46.5, 44.4 (Cs, Cd), 39.4, 36.5, 33.9, 29.5, 27.1, 26.4, 24.7, 23.3, 21.0, 19.7. HREIMS m/z 371.2094 [M]⁺ (C₂₂H₂₉NO₄, calcd. 371.2097).

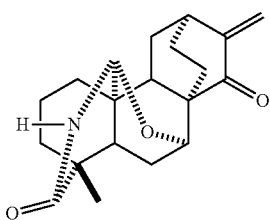

Compound 84: 1H NMR (400 MHz, CDCl3) δ: 6.47 (1H, brs), 5.95 (1H, d, J=1.6 Hz), 5.26 (1H, d, J=1.6 Hz), 4.88 (1H, m), 3.94 (1H, m), 2.83 (1H, m), 2.27-2.36 (1H, m), 2.11-2.17 (1H, m), 1.97-2.04 (1H, m), 1.24-1.91 (13H, m), 1.14 (3H, s). ¹³C NMR (100 MHz, CDCl₃) δ: 200.3, 177.1, 147.8, 117.8, 80.5, 67.2, 48.7, 46.9, 44.6, 44.2, 38.6, 36.6, 33.7, 29.4, 27.3, 26.5, 24.8, 23.4, 20.7, 20.0. HREIMS m/z 327.1841 [M]+(C₂₀H₂₅NO₃, calcd. 327.1834).

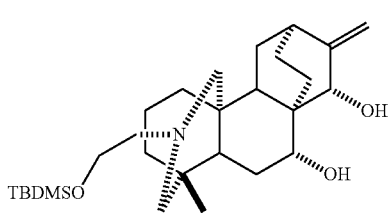

Compound 85: ¹H NMR (400 MHz, CDCl₃) δ: 5.04 (1H, s), 5.00 (1H, s), 3.91 (1H, s), 3.70 (2H, t, J=6.4 Hz), 3.52 (1H, s), 2.75 (1H, d, J=11.2 Hz), 2.59 (1H, d, J=11.2 Hz), 2.04-2.45 (5H, m), 0.90 (9H, s), 0.78 (3H, s), 0.06 (6H, s). ESIMS: 476.4 (M+H)⁺.

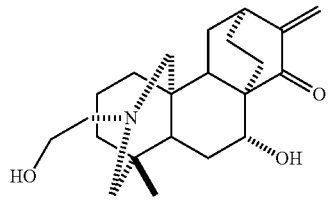

Compound 88: ¹H NMR (400 MHz, CDCl₃) δ: 6.00 (1H, d, J=1.6 Hz), 5.30 (1H, d, J=1.6 Hz), 4.14 (1H, dd, J=4.4, 12.4 Hz), 3.65 (2H, t, J=4.8 Hz), 2.80 (1H, s), 2.64 (1H, d, J=11.2 Hz), 2.37-256 (4H, m), 2.22 (1H, d, J=11.2 Hz), 2.13 (2H, m), 1.90-1.95 (2H, m), 1.54-1.80 (9H, m), 1.39-1.44 (2H, m), 1.25 (1H, s), 1.14-1.17 (1H, s), 1.03 (1H, m), 0.84 (3H, s). ¹³C NMR (100 MHz, CDCl₃) δ: 203.8, 146.4, 118.5, 70.6, 60.7, 59.9, 57.8, 53.5, 50.2, 47.8, 43.0, 40.8, 39.5, 39.2, 35.8, 33.5, 27.5, 26.3, 25.3, 24.6, 23.0, 18.8. HREIMS m/z 359.2452 [M]⁺ (C₂₂H₃₃NO₃, calcd. 359.2460).

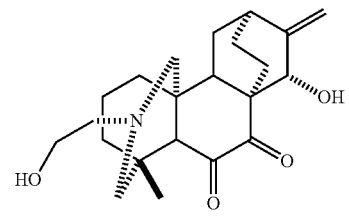

Compound 89: ¹H NMR (400 MHz, CDCl3) δ: 5.90 (1H, s), 5.45 (1H, s), 5.08 (2H, s), 3.92 (1H, s), 3.61 (2H, t, J=5.6 Hz), 2.86 (1H, d, J=11.6 Hz), 2.67 (1H, s), 2.32-2.53 (7H, m), 2.11-2.14 (2H, dd, J=2.8, J=11.2 Hz), 1.90-1.98 (2H, m), 1.50-1.73 (7H, m), 1.33-1.43 (2H, m), 1.24-1.26 (1H, m), 0.96 (3H, s). ¹³C NMR (100 MHz, CDCl₃) δ: 209.4, 150.2, 145.1, 126.4, 113.0, 74.6, 60.9, 60.3, 57.8, 56.5, 53.7, 48.8, 45.6, 41.6, 37.4, 35.8, 35.7, 35.5, 27.3, 26.5, 25.7, 22.4, 20.5. HREIMS m/z 371.2460 [M]⁺ (C₂₃H₃₃NO₃, calcd. 371.2460).

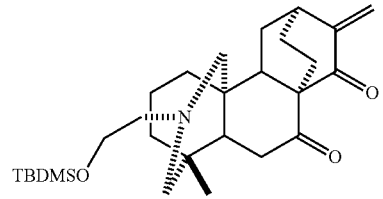

Compound 90: ¹H NMR (400 MHz, CDCl₃) δ: 6.02 (1H, d, J=1.6 Hz), 5.35 (1H, d, J=1.6 Hz), 3.78 (1H, m), 3.64 (2H, t, J=6.0 Hz), 3.49 (1H, m), 0.87 (9H, s), 0.72 (3H, s), 0.02 (6H, s). ESIMS: m/z 472.4 (M+H)⁺.

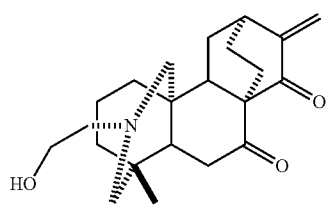

Compound 91: $^1$H NMR (400 MHz, CDCl$_3$) δ: 6.03 (1H, d, J=2.0 Hz), 5.32 (1H, d, J=2.0 Hz), 3.63 (2H, m), 2.82 (2H, m), 2.38-2.53 (5H, m), 2.30 (1H, dd, J=2.4, 10.8 Hz), 2.11-2.18 (2H, m), 1.89-2.03 (3H, m), 1.51-1.82 (7H, m), 1.37-1.46 (1H, m), 1.15-1.25 (2H, m), 0.82-0.90 (1H, m), 0.73 (3H, s). $^{13}$C NMR (100 MHz, CDCl$_3$) δ: 209.6, 196.1, 146.3, 119.8, 60.7, 59.1, 58.3, 57.6, 53.6, 46.6, 46.0, 40.9, 38.4, 37.6, 37.4, 36.0, 34.1, 27.3, 26.4, 25.4, 25.3, 23.0. HREIMS m/z 357.2301 [M]$^+$ (C$_{22}$H$_{31}$NO$_3$, calcd. 357.2304).

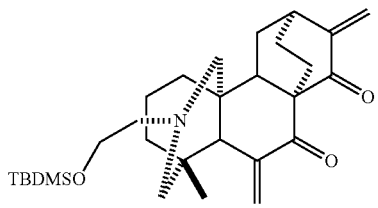

Compound 92: $^1$H NMR (400 MHz, CDCl$_3$) δ: 5.98 (1H, d, J=1.6 Hz), 5.93 (1H, t, J=2.0 Hz), 5.31 (1H, t, J=2.0 Hz), 5.30 (1H, d, J=1.6 Hz), 3.67 (2H, t, J=6.0 Hz), 2.96 (1H, d, J=11.2 Hz), 2.81-2.87 (2H, m), 2.40 (1H, d, J=11.2 Hz), 2.29 (1H, m), 2.27 (2H, t, J=6.0 Hz), 1.22-2.10 (12H, m), 0.92 (2H, m), 0.90 (12H4Me, s), 0.05 (6H2Si-Me, s). $^{13}$C NMR (100 MHz, CDCl$_3$) δ: 203.1, 196.1, 146.4, 146.2, 125.5, 118.9, 62.0, 61.5, 60.8, 57.2, 56.7, 53.9, 44.7, 41.7, 38.0, 36.1, 35.9 (2C, 1d, 1s), 27.3, 26.9, 26.1, 25.8 (3 CH3), 23.8, 21.7, 18.2, −5.3 (2Si—CH3). HREIMS m/z 483.3155 [M]$^+$ (C$_{29}$H$_{45}$O$_3$Si, calcd. 483.3169).

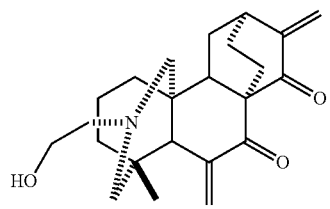

Compound 93: $^1$H NMR (400 MHz, CDCl$_3$) δ: 6.00 (1H, s), 5.96 (1H, s), 5.35 (1H, s), 5.32 (1H, s), 3.60 (2H, m), 2.87 (2H, m), 1.25-2.29 (20H, m), 0.93 (3H, s). $^{13}$C NMR (100 MHz, CDCl$_3$) δ: 203.5, 196.3, 146.4, 146.3, 126.3, 119.7, 61.1, 60.3, 57.9, 57.2, 56.2, 53.8, 44.7, 41.2, 38.1, 35.9 (2C), 35.7, 27.4, 26.9, 26.1, 23.9, 22.5. HREIMS m/z 369.2301 [M]$^+$ (C$_{23}$H$_{31}$NO$_3$, calcd. 369.2304).

Example 2. Inhibitory Effects of Compounds on Tumor Cell Lines (1) Experimental Methods 1. Inoculating cells: the culture medium DMEM or RMPI1640 containing 10% fetal bovine serum was used to prepare a single cell suspension, and the cell suspension was inoculated to a 96-well plate at 5000-10000 cells per well (100 μl for each well); Adherent cells were inoculated and cultured for 12 h in advance. HL-60 (human promyelocytic leukemia cells), SMMC-7721 (human hepatoma cells), A-549 (Human lung adenocarcinoma cells), MCF-7 (human breast cancer cells), SW-480 (human colon cancer cells) were purchased from the Cell Bank of the Chinese Academy of Sciences, Shanghai.

2. The solution of the compound to be tested (40 μM for primary screening; 5 concentrations were set for gradient re-screening for the compounds which achieve about 50% inhibition of tumor cell growth at 40 μM) was added, the final volume of each well was 200 μl, and triplicate wells were set for each test.

3. Coloration: After culturing at 37° C. for 48 h, MTT solution (20 μl) was added to each well. After incubation for another 4 h, the culture was stopped. The supernatant in each well was pipetted and discarded, and 200 μl SDS solution (10%) was added to each well. Incubation was performed overnight (at 37° C.), to completely dissolve the crystal.

4. Colorimetric assay: ELISA Reader (Bio-Rad 680) was used to obtain the light absorption for each well at a wavelength of 595 nm, the results were recorded. A cell growth curve was plotted with the concentration as abscissa and the cell survival percentage as ordinate. The two-point method (Reed and Muench method) was used to calculate the IC$_{50}$ of the compound.

(2) Screening Results:

TABLE 1

Anti-tumor activity of 7-hydroxy derivatives of S-3 (IC50, μM)

| Compound | HL-60 | SMMC-7721 | A-549 | MCF-7 | SW-480 |
|---|---|---|---|---|---|
| 1 | 6.36 | 3.96 | 3.22 | 3.25 | 3.58 |
| 1a | 2.39 | 1.67 | 2.18 | 2.74 | 1.96 |
| 1b | 1.46 | 3.60 | 2.83 | 3.48 | 3.44 |
| 1c | 1.13 | 0.78 | 0.64 | 3.67 | 2.86 |
| 1d | 1.05 | 1.23 | 0.50 | 3.47 | 3.00 |
| 1e | 4.44 | 4.10 | 2.96 | 2.74 | 2.37 |
| 1f | 5.72 | 13.00 | 6.08 | 2.74 | 7.81 |
| 1g | 6.86 | 10.20 | 5.97 | 5.85 | 6.42 |
| 1h | 4.59 | 3.50 | 2.61 | 2.70 | 3.38 |
| 1i | 3.37 | 3.35 | 2.59 | 2.58 | 2.50 |
| 1j | 2.99 | 0.74 | 2.97 | 3.71 | 3.95 |
| 1k | 0.86 | 2.89 | 1.05 | 0.80 | 0.69 |
| 1l | 4.20 | 3.60 | 2.46 | 3.07 | 2.43 |
| 1m | 0.89 | 2.65 | 1.73 | 1.97 | 2.19 |
| 1n | 4.01 | 3.05 | 2.14 | 3.11 | 2.22 |
| 1o | 0.84 | 0.60 | 0.49 | 1.26 | 0.56 |
| 1p | 1.24 | 1.79 | 0.79 | 3.40 | 2.16 |
| 1q | 5.15 | 10.54 | 4.17 | 3.82 | 3.43 |
| 1r | 0.58 | 0.57 | 0.49 | 2.06 | 1.17 |
| 1s | 3.53 | 3.83 | 2.69 | 4.18 | 2.89 |
| 1t | 3.36 | 3.64 | 2.94 | 3.19 | 1.91 |
| 1u | 6.63 | 23.40 | 6.69 | 9.05 | 18.45 |
| 1v | 9.64 | 26.86 | 16.64 | 11.14 | 14.65 |
| cis-DDP | 1.81 | 8.86 | 11.68 | 15.92 | 16.65 |
| TAXOL | <0.008 | <0.008 | <0.008 | <0.008 | <0.008 |

TABLE 2

Anti-tumor activity of derivatives having potential "Michael reaction acceptor" (IC50, μM)

| Compound | HL-60 | SMMC-7721 | A-549 | MCF-7 | SW-480 |
|---|---|---|---|---|---|
| 1 | 6.36 | 3.96 | 3.22 | 3.25 | 3.58 |
| 7 | 4.56 | 4.72 | 3.16 | 4.61 | 3.74 |
| 9 | 4.43 | 3.53 | 2.80 | 3.55 | 7.77 |
| 10 | 3.41 | 0.71 | 0.83 | 1.18 | 1.03 |
| 11 | 3.85 | 2.48 | 2.44 | 3.94 | 2.80 |
| 12 | 4.69 | 2.41 | 3.14 | 4.83 | 3.71 |
| 13 | 3.86 | 0.83 | 0.73 | 1.51 | 1.21 |
| 14 | 3.82 | 1.96 | 3.03 | 2.63 | 2.38 |
| 16 | 5.56 | 12.02 | 4.77 | 3.09 | 11.44 |
| 28 | 4.90 | 4.62 | 2.97 | 2.85 | 2.37 |
| 30 | 1.94 | 1.90 | 0.77 | 1.44 | 1.53 |
| 31 | 3.60 | 4.44 | 6.11 | 8.86 | 5.43 |
| 32 | 3.45 | 3.12 | 2.22 | 2.02 | 1.58 |
| 47 | 3.38 | 3.91 | 2.95 | 3.38 | 3.74 |

TABLE 2-continued

Anti-tumor activity of derivatives having potential "Michael reaction acceptor" (IC50, μM)

| Compound | HL-60 | SMMC-7721 | A-549 | MCF-7 | SW-480 |
|---|---|---|---|---|---|
| 48 | 5.03 | 6.13 | 3.04 | 2.93 | 3.94 |
| 49 | 6.50 | 13.99 | 10.97 | 12.81 | 15.51 |
| 50 | 6.30 | 10.83 | 4.69 | 4.23 | 6.57 |
| 52 | 6.33 | 15.44 | 11.10 | 15.13 | 12.88 |
| 75 | 3.78 | 5.97 | 3.64 | 4.12 | 8.01 |
| 76 | 5.28 | 13.14 | 4.04 | 5.96 | 7.69 |
| cis-DDP | 1.81 | 8.86 | 11.68 | 15.92 | 16.65 |
| TAXOL | <0.008 | <0.008 | <0.008 | <0.008 | <0.008 |

TABLE 3

Anti-tumor activity of derivatives having a single "Michael reaction acceptor" as obtained by modification of the lactonic ring (IC50, μM)

| Compound | HL-60 | SMMC-7721 | A-549 | MCF-7 | SW-480 |
|---|---|---|---|---|---|
| 1 | 6.36 | 3.96 | 3.22 | 3.25 | 3.58 |
| 21 | 4.20 | 1.87 | 3.17 | 5.04 | 4.19 |
| 22 | 1.46 | 0.51 | 0.67 | 1.57 | 2.20 |
| 25 | 4.87 | 4.92 | 3.25 | 4.00 | 6.33 |
| 28 | 4.90 | 4.62 | 2.97 | 2.85 | 2.37 |
| 36 | 16.97 | 10.88 | 13.69 | 18.53 | 24.59 |
| 38 | >40 | >40 | >40 | >40 | >40 |
| 39 | 28.77 | 34.76 | 17.46 | 21.53 | 20.73 |
| 41 | 1.58 | 0.90 | 2.18 | 2.24 | 2.09 |
| cis-DDP | 1.81 | 8.86 | 11.68 | 15.92 | 16.65 |
| TAXOL | <0.008 | <0.008 | <0.008 | <0.008 | <0.008 |
| 1 | 6.36 | 3.96 | 3.22 | 3.25 | 3.58 |
| 21 | 4.20 | 1.87 | 3.17 | 5.04 | 4.19 |
| 22 | 1.46 | 0.51 | 0.67 | 1.57 | 2.20 |
| 25 | 4.87 | 4.92 | 3.25 | 4.00 | 6.33 |
| 28 | 4.90 | 4.62 | 2.97 | 2.85 | 2.37 |
| 36 | 16.97 | 10.88 | 13.69 | 18.53 | 24.59 |
| 38 | >40 | >40 | >40 | >40 | >40 |
| 39 | 28.77 | 34.76 | 17.46 | 21.53 | 20.73 |
| 41 | 1.58 | 0.90 | 2.18 | 2.24 | 2.09 |
| cis-DDP | 1.81 | 8.86 | 11.68 | 15.92 | 16.65 |
| TAXOL | <0.008 | <0.008 | <0.008 | <0.008 | <0.008 |

TABLE 4

Anti-tumor activity of derivatives as obtained by reduction of the lactonic ring (IC50, μM)

| Compound | HL-60 | SMMC-7721 | A-549 | MCF-7 | SW-480 |
|---|---|---|---|---|---|
| 1 | 6.36 | 3.96 | 3.22 | 3.25 | 3.58 |
| 45 | 4.74 | 7.83 | 3.49 | 4.82 | 9.89 |
| 46 | 4.28 | 4.48 | 4.28 | 8.07 | 4.42 |
| 47 | 3.38 | 3.91 | 2.95 | 3.38 | 3.74 |
| 55 | 0.62 | 1.06 | 1.17 | 0.65 | 0.80 |
| 59 | 4.18 | 3.95 | 4.21 | 3.31 | 2.94 |
| 61 | 2.70 | 2.18 | 2.32 | 2.05 | 3.37 |
| 64 | 0.61 | 0.57 | 0.70 | 0.67 | 0.59 |
| 66 | 0.71 | 0.57 | 0.80 | 0.89 | 0.76 |
| 72a | 1.37 | 0.93 | 1.86 | 1.55 | 1.85 |
| 73a | 3.97 | 0.77 | 2.89 | 2.36 | 2.57 |
| 73b | 0.79 | 0.24 | 0.55 | 0.56 | 0.22 |
| cis-DDP | 1.81 | 8.86 | 11.68 | 15.92 | 16.65 |
| TAXOL | <0.008 | <0.008 | <0.008 | <0.008 | <0.008 |

TABLE 5

Anti-tumor activity of derivatives having double "Michael reaction acceptor" (IC50, μM)

| Compound | HL-60 | SMMC-7721 | A-549 | MCF-7 | SW-480 |
|---|---|---|---|---|---|
| 1 | 6.36 | 3.96 | 3.22 | 3.25 | 3.58 |
| 8 | 2.02 | 0.72 | 0.59 | 0.96 | 0.66 |
| 15 | 0.80 | 0.80 | 0.91 | 1.44 | 1.21 |
| 23 | 0.51 | 0.15 | 0.20 | 0.24 | 0.39 |
| 31 | 1.31 | 1.79 | 0.76 | 1.71 | 0.62 |
| 43 | 0.68 | 0.16 | 0.58 | 0.78 | 0.59 |
| 53 | 1.21 | 0.75 | 0.64 | 0.65 | 0.78 |
| 65 | 0.29 | 0.22 | 0.35 | 0.33 | 0.16 |
| 67 | 0.24 | 0.13 | 0.14 | 0.15 | 0.10 |
| 74a | 0.51 | 0.26 | 0.56 | 0.53 | 0.15 |
| 74b | 0.54 | 0.19 | 0.41 | 0.32 | 0.14 |
| cis-DDP | 1.81 | 8.86 | 11.68 | 15.92 | 16.65 |
| TAXOL | <0.008 | <0.008 | <0.008 | <0.008 | <0.008 |

TABLE 6

Activity on SW-480 cells of 7-hydroxyl derivatives, 7-carbonyl derivatives and derivatives having double "Michael reaction acceptor" (IC50, μM)

| 7-hydroxyl derivatives | SW-480 | 7-carbonyl derivatives | SW-480 | Derivatives having double "Michael reaction acceptor" | SW-480 |
|---|---|---|---|---|---|
| 1 | 2.99 | 7 | 2.63 | 8 | 0.45 |
| 21 | 2.90 | 22 | 2.56 | 23 | 0.79 |
| 25 | 4.12 | 28 | 2.06 | 31 | 0.45 |
| 41 | 2.09 | 42 | 1.83 | 43 | 0.34 |
| 45 | 2.81 | 47 | 3.67 | 53 | 0.78 |
| 63 | 2.97 | 64 | 0.71 | 65 | 0.26 |
| 70 | 1.69 | 66 | 0.70 | 67 | 0.13 |
| 72a | 2.23 | 73a | 2.57 | 74a | 0.65 |
| 72b | 0.09 | 73b | 0.18 | 74b | 0.48 |
| 72c | 0.81 | 73c | 0.69 | 74c | 0.33 |
| 72d | 0.52 | 73d | 0.62 | 74d | 0.15 |
| 72e | — | 73e | — | 74e | — |
| cis-DDP | 11.07 | | | | |
| TAXOL | <0.008 | | | | |

TABLE 7

Anti-tumor activity of alkaloid derivatives (IC50, μM)

| Compound | HL-60 | SMMC-7721 | A-549 | MCF-7 | SW-480 |
|---|---|---|---|---|---|
| 1 | 6.36 | 3.96 | 3.22 | 3.25 | 3.58 |
| 77 | 1.34 | 1.04 | 2.03 | 0.67 | 1.97 |
| 78 | 2.73 | 2.63 | 3.09 | 1.12 | 2.81 |
| 80 | 4.03 | 5.02 | 8.45 | 3.12 | 5.47 |
| 82 | 19.27 | 23.63 | 18.57 | 10.35 | 13.99 |
| 83 | 18.59 | 18.35 | 17.94 | 13.23 | 12.41 |
| 84 | 18.55 | 15.73 | 19.02 | 15.73 | 14.19 |
| 88 | 7.95 | 11.16 | 9.92 | 16.57 | 14.41 |
| 89 | 4.82 | 1.48 | 3.04 | 6.98 | 9.84 |
| 91 | 14.32 | 15.19 | 9.24 | 15.70 | 11.82 |
| 92 | 1.39 | 2.63 | 1.55 | 2.90 | 2.78 |
| 93 | 6.61 | 11.52 | 6.50 | 3.57 | 2.81 |
| cis-DDP | 3.08 | 10.20 | 9.08 | 17.48 | 11.99 |
| TAXOL | <0.008 | <0.008 | <0.008 | <0.008 | <0.008 |

Example 3. Inhibitory Effects of Compounds on Top-Flash, a Reporter Gene of the Wnt Signaling Pathway (1) Experimental Methods:
1) Cell Culture and Preparation of Conditioned Medium:
HEK293T cells were cultured in DMEM containing 10% fetal bovine serum (Invitrogen) at 37° C., 5% $CO_2$. The cells were passaged every other day. The density was retained at 70~80% during passage. L cell line (CRL-2647, purchased from the gene bank of ATCC, the US) and the control cell line (CRL-2648, purchased from ATCC, US), which stably secreted mouse Wnt3a protein, were cultured in DMEM containing 50 ug/ml G418 and 10% fetal bovine serum, at 37° C., 5% $CO_2$. When the cells grew to a density of about 70%, the medium was replaced with DMEM containing 10% fetal bovine serum. After continuous culture for 4 days, the culture was collected and centrifuged, and the supernatant was kept so that the Wnt conditioned medium was obtained. After titration assay, the conditioned medium was quick-frozen in liquid nitrogen, and placed at −80° C. for long-term storage, so that the titer was kept unchanged.
2) Cell Transfection:
The cells were seeded to a 48-well plate at a density of $2.0~2.5 \times 10^6$ cells per well, and transfected 20 h later. The reagents for plasmid transfection were calculated based on the amount in each well of the 48-well plate as following: the total amount of plasmid was 125 ng/well; the plasmid was first added to a serum-free medium (25 μL/well) and mixed well; PLUS reagent (Invitrogen) was then added in an amount of 0.5 μL/well and mixed well, then stood for 15 min; Lipofectamine (Invitrogen) liposome was added in an amount of 0.5 μL/well to serum-free DMEM medium (25 μL/well), and then mixed with the solution containing the plasmid and the PLUS, and stood for 15 min. The cells were cultured in serum-free DMEM medium (100 μL/well), and the final mixture of plasmid, PLUS and Lipofectamine were added to the cells. After incubation for 3 h, the transfection was stopped by the medium containing 10% fetal bovine serum (200 μL/well).
3) Activity Assay of Wnt Reporter Gene and Calculation of $IC_{50}$:
The HEK293T cells used for activity assay of the report gene were transfected by the method as shown in 2). Activity assay of Wnt reporter gene: the amount of plasmid for transfection was 5 ng/well for TOP-flash and 5 ng/well for GFP plasmid as internal standard, with lacZ added to reach a total amount of 125 ng/well. 18 h after transfection, the control medium containing DMSO and the Wnt3a conditioned medium comprising different concentrations of the compound to be tested (DMSO, 2.5 μM, 5 μM, 10 μM, 15 μM, 20 μM, 30 μM; for the compound to be tested with an $IC_{50}$ of above 30 μM, the concentrations were DMSO, 5 μM, 15 μM, 30 μM, 40 μM, 50 μM, and 60 μM) were added. After treating for 6 h, Boehringer Mannheim Luci-ferase Assay Kit was used to lyse cells (200 μL/well). 50 μL from each well was pipetted into a 96-well plate. The indensity of GFP protein in the cell lysate was measured by fluorimeter FL600 (BIO-TEK Inc. Winooski, Vt.), and taken as internal standard for cell transfection efficiency. 10 μL substrate of luciferase was then added to each well, and the activity of luciferase was measured by Micro Lumate Plus (Perkin Elmer Inc. Wellesley, Mass.) luminometer. Finally, GFP indensity was used as internal standard to calibrate the activity of luciferase, i.e. the activity of Wnt reporter gene.

Calculation of $IC_{50}$ (taking the calculation of $IC_{50}$ of the Wnt signaling pathway for example): background (the activity as measured in the groups treated with a conditioned medium containing DMSO only) was subtracted from the reporter gene activity as measured in the groups treated by Wnt3a conditioned medium with or without the compound to be tested at different concentrations; and the obtained value was defined as the activity of the reporter gene induced by Wnt or the residual activity of the reporter gene after adding the compound to be tested. The residual activity was normalized by the activity induced by Wnt to get the relative residual activity. Then combine with the concentrations of the compound to be tested to plot a linear graph, and a dose-effect curve was fitted based on 4-parameter logistic fit. $IC_{50}$ of the Wnt signaling pathway is determined as the concentration at which the relative residual activity is 0.5.

(2) Screening Results:

TABLE 7

Inhibitory activity on the Wnt signaling pathway of derivatives modified on 7-hydroxyl of S-3 ($IC_{50}$, μM)

| Compound | $IC_{50}$ (μM) |
|---|---|
| 1 | 18.35 ± 1.82 |
| 1a | 18.30 ± 0.66 |
| 1b | 14.15 ± 0.67 |
| 1c | 17.89 ± 0.98 |
| 1d | 28.84 ± 0.56 |
| 1e | 22.14 ± 0.10 |
| 1f | 20.17 ± 2.59 |
| 1g | 29.99 ± 2.22 |
| 1h | 20.25 ± 0.99 |
| 1i | 28.26 ± 2.76 |
| 1j | 14.66 ± 0.18 |
| 1k | 10.73 ± 0.39 |
| 1l | 18.62 ± 1.48 |
| 1m | 18.99 ± 1.61 |
| 1n | 18.95 ± 2.48 |
| 1o | 9.15 ± 1.14 |
| 1p | 18.61 ± 1.26 |
| 1q | 15.10 ± 2.89 |
| 1r | 8.92 ± 0.98 |
| 1s | 12.37 ± 1.00 |
| 1t | 14.41 ± 2.28 |
| 1u | >60 (30%) |
| 1v | >60 (30%) |
| 7 | 12.05 ± 1.88 |

TABLE 8

Inhibitory activity on the Wnt signaling pathway of derivatives of the diterpene from *Spiraea japonica* L. f. ($IC_{50}$, μM)

| Compound | $IC_{50}$ (μM) |
|---|---|
| 1 | 18.73 ± 0.58 |
| 7 | 12.05 ± 1.88[a] |
| 21 | 27.35 ± 0.98 |
| 22 | 17.56 ± 1.90 |
| 25 | 21.71 ± 0.63 |
| 28 | 9.12 ± 0.21 |
| 36 | 18.05 ± 2.67 |
| 38 | >60 (0) |
| 39 | >60 (15%) |
| 41 | >60 (20%) |
| 45 | 9.98 ± 1.00 |
| 47 | 16.89 ± 1.89 |
| 64 | 7.83 ± 0.70 |
| 66 | 8.39 ± 0.63 |
| 72a | 12.59 ± 1.04 |
| 73a | 42.99 ± 5.35 |
| 73b | 10.36 ± 0.57 |

[a]The corresponding $IC_{50}$ value of S-3 is 18.35 ± 1.82

TABLE 9

Inhibitory activity on the Wnt signaling pathway of derivatives of the diterpene from *Spiraea japonica* L. f. (IC$_{50}$, μM)

| Compound | IC$_{50}$(μM) |
|---|---|
| 1 | 17.97 ± 0.28 |
| 8 | 4.09 ± 0.07 |
| 9 | 8.56 ± 1.15 |
| 10 | 9.54 ± 1.34 |
| 11 | 6.89 ± 0.27 |
| 12 | 19.75 ± 1.34[b] |
| 13 | 16.46 ± 1.16[b] |
| 14 | 20.06 ± 1.32[b] |
| 15 | 11.05 ± 0.63 |
| 16 | 8.27 ± 1.24 |
| 23 | 6.72 ± 1.11 |
| 29 | >60 (24%) |
| 31 | 7.10 ± 0.70 |
| 43 | 12.85 ± 0.13 |
| 48 | 46.93 ± 1.26 |
| 49 | 58.22 ± 1.18 |
| 50 | 56.04 ± 0.92 |
| 52 | >60 (10%) |
| 53 | 7.30 ± 0.22[a] |
| 65 | 7.68 ± 0.19 |
| 67 | 4.92 ± 0.69 |
| 74a | 11.18 ± 1.54 |
| 74b | 7.2 ± 0.71 |
| 75 | >60 (33%) |
| 76 | >60 (21%) |

[a] The corresponding IC$_{50}$ value of S-3 is 15.34 ± 0.5 μM,
[b] The corresponding IC$_{50}$ value of S-3 is 18.35 ± 1.82 μM

TABLE 10

Inhibitory activity on the Wnt signaling pathway of derivatives of the diterpene from *Spiraea japonica* L. f. (IC$_{50}$, μM)

| Compound | IC$_{50}$ (μM) |
|---|---|
| 1 | 13.91 ± 2.01 |
| 30 | 15.41 ± 1.50 |
| 32 | 19.80 ± 1.04 |
| 33 | 12.06 ± 1.25 |
| 46 | 27.74 ± 2.80 |
| 55 | 12.14 ± 1.25 |
| 59 | 43.78 ± 3.05 |
| 61 | 32.30 ± 3.01 |

TABLE 11

Inhibitory activity on the Wnt signaling pathway of derivatives of the diterpene from *Spiraea japonica* L. f. (IC$_{50}$, μM).

| Compound | IC$_{50}$ (μM) |
|---|---|
| 1 | 22.49 ± 0.56 |
| 77 | >60 (35%) |
| 78 | 28.67 ± 0.97 |
| 83 | >60 (26%) |
| 84 | 60.63 ± 3.09 |
| 88 | >60 (0) |
| 89 | 8.34 ± 0.90 |
| 91 | 49.35 ± 1.42 |
| 93 | 17.04 ± 1.28 |

Example 4

Tablet: any of the compounds as obtained in Example 1 (10 mg), lactose (180 mg), starch (55 mg), and magnesium stearate (5 mg).

Preparation method: the compound, lactose and starch were mixed and well moistened with water. The moistened mixture was subjected to mesh screening and dried; and subjected to mesh screening again. Magnesium stearate was added; and the resultant mixture was tableted, wherein each tablet was weighted 250 mg, and contained 10 mg of the compound.

Example 5

Ampulla: any of the compounds as obtained in Example 1 (2 mg), sodium chloride (10 mg);

Preparation method: the compound and sodium chloride were dissolved in a suitable amount of water for injection; and filtered to get a filtrate, which was packaged into an ampulla under aseptic condition.

Example 6

Capsule: any of the compounds as obtained in Example 1 (10 mg), lactose (187 mg), magnesium stearate (3 mg)

Preparation method: the compound was mixed with the adjuvants, and subjected to mesh screening, and well mixed; the resultant mixture was packaged into hard gelatin capsules, wherein each capsule was weighted 200 mg and contained 10 mg of active ingredient.

Although the embodiments of the invention have been described in detail, a person skilled in the art would understand that a variety of modifications and replacements may be made to the details according to the teachings as disclosed herein. These changes all fall within the protection scope of the invention. The scope of the invention is defined by the claims and any equivalent thereof.

The invention claimed is:

1. A compound of Formula II, or a solvate or a pharmaceutically acceptable salt thereof,

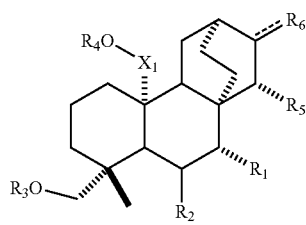

wherein,
$X_1$ is —CH$_2$ or —CO;
$R_1$ and $R_5$ independently are —OH, or carbonyl oxygen;
$R_2$ is selected from —H, carbonyl oxygen, =CH$_2$, —CH$_2$OH, —CH$_2$OCOCH$_3$, —CH$_2$OSO$_2$CH$_3$, halogen, —CH$_2$NR$_7$R$_8$ and —CH$_2$R$_1$;
$R_7$ and $R_8$ may be the same or different, or may form a N-containing 5-membered or 6-membered ring together with the N which they are linked to;
$R_6$ is =CH$_2$ linked to the C atom on the ring via the double bond represented by ⁼⁼⁼;
$R_3$ and $R_4$ are independently selected from —OH, —COCH$_3$, —COCH$_2$CH$_3$, —COCH$_2$Cl, -Ms, —CH$_2$CN, 2-thenoyl, and benzoyl; or
$R_3$ and $R_4$ are independently selected from hydroxyl, carbonyloxy, C$_{1-6}$alkylacyl, benzoyl, C$_{1-6}$ alkylsulfonyl, phenylsulfonyl, phenylmethylsulfonyl, and cinnamoyl; wherein R₃ and R₄ may be optionally substituted with one or more substituents selected from halogen, $C_{1-6}$ alkyl, $C_{1-6}$ alkenyl, nitro, $C_{1-6}$alkoxy, triazo, trifluoromethyl, furyl, and thienyl; or R₃ and R₄ are independently selected from —CO(CH₂)ₙCH₃ and —CO(CH₂)ₙCH₂X; wherein n=1-8, and X is a halogen.

2. The compound, or the solvate or pharmaceutically acceptable salt thereof according to claim 1, wherein, R₃ and R₄ are independently selected from —OH, —COCH₃, —COCH₂CH₃, —COCH₂Cl, —CON(CH₂)₄O, -Ms, —CH₂CN, 2-thenoyl, benzoyl, p-nitrobenzoyl, formyl, acetyl, 2-chloroacetyl, 2-bromoacetyl, 2-triazoacetyl, trifluoroacetyl, acryloyl, 3-chloropropionyl, 2-chloropropionyl, benzoyl, p-nitrobenzoyl, o-nitrobenzoyl, m-nitrobenzoyl, p-methoxybenzoyl, p-trifluoromethylbenzoyl, o-trifluoromethylbenzoyl, m-trifluoromethylbenzoyl, 2-furoyl, 3-furoyl, 2-thenoyl, 3-thenoyl, cinnamoyl, methylsulfonyl, phenylmethylsulfonyl, phenylsulfonyl, p-chlorophenylsulfonyl, m-chlorophenylsulfonyl, o-chlorophenylsulfonyl, and o-nitrobenzoyl.

3. The compound, or the solvate or pharmaceutically acceptable salt thereof according to claim 1, selected from the following compounds:

(38)

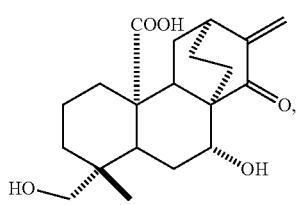

(45)

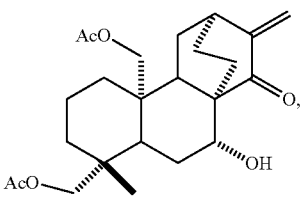

(46)

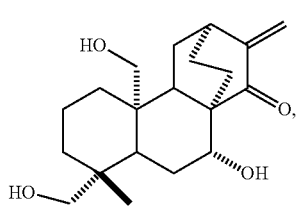

(47)

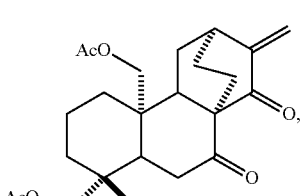

(48)

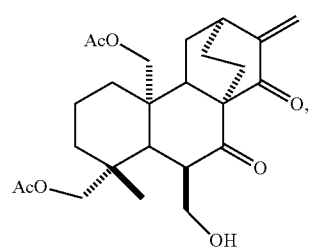

(49)

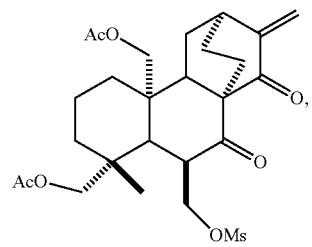

(50)

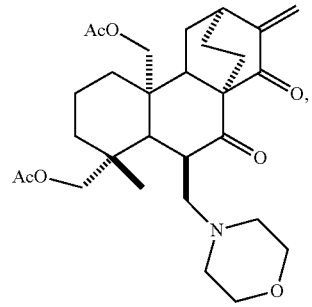

(51)

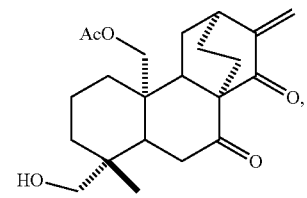

(52)

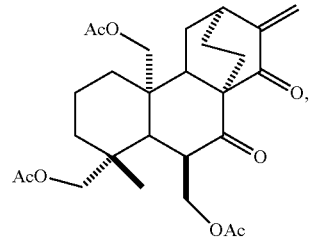

(53)

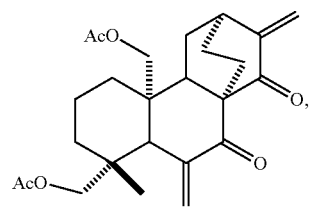

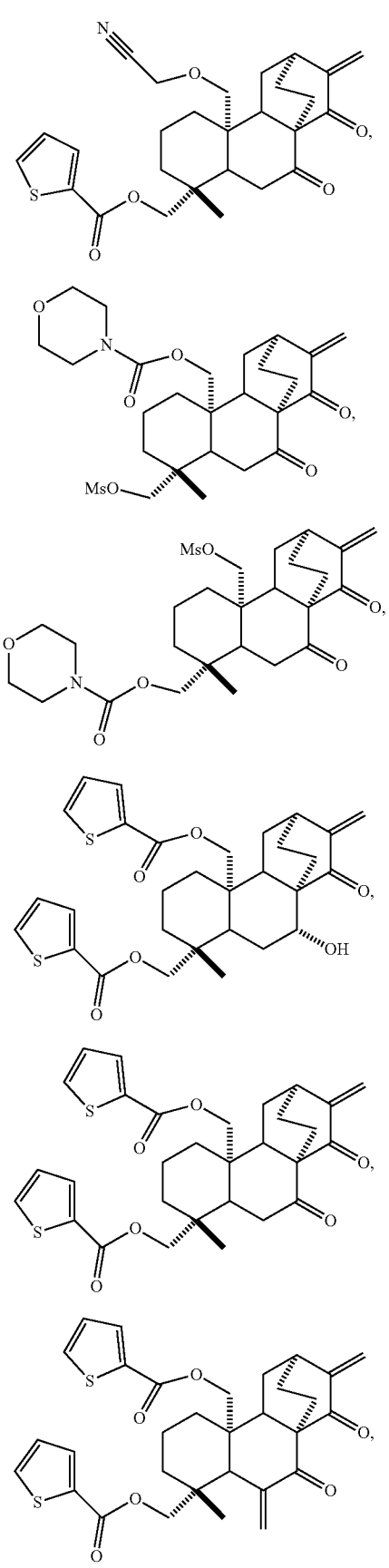
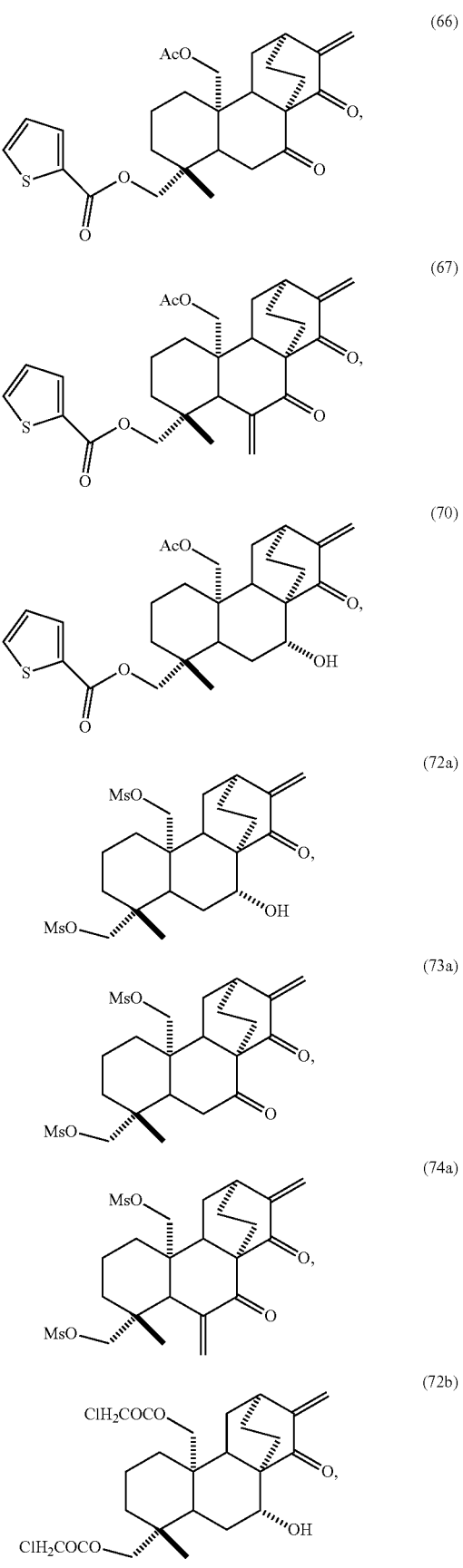

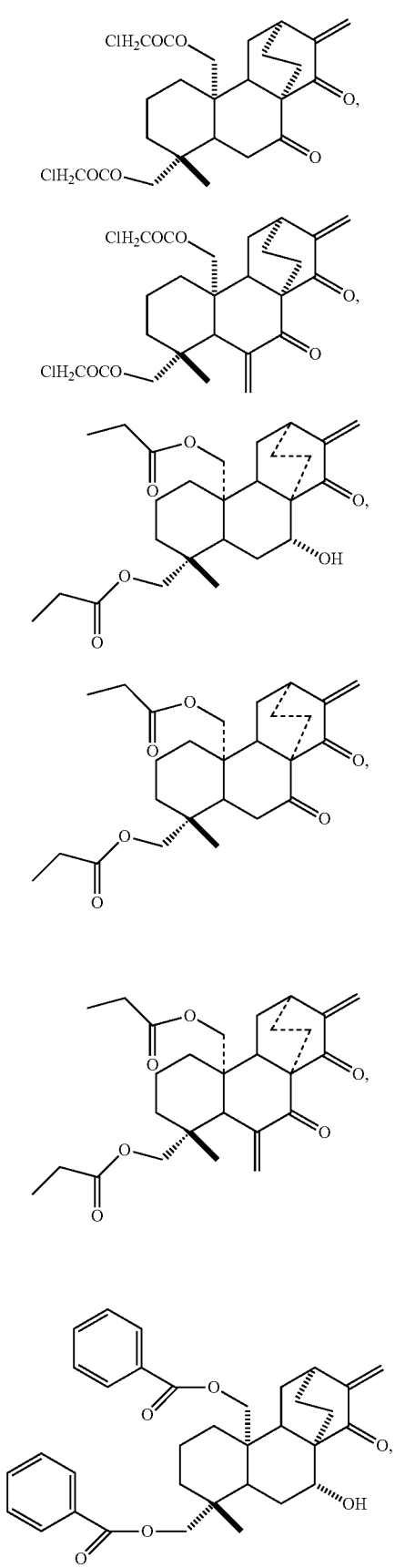
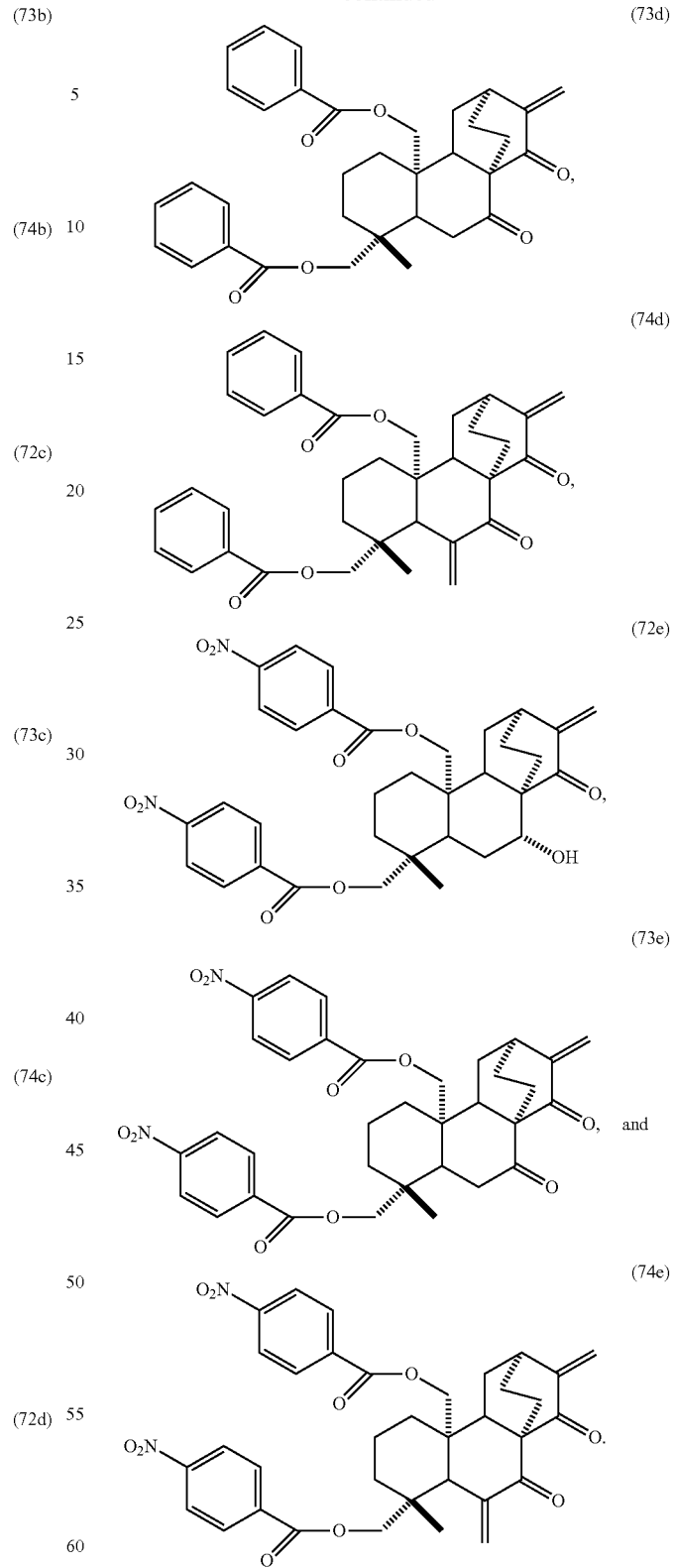
4. The compound, or the solvate or pharmaceutically acceptable salt thereof according to claim 1 wherein $R_3$ and $R_4$ are independently selected from groups of hydroxyl, carbonyloxy, $C_{1-6}$alkylacyl, benzoyl, $C_{1-6}$alkylsulfonyl, phenylsulfonyl, phenylmethylsulfonyl, and cinnamoyl, wherein said groups are optionally substituted with 2, 3, or 4 substituents selected from halogen, $C_{1-6}$ alkyl, $C_{1-6}$ alkenyl, nitro, $C_{1-6}$ alkoxy, triazo, trifluoromethyl, furyl, and thienyl.

5. A pharmaceutical composition, which comprises a therapeutically effective amount of one or more of the compound, or the solvate or pharmaceutically acceptable salt thereof according to claim 1 and a pharmaceutically acceptable carrier or adjuvant.

6. A pharmaceutical composition, which comprises a therapeutically effective amount of one or more of the compound, or the solvate or pharmaceutically acceptable salt thereof according to claim 3 and a pharmaceutically acceptable carrier or adjuvant.

* * * * *